(12) United States Patent
Lewis et al.

(10) Patent No.: US 10,201,615 B2
(45) Date of Patent: Feb. 12, 2019

(54) SYNERGISTIC EFFECTS BETWEEN AURISTATIN-BASED ANTIBODY DRUG CONJUGATES AND INHIBITORS OF THE PI3K-AKT MTOR PATHWAY

(71) Applicant: Seattle Genetics, Inc., Bothell, WA (US)

(72) Inventors: Timothy S. Lewis, Bothell, WA (US); Che-Leung Law, Bothell, WA (US); Julie A. McEarchern, Bothell, WA (US)

(73) Assignee: SEATTLE GENETICS, INC., Bothell, WA (US)

( * ) Notice: Subject to any disclaimer, the term of this patent is extended or adjusted under 35 U.S.C. 154(b) by 0 days.

(21) Appl. No.: 15/008,365

(22) Filed: Jan. 27, 2016

(65) Prior Publication Data

US 2016/0220693 A1   Aug. 4, 2016

Related U.S. Application Data

(62) Division of application No. 13/879,012, filed as application No. PCT/US2011/057130 on Oct. 20, 2011, now Pat. No. 9,272,052.

(60) Provisional application No. 61/445,785, filed on Feb. 23, 2011, provisional application No. 61/405,767, filed on Oct. 22, 2010.

(51) Int. Cl.
| | |
|---|---|
| *A61K 47/48* | (2006.01) |
| *A61K 31/436* | (2006.01) |
| *A61K 45/06* | (2006.01) |
| *A61K 31/4375* | (2006.01) |
| *A61K 31/4745* | (2006.01) |
| *A61K 31/498* | (2006.01) |
| *A61K 31/519* | (2006.01) |
| *A61K 31/5377* | (2006.01) |
| *A61K 39/395* | (2006.01) |

(52) U.S. Cl.
CPC ...... *A61K 47/48561* (2013.01); *A61K 31/436* (2013.01); *A61K 31/4375* (2013.01); *A61K 31/4745* (2013.01); *A61K 31/498* (2013.01); *A61K 31/519* (2013.01); *A61K 31/5377* (2013.01); *A61K 39/3955* (2013.01); *A61K 45/06* (2013.01); *A61K 47/4863* (2013.01); *A61K 47/48415* (2013.01)

(58) Field of Classification Search
CPC .............................. A61K 47/48; A61K 31/436
USPC ........................................... 424/179.1, 178.1
See application file for complete search history.

(56) References Cited

U.S. PATENT DOCUMENTS

| | | | |
|---|---|---|---|
| 7,829,531 B2 | 11/2010 | Senter et al. | |
| 8,758,758 B1 | 6/2014 | Sievers et al. | |
| 9,211,319 B2 * | 12/2015 | Sievers | A61K 39/00 |
| 9,272,052 B2 | 3/2016 | Lewis et al. | |
| 2009/0028856 A1 | 1/2009 | Chen et al. | |
| 2009/0068178 A1 | 3/2009 | Crowley et al. | |
| 2009/0324621 A1 | 12/2009 | Senter et al. | |
| 2010/0028346 A1 | 2/2010 | Lutz et al. | |
| 2010/0144647 A1 | 6/2010 | Kratz et al. | |
| 2010/0227838 A1 | 9/2010 | Shah et al. | |
| 2011/0268751 A1 | 11/2011 | Sievers et al. | |

FOREIGN PATENT DOCUMENTS

| | | |
|---|---|---|
| WO | WO 04/010957 A2 | 4/2009 |
| WO | WO 09/048967 A1 | 4/2009 |
| WO | WO 09/117531 A1 | 9/2009 |

OTHER PUBLICATIONS

Janes et al. (Nature Medicine, Jan. 13, 2010, 16 (2): 205-214).*
"Hodgkin Lymphoma", National Cancer Institute, Medical Definition of Hodgkin Lymphoma, 1 page, (2014). [Author Unknown].
"The new mechanisms: effect in advanced renal cancer," Medicament News, New drug outlook, 2018:24-24, (2010). [Author Unknown].
Berenbaum, "Synergy, additivism and antagonism in immunosuppressiun," Clin Exp Immunol, 28:1-18, (1997).
Cheson, "Novel therapies for peripheral T-cell non-Hodgkin's lymphomas." Current Opinion In Hematology. 16(4):299-305, (2009).
Cho et al., "The Efficacy of the Novel Dual PI3-Kinase/mTOR inhibitor NVP-BEZ235 Compared with Rapamycin in Renal Cell Carcinoma," Clin Cancer Res. 16(14):3628-3638, (2010).
Dutton et al., "Constitutive activation of phosphatidyl-inositide 3 kinase contributes to the survival of Hodgkin's lymphoma cells through a mechanism involving Akt kinase and mTOR," J Pathol, 205:498-506, (2005).
EPO Application No. EP 11835158.4, Supplementary European Search Report and European Search Opinion, dated Nov. 13, 2014.
Francisco et al., "cAC1O-vcMMAE, an anti-CD30-monomethyl E conjugate with potent and selective antitumor activity," Blood, 102(4):1458-1465, (2003).
Georgakis et al. , "The mTOR Inhibitor Temsirolimus (CCI-779) induces Cell Cycle Arrest and Autophagy in Hodgkin Lymphoma (HL) Cell Lines and Enhances the Effect of the PI3-Kinase Inhibitor LY294002," Blood, ASH Annual Meeting Abstracts, 108:Abstract 2259, 2 pages, (2006). [Retrieved from the Internet April 30, 2015: <URL: http://abstracts.hematologylibrary.org/cgi/content/short/108/11/2259>].
Gerber et al., "Potent antitumor activity of the anti-CD19 auristatin antibody drug conjugate hBU12-vcMMAE against fittodmab-sensitive and -resistant lymphomas," Blood, 113(18):4352-4361. (2009).
Johnston et al., "A Phase II trial of the oral mTOR inhibitor everolimus in relapsed Hodgkin lymphoma." Am J Hematol. 85:320-324 (2010).

(Continued)

*Primary Examiner* — Yan Xiao
(74) *Attorney, Agent, or Firm* — Alston & Bird LLP

(57) ABSTRACT

The present invention is directed to methods for treating cancer comprising administering to a subject in need thereof an auristatin-based antibody drug conjugate and an inhibitor of the PI3K-AKT-mTOR pathway.

21 Claims, 9 Drawing Sheets

Specification includes a Sequence Listing.

(56) References Cited

OTHER PUBLICATIONS

Jona et al., "Novel treatment strategies for patients with relapsed classical Hodgkin lymphoma," Blood Rev., 24(6)233-238, (2010).
Kawai, "Future development of molecular target drugs against renal cell carcmoma," Jpn J Cancer Chemother, 35(1)31-34, (2008).
Law et al.. "Efficient Elimination of B-Lineage Lymphomas by Anti-CD2O-Auristatin Conjugates" Clin Cancer Res, 10(23):7842-7851, (2004).
Lewis et al., "Auristatin-based antibody-drug conjugates are synergistic in combination with PI3K-AKT-mTOR pathway inhibitors in hematologic malignancies and carcinoma," Cancer Research, Proceedings of the 102nd Annual Meeting of the American Association for Cancer Research ,71(8 Suppl):Abstract No. 1789, doi:10 1158/1 5 38-74 45 AM 2011-1789, (2011).
McEarchern et al., "Activity of SGN-35 in Preclinical Models of Combination Therapy and Relapse Prevention," Haematologica, the hematology journal, 95(84):85-85. abstract No. P017, (2010).
Oflazoglu et al., "Combination or the anti-CD30-auristatin-E antibody-drug conjugate (SGN-335) with chemotherapy improves antitumour activity in Hodgkin lymphoma." Br J Haematol, 142:69-73, (2008).
Oflazoglu et al., "Potent Anticarcinoma Activity of the Humanized Anti-CD70 Antibody h1F6 Conjugated to the Tubulin Inhibitor Auristatin via an Uncleavable Linker," Clin Cancer Res, 14(19):6171-6180, (2008).
Satoshi et al., "The induction of apoptosis by inhibition of signaling system via the Akt in renal cell carcinoma cell line," The Japanese Journal of Urology, PP-765, 94(2):388-388, (2003).

Teachey et al., "The mTOR inhibitor CCI-779 induces apoptosis' and inhibits growth in preclinical models of primary adult human ALL," Blood, 107(3):1149-1155, (2006).
U.S. Appl. No. 13/879,012, Final Rejection dated May 8, 2015.
U.S. Appl. No. 13/879,012, Non-Final Rejection dated Nov. 12, 2014.
U.S. Appl. No. 13/879,012, Requirement for Restriction/Election dated Jul. 16, 2014.
Wiesenthal Ed., "Synergy analysis of 'classic' and newer cancer chemotherapy combinations," Human Tumor Assay Journal, 1 page, (2012). [Retrieved from the Internet Mar. 14, 2012: <URL: http://weisenthal.org/synergyl.htm>].
WIPO Application No. PCT/US2011/057130, International Preliminary Report on Patentability, dated Sep. 17, 2013.
WIPO Application No. PCT/US2011/057130, International Search Report, dated Feb. 28, 2012.
WIPO Application No. PCT/US2011/057130, Written Opinion of the International Searching Authority, dated Feb. 28, 2012.
Yazbeck et al.," Temsirolimus downregulates p21 without altering cyclin D1 expression and induces autophagy and synergizes with vorinostat in mantle cell lymphoma," Experimental Hematology, 36:443-450, (2008).
Younes et al., "Multiple complete responses in a phase 1 dose-escalation study of the antibody-drug conjugate SGN-35 in patients with relapsed or refractory CD30-positive lymphomas," Blood, ASH Annual Meeting Abstracts, 112:Abstract 1006, (2008).

* cited by examiner

SYNERGISTIC EFFECTS BETWEEN AURISTATIN-BASED ANTIBODY DRUG CONJUGATES AND INHIBITORS OF THE PI3K-AKT MTOR PATHWAY

CROSS-REFERENCE TO RELATED APPLICATIONS

This application is a divisional of U.S. Ser. No. 13/879,012 filed Apr. 11, 2013, which is a national stage of PCT/US2011/057130 filed Oct. 20, 2011, which claims the benefit of U.S. 61/405,767 filed Oct. 22, 2010 and U.S. 61/445,785 filed Feb. 23, 2011, each of which is incorporated by reference in its entirety for all purposes.

REFERENCE TO A SEQUENCE LISTING

This application includes an electronic sequence listing in a file named 472679_seqlst.txt, created on Jan. 15, 2016 and containing 14,459 bytes, which is hereby incorporated by reference in its entirety for all purposes.

TECHNICAL FIELD

Provided herein are pharmaceutical compositions and the use thereof in the treatment of cancers. In particular, the methods and compositions described herein are based, in part, on the discovery that auristatin-based antibody drug conjugates and inhibitors of the PI3K-AKT-mTOR pathway act synergistically to kill tumor cells and/or inhibit the proliferation of tumor cells.

General Introduction

The present invention provides, inter alia, methods for treating cancers, and, in particular, cancers that demonstrate upregulation of the PI3K-AKT-mTOR pathway. In one aspect, the methods comprise the step of administering to a subject in need thereof an auristatin based drug conjugate and an inhibitor of the PI3K-AKT-mTOR pathway, in therapeutically effective amounts. In some embodiments, administration of the auristatin based drug conjugate and the inhibitor of the PI3K-AKT-mTOR pathway provide a synergistic effect in the treatment of the cancer. In some embodiments, administration of the auristatin based drug conjugate and the inhibitor of the PI3K-AKT-mTOR pathway provide a synergistic effect in the killing of tumor cells and/or inhibition of proliferation of tumor cells.

DEFINITIONS AND ABBREVIATIONS

Figure 1:
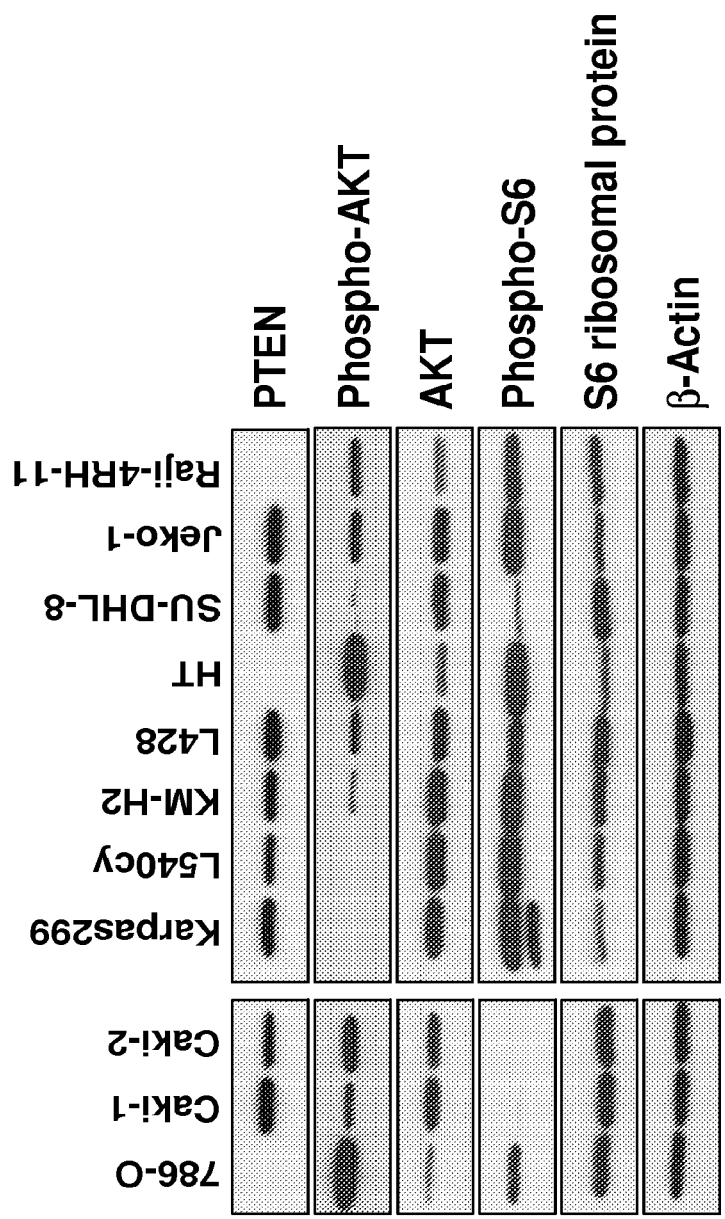
FIGS. 1 and 1A show the levels of phospho-AKT, AKT, phospho-56, S6, phospho-4E-BP1, 4E-BP1, PTEN and B-actin in select cancer cell lines.
Figure 1A:
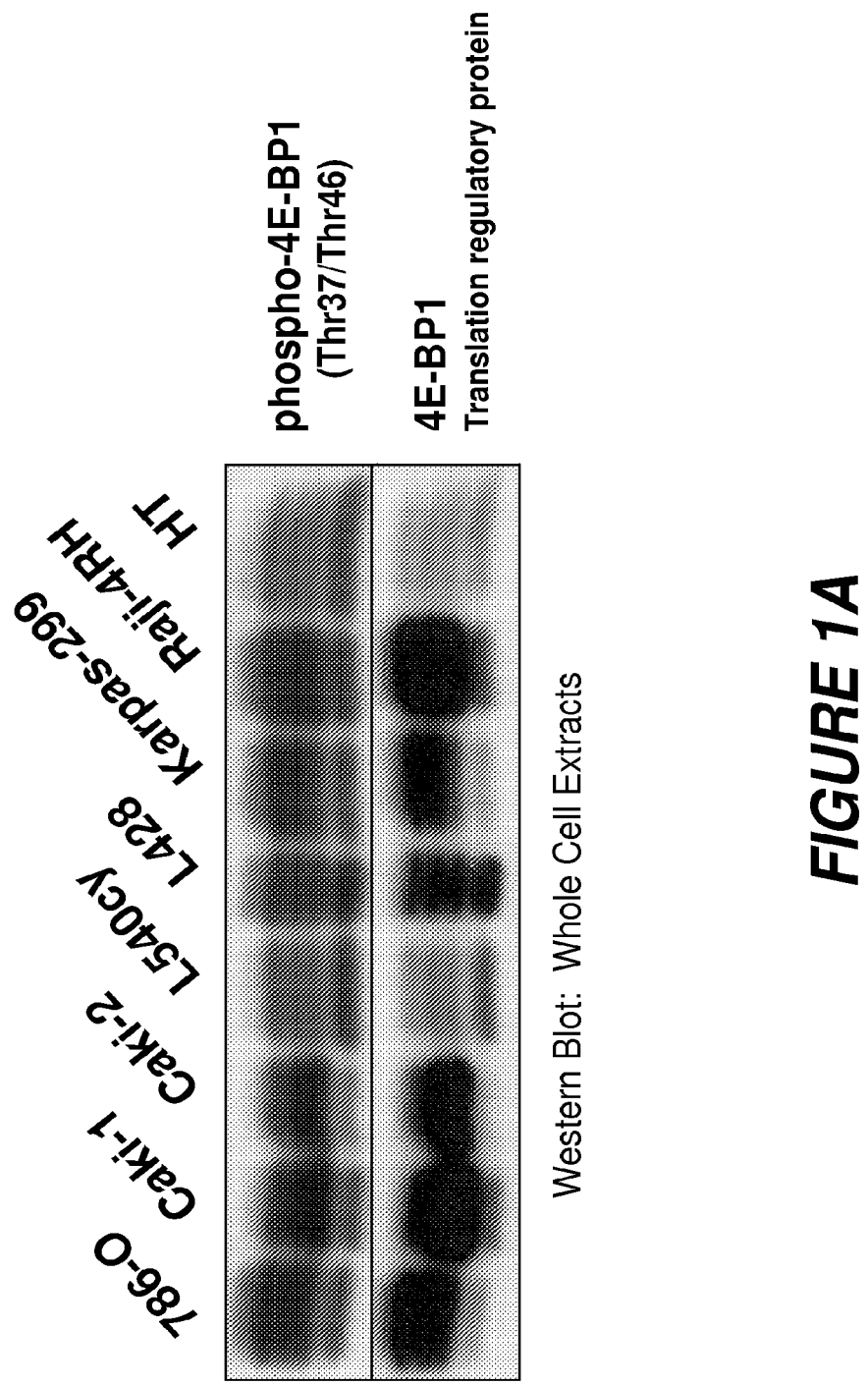

Unless defined otherwise, all technical and scientific terms used herein have the same meaning as commonly understood by one of ordinary skill in the art pertinent to the methods and compositions described. As used herein, the following terms and phrases have the meanings ascribed to them unless specified otherwise.

Unless otherwise noted, the term "alkyl" refers to a saturated straight or branched hydrocarbon having from about 1 to about 20 carbon atoms (and all combinations and subcombinations of ranges and specific numbers of carbon atoms therein), with from about 1 to about 8 carbon atoms being preferred. Examples of alkyl groups are methyl, ethyl, n-propyl, iso-propyl, n-butyl, iso-butyl, sec-butyl, tert-butyl, n-pentyl, 2-pentyl, 3-pentyl, 2-methyl-2-butyl, n-hexyl, n-heptyl, n-octyl, n-nonyl, n-decyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, and 3,3-dimethyl-2-butyl.

Alkyl groups, whether alone or as part of another group, may be referred to as "substituted." A substituted alkyl group is an alkyl group that is substituted with one or more groups, preferably 1 to 3 groups (and any additional substituents selected from halogen), including, but not limited to, -halogen, —O—($C_1$-$C_8$ alkyl), —O—($C_2$-$C_8$ alkenyl), —O—($C_2$-$C_8$ alkynyl), -aryl, —C(O)R', —OC(O)R', —C(O)OR', —C(O)$NH_2$, —C(O)NHR', —C(O)N(R')$_2$, —NHC(O)R', —SR', —$SO_3$R', —S(O)$_2$R', —S(O)R', —OH, =O, —$N_3$, —$NH_2$, —NH(R'), —N(R')$_2$ and —CN, where each R' is independently selected from —H, —$C_1$-$C_8$ alkyl, —$C_2$-$C_8$ alkenyl, —$C_2$-$C_8$ alkynyl, or -aryl, and wherein said —O—($C_1$-$C_8$ alkyl), —O—($C_2$-$C_8$ alkenyl), —O—($C_2$-$C_8$ alkynyl), -aryl, —$C_1$-$C_8$ alkyl, —$C_2$-$C_8$ alkenyl, and —$C_2$-$C_8$ alkynyl groups can be optionally further substituted with one or more groups including, but not limited to, —$C_1$-$C_8$ alkyl, —$C_2$-$C_8$ alkenyl, —$C_2$-$C_8$ alkynyl, -halogen, —O—($C_1$-$C_8$ alkyl), —O—($C_2$-$C_8$ alkenyl), —O—($C_2$-$C_8$ alkynyl), -aryl, —C(O)R", —OC(O)R", —C(O)OR", —C(O)$NH_2$, —C(O)NHR", —C(O)N(R")$_2$, —NHC(O)R", —SR", —$SO_3$R", —S(O)$_2$R", —S(O)R", —OH, —$N_3$, —$NH_2$, —NH(R"), —N(R")$_2$ and —CN, where each R" is independently selected from —H, —$C_1$-$C_8$ alkyl, —$C_2$-$C_8$ alkenyl, —$C_2$-$C_8$ alkynyl, or -aryl.

Unless otherwise noted, the terms "alkenyl" and "alkynyl" refer to straight and branched carbon chains having from about 2 to about 20 carbon atoms (and all combinations and subcombinations of ranges and specific numbers of carbon atoms therein), with from about 2 to about 8 carbon atoms being preferred. An alkenyl chain has at least one double bond in the chain and an alkynyl chain has at least one triple bond in the chain. Examples of alkenyl groups include, but are not limited to, ethylene or vinyl, allyl, -1-butenyl, -2-butenyl, -isobutylenyl, -1-pentenyl, -2-pentenyl, -3-methyl-1-butenyl, -2-methyl-2-butenyl, and -2,3-dimethyl-2-butenyl. Examples of alkynyl groups include, but are not limited to, acetylenic, propargyl, acetylenyl, propynyl, -1-butynyl, -2-butynyl, -1-pentynyl, -2-pentynyl, and -3-methyl-1 butynyl.

As with alkyl groups, alkenyl and alkynyl groups, can be substituted. A "substituted" alkenyl or alkynyl group is one that is substituted with one or more groups, preferably 1 to 3 groups (and any additional substituents selected from halogen), including but not limited to, -halogen, —O—($C_1$-$C_8$ alkyl), —O—($C_2$-$C_8$ alkenyl), —O—($C_2$-$C_8$ alkynyl), -aryl, —C(O)R', —OC(O)R', —C(O)OR', —C(O)NH$_2$, —C(O)NHR', —C(O)N(R')$_2$, —NHC(O)R', —SR', —SO$_3$R', —S(O)$_2$R', —S(O)R', —OH, =O, —N$_3$, —NH$_2$, —NH(R'), —N(R')$_2$ and —CN, where each R' is independently selected from —H, —$C_1$-$C_8$ alkyl, —$C_2$-$C_8$ alkylenyl, —$C_2$-$C_8$ alkynyl, or -aryl and wherein said —O—($C_1$-$C_8$ alkyl), —O—($C_2$-$C_8$ alkenyl), —O—($C_2$-$C_8$ alkynyl), -aryl, —$C_1$-$C_8$ alkyl, —$C_2$-$C_8$ alkenyl, and —$C_2$-$C_8$ alkynyl groups can be optionally further substituted with one or more substituents including, but not limited to, —$C_1$-$C_8$ alkyl, —$C_2$-$C_8$ alkenyl, —$C_2$-$C_8$ alkynyl, -halogen, —O—($C_1$-$C_8$ alkyl), —O—($C_2$-$C_8$ alkenyl), —O—($C_2$-$C_8$ alkynyl), -aryl, —C(O)R", —OC(O)R", —C(O)OR", —C(O)NH$_2$, —C(O)NHR", —C(O)N(R")$_2$, —NHC(O)R", —SR", —SO$_3$R", —S(O)$_2$R", —S(O)R", —OH, —N$_3$, —NH$_2$, —NH(R"), —N(R")$_2$ and —CN, where each R" is independently selected from —H, —$C_1$-$C_8$ alkyl, —$C_2$-$C_8$ alkenyl, —$C_2$-$C_8$ alkynyl, or -aryl.

Unless otherwise noted, the term "alkylene" refers to a saturated branched or straight chain hydrocarbon radical having from about 1 to about 20 carbon atoms (and all combinations and subcombinations of ranges and specific numbers of carbon atoms therein), with from about 1 to about 8 carbon atoms being preferred and having two monovalent radical centers derived by the removal of two hydrogen atoms from the same or two different carbon atoms of a parent alkane. Typical alkylenes include, but are not limited to, methylene, ethylene, propylene, butylene, pentylene, hexylene, heptylene, octylene, nonylene, decalene, 1,4-cyclohexylene, and the like. Alkylene groups, whether alone or as part of another group, can be optionally substituted with one or more groups, preferably 1 to 3 groups (and any additional substituents selected from halogen), including, but not limited to, -halogen, —O—($C_1$-$C_8$ alkyl), —O—($C_2$-$C_8$ alkenyl), —O—($C_2$-$C_8$ alkynyl), -aryl, —C(O)R', —OC(O)R', —C(O)OR', —C(O)NH$_2$, —C(O)NHR', —C(O)N(R')$_2$, —NHC(O)R', —SR', —SO$_3$R', —S(O)$_2$R', —S(O)R', —OH, =O, —N$_3$, —NH$_2$, —NH(R'), —N(R')$_2$ and —CN, where each R' is independently selected from —H, —$C_1$-$C_8$ alkyl, —$C_2$-$C_8$ alkenyl, —$C_2$-$C_8$ alkynyl, or -aryl and wherein said —O—($C_1$-$C_8$ alkyl), —O—($C_2$-$C_8$ alkenyl), —O—($C_2$-$C_8$ alkynyl), -aryl, —$C_1$-$C_8$ alkyl, —$C_2$-$C_8$ alkenyl, and —$C_2$-$C_8$ alkynyl groups can be further optionally substituted with one or more substituents including, but not limited to, —$C_1$-$C_8$ alkyl, —$C_2$-$C_8$ alkenyl, —$C_2$-$C_8$ alkynyl, -halogen, —O—($C_1$-$C_8$ alkyl), —O—($C_2$-$C_8$ alkenyl), —O—($C_2$-$C_8$ alkynyl), -aryl, —C(O)R", —OC(O)R", —C(O)OR", —C(O)NH$_2$, —C(O)NHR", —C(O)N(R")$_2$, —NHC(O)R", —SR", —SO$_3$R", —S(O)$_2$R", —S(O)R", —OH, —N$_3$, —NH$_2$, —NH(R"), —N(R")$_2$ and —CN, where each R" is independently selected from —H, —$C_1$-$C_8$ alkyl, —$C_2$-$C_8$ alkenyl, —$C_2$-$C_8$ alkynyl, or -aryl.

Unless otherwise noted, the term "alkenylene" refers to an optionally substituted alkylene group containing at least one carbon-carbon double bond. Exemplary alkenylene groups include, for example, ethenylene (—CH=CH—) and propenylene (—CH=CHCH$_2$—).

Unless otherwise noted, the term "alkynylene" refers to an optionally substituted alkylene group containing at least one carbon-carbon triple bond. Exemplary alkynylene groups include, for example, acetylene (—C≡C—), propargyl (—CH$_2$C≡C—), and 4-pentynyl (—CH$_2$CH$_2$CH$_2$C≡CH—).

Unless otherwise noted, the term "aryl" refers to a monovalent aromatic hydrocarbon radical of 6-20 carbon atoms (and all combinations and subcombinations of ranges and specific numbers of carbon atoms therein) derived by the removal of one hydrogen atom from a single carbon atom of a parent aromatic ring system. Some aryl groups are represented in the exemplary structures as "Ar". Typical aryl groups include, but are not limited to, radicals derived from benzene, substituted benzene, phenyl, naphthalene, anthracene, biphenyl, and the like.

An aryl group, whether alone or as part of another group, can be optionally substituted with one or more, preferably 1 to 5, or even 1 to 2 groups including, but not limited to, -halogen, —$C_1$-$C_8$ alkyl, —$C_2$-$C_8$ alkenyl, —$C_2$-$C_8$ alkynyl, —O—($C_1$-$C_8$ alkyl), —O—($C_2$-$C_8$ alkenyl), —O—($C_2$-$C_8$ alkynyl), -aryl, —C(O)R', —OC(O)R', —C(O)OR', —C(O)NH$_2$, —C(O)NHR', —C(O)N(R')$_2$, —NHC(O)R', —SR', —SO$_3$R', —S(O)$_2$R', —S(O)R', —OH, —NO$_2$, —N$_3$, —NH$_2$, —NH(R'), —N(R')$_2$ and —CN, where each R' is independently selected from —H, —$C_1$-$C_8$ alkyl, —$C_2$-$C_8$ alkenyl, —$C_2$-$C_8$ alkynyl, or -aryl and wherein said —$C_1$-$C_8$ alkyl, —$C_2$-$C_8$ alkenyl, —$C_2$-$C_8$ alkynyl, O—($C_1$-$C_8$ alkyl), —O—($C_2$-$C_8$ alkenyl), —O—($C_2$-$C_8$ alkynyl), and -aryl groups can be further optionally substituted with one or more substituents including, but not limited to, —$C_1$-$C_8$ alkyl, —$C_2$-$C_8$ alkenyl, —$C_2$-$C_8$ alkynyl, -halogen, —O—($C_1$-$C_8$ alkyl), —O—($C_2$-$C_8$ alkenyl), —O—($C_2$-$C_8$ alkynyl), -aryl, —C(O)R", —OC(O)R", —C(O)OR", —C(O)NH$_2$, —C(O)NHR", —C(O)N(R")$_2$, —NHC(O)R", —SR", —SO$_3$R", —S(O)$_2$R", —S(O)R", —OH, —N$_3$, —NH$_2$, —NH(R"), —N(R")$_2$ and —CN, where each R" is independently selected from —H, —$C_1$-$C_8$ alkyl, —$C_2$-$C_8$ alkenyl, —$C_2$-$C_8$ alkynyl, or -aryl.

Unless otherwise noted, the term "arylene" refers to an optionally substituted aryl group which is divalent (i.e., derived by the removal of two hydrogen atoms from the same or two different carbon atoms of a parent aromatic ring system) and can be in the ortho, meta, or para configurations as shown in the following structures with phenyl as the exemplary aryl group:

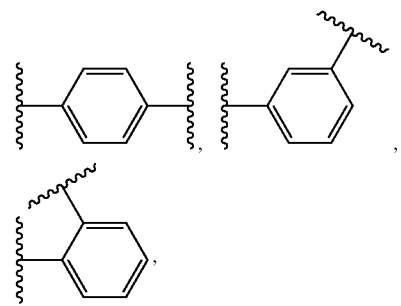

Typical "—(C$_1$-C$_8$ alkylene)aryl," "—(C$_2$-C$_8$ alkenylene) aryl", "and —(C$_2$-C$_8$ alkynylene)aryl" groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like.

Unless otherwise noted, the term "heterocycle," refers to a monocyclic, bicyclic, or polycyclic ring system having from 3 to 14 ring atoms (also referred to as ring members) wherein at least one ring atom in at least one ring is a heteroatom selected from N, O, P, or S (and all combinations and subcombinations of ranges and specific numbers of carbon atoms and heteroatoms therein). The heterocycle can have from 1 to 4 ring heteroatoms independently selected from N, O, P, or S. One or more N, C, or S atoms in a heterocycle can be oxidized. A monocyclic heterocycle preferably has 3 to 7 ring members (e.g., 2 to 6 carbon atoms and 1 to 3 heteroatoms independently selected from N, O, P, or S), and a bicyclic heterocycle preferably has 5 to 10 ring members (e.g., 4 to 9 carbon atoms and 1 to 3 heteroatoms independently selected from N, O, P, or S). The ring that includes the heteroatom can be aromatic or non-aromatic. Unless otherwise noted, the heterocycle is attached to its pendant group at any heteroatom or carbon atom that results in a stable structure.

Heterocycles are described in Paquette, "Principles of Modern Heterocyclic Chemistry" (W. A. Benjamin, New York, 1968), particularly Chapters 1, 3, 4, 6, 7, and 9; "The Chemistry of Heterocyclic Compounds, A series of Monographs" (John Wiley & Sons, New York, 1950 to present), in particular Volumes 13, 14, 16, 19, and 28; and *J. Am. Chem. Soc.* 82:5566 (1960).

Unless otherwise noted, the term "heterocyclo" refers to an optionally substituted heterocycle group as defined above that is divalent (i.e., derived by the removal of two hydrogen atoms from the same or two different carbon atoms of a parent heterocyclic ring system).

Examples of "heterocycle" groups include by way of example and not limitation pyridyl, dihydropyridyl, tetrahydropyridyl (piperidyl), thiazolyl, pyrimidinyl, furanyl, thienyl, pyrrolyl, pyrazolyl, imidazolyl, tetrazolyl, benzofuranyl, thianaphthalenyl, indolyl, indolenyl, quinolinyl, isoquinolinyl, benzimidazolyl, piperidinyl, 4-piperidonyl, pyrrolidinyl, 2-pyrrolidonyl, pyrrolinyl, tetrahydrofuranyl, bis-tetrahydrofuranyl, tetrahydropyranyl, bis-tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thienyl, thianthrenyl, pyranyl, isobenzofuranyl, chromenyl, xanthenyl, phenoxathinyl, 2H-pyrrolyl, isothiazolyl, isoxazolyl, pyrazinyl, pyridazinyl, indolizinyl, isoindolyl, 3H-indolyl, 1H-indazolyl, purinyl, 4H-quinolizinyl, phthalazinyl, naphthyridinyl, quinoxalinyl, quinazolinyl, cinnolinyl, pteridinyl, 4H-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, morpholinyl, oxazolidinyl, benzotriazolyl, benzisoxazolyl, oxindolyl, benzoxazolinyl, and isatinoyl. Preferred "heterocycle" groups include, but are not limited to, benzofuranyl, benzothiophenyl, indolyl, benzopyrazolyl, coumarinyl, isoquinolinyl, pyrrolyl, thiophenyl, furanyl, thiazolyl, imidazolyl, pyrazolyl, triazolyl, quinolinyl, pyrimidinyl, pyridinyl, pyridonyl, pyrazinyl, pyridazinyl, isothiazolyl, isoxazolyl and tetrazolyl.

A heterocycle group, whether alone or as part of another group, can be optionally substituted with one or more groups, preferably 1 to 2 groups, including but not limited to, —C$_1$-C$_8$ alkyl, —C$_2$-C$_8$ alkenyl, —C$_2$-C$_8$ alkynyl, -halogen, —O—(C$_1$-C$_8$alkyl), —O—(C$_2$-C$_8$ alkenyl), —O—(C$_2$-C$_8$ alkynyl), -aryl, —C(O)R', —OC(O)R', —C(O)OR', —C(O)NH$_2$, —C(O)NHR', —C(O)N(R')$_2$, —NHC(O)R', —SR', —SO$_3$R', —S(O)$_2$R', —S(O)R', —OH, —N$_3$, —NH$_2$, —NH(R'), —N(R')$_2$ and —CN, where each R' is independently selected from —H, —C$_1$-C$_8$ alkyl, —C$_2$-C$_8$ alkenyl, —C$_2$-C$_8$ alkynyl, or -aryl and wherein said —O—(C$_1$-C$_8$ alkyl), —O—(C$_2$-C$_8$ alkenyl), —O—(C$_2$-C$_8$ alkynyl), —C$_1$-C$_8$ alkyl, —C$_2$-C$_8$ alkenyl, —C$_2$-C$_8$ alkynyl, and -aryl groups can be further optionally substituted with one or more substituents including, but not limited to, —C$_1$-C$_8$ alkyl, —C$_2$-C$_8$ alkenyl, —C$_2$-C$_8$ alkynyl, -halogen, —O—(C$_1$-C$_8$ alkyl), —O—(C$_2$-C$_8$ alkenyl), —O—(C$_2$-C$_8$ alkynyl), -aryl, —C(O)R", —OC(O)R", —C(O)OR", —C(O)NH$_2$, —C(O)NHR", —C(O)N(R")$_2$, —NHC(O)R", —SR", —SO$_3$R", —S(O)$_2$R", —S(O)R", —OH, —N$_3$, —NH$_2$, —NH(R"), —N(R")$_2$ and —CN, where each R" is independently selected from —H, —C$_1$-C$_8$ alkyl, —C$_2$-C$_8$ alkenyl, —C$_2$-C$_8$ alkynyl, or aryl.

By way of example and not limitation, carbon-bonded heterocycles can be bonded at the following positions: position 2, 3, 4, 5, or 6 of a pyridine; position 3, 4, 5, or 6 of a pyridazine; position 2, 4, 5, or 6 of a pyrimidine; position 2, 3, 5, or 6 of a pyrazine; position 2, 3, 4, or 5 of a furan, tetrahydrofuran, thiofuran, thiophene, pyrrole or tetrahydropyrrole; position 2, 4, or 5 of an oxazole, imidazole or thiazole; position 3, 4, or 5 of an isoxazole, pyrazole, or isothiazole; position 2 or 3 of an aziridine; position 2, 3, or 4 of an azetidine; position 2, 3, 4, 5, 6, 7, or 8 of a quinoline; or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

By way of example and not limitation, nitrogen bonded heterocycles can be bonded at position 1 of an aziridine, azetidine, pyrrole, pyrrolidine, 2-pyrroline, 3-pyrroline, imidazole, imidazolidine, 2-imidazoline, 3-imidazoline, pyrazole, pyrazoline, 2-pyrazoline, 3-pyrazoline, piperidine, piperazine, indole, indoline, or 1H-indazole; position 2 of a isoindole, or isoindoline; position 4 of a morpholine; and position 9 of a carbazole, or β-carboline. Still more typically, nitrogen bonded heterocycles include 1-aziridyl, 1-azetedyl, 1-pyrrolyl, 1-imidazolyl, 1-pyrazolyl, and 1-piperidinyl.

Unless otherwise noted, the term "carbocycle," refers to a saturated or unsaturated non-aromatic monocyclic, bicyclic, or polycyclic ring system having from 3 to 14 ring atoms (and all combinations and subcombinations of ranges and specific numbers of carbon atoms therein) wherein all of the ring atoms are carbon atoms. Monocyclic carbocycles preferably have 3 to 6 ring atoms, still more preferably 5 or 6 ring atoms. Bicyclic carbocycles preferably have 7 to 12 ring atoms, e.g., arranged as a bicyclo [4,5], [5,5], [5,6] or [6,6] system, or 9 or 10 ring atoms arranged as a bicyclo [5,6] or [6,6] system. The term "carbocycle" includes, for example, a monocyclic carbocycle ring fused to an aryl ring (e.g., a monocyclic carbocycle ring fused to a benzene ring). Carbocycles preferably have 3 to 8 carbon ring atoms.

Carbocycle groups, whether alone or as part of another group, can be optionally substituted with, for example, one or more groups, preferably 1 or 2 groups (and any additional substituents selected from halogen), including, but not limited to, -halogen, —$C_1$-$C_8$ alkyl, —$C_2$-$C_8$ alkenyl, —$C_2$-$C_8$ alkynyl, —O—($C_1$-$C_8$ alkyl), —O—($C_2$-$C_8$ alkenyl), —O—($C_2$-$C_8$ alkynyl), -aryl, —C(O)R', —OC(O)R', —C(O)OR', —C(O)NH$_2$, —C(O)NHR', —C(O)N(R')$_2$, —NHC(O)R', —SR', —SO$_3$R', —S(O)$_2$R', —S(O)R', —OH, =O, —N$_3$, —NH$_2$, —NH(R'), —N(R')$_2$ and —CN, where each R' is independently selected from —H, —$C_1$-$C_8$ alkyl, —$C_2$-$C_8$ alkenyl, —$C_2$-$C_8$ alkynyl, or -aryl and wherein said —$C_1$-$C_8$ alkyl, —$C_2$-$C_8$ alkenyl, —$C_2$-$C_8$ alkynyl, —O—($C_1$-$C_8$ alkyl), —O—($C_2$-$C_8$ alkenyl), —O—($C_2$-$C_8$ alkynyl), and -aryl groups can be further optionally substituted with one or more substituents including, but not limited to, —$C_1$-$C_8$ alkyl, —$C_2$-$C_8$ alkenyl, —$C_2$-$C_8$ alkynyl, -halogen, —O—($C_1$-$C_8$ alkyl), —O—($C_2$-$C_8$ alkenyl), —O—($C_2$-$C_8$ alkynyl), -aryl, —C(O)R", —OC(O)R", —C(O)OR", —C(O)NH$_2$, —C(O)NHR", —C(O)N(R")$_2$, —NHC(O)R", —SR", —SO$_3$R", —S(O)$_2$R", —S(O)R", —OH, —N$_3$, —NH$_2$, —NH(R"), —N(R")$_2$ and —CN, where each R" is independently selected from —H, —$C_1$-$C_8$ alkyl, —$C_2$-$C_8$ alkenyl, —$C_2$-$C_8$ alkynyl, or -aryl. Examples of monocyclic carbocylic substituents include -cyclopropyl, -cyclobutyl, -cyclopentyl, -1-cyclopent-1-enyl, -1-cyclopent-2-enyl, -1-cyclopent-3-enyl, cyclohexyl, -1-cyclohex-1-enyl, -1-cyclohex-2-enyl, -1-cyclohex-3-enyl, -cycloheptyl, -cyclooctyl, -1,3-cyclohexadienyl, -1,4-cyclohexadienyl, -1,3-cycloheptadienyl, -1,3,5-cycloheptatrienyl, and -cyclooctadienyl.

A "carbocyclo," whether used alone or as part of another group, refers to an optionally substituted carbocycle group as defined above that is divalent (i.e., derived by the removal of two hydrogen atoms from the same or two different carbon atoms of a parent carbocyclic ring system).

Unless otherwise indicated by context, a hyphen (-) designates the point of attachment to the pendant molecule. Accordingly, the term "—($C_1$-$C_8$ alkylene)aryl" or "—$C_1$-$C_8$ alkylene(aryl)" refers to a $C_1$-$C_8$ alkylene radical as defined herein wherein the alkylene radical is attached to the pendant molecule at any of the carbon atoms of the alkylene radical and one of the hydrogen atoms bonded to a carbon atom of the alkylene radical is replaced with an aryl radical as defined herein.

When a particular group is "substituted", that group may have one or more substituents, preferably from one to five substituents, more preferably from one to three substituents, most preferably from one to two substituents, independently selected from the list of substituents. The group can, however, generally have any number of substituents selected from halogen. Groups that are substituted are so indicated.

It is intended that the definition of any substituent or variable at a particular location in a molecule be independent of its definitions elsewhere in that molecule. It is understood that substituents and substitution patterns on the compounds described herein can be selected by one of ordinary skill in the art to provide compounds that are chemically stable and that can be readily synthesized by techniques known in the art as well as those methods set forth herein.

Protective groups as used herein refer to groups which selectively block, either temporarily or permanently, one reactive site in a multifunctional compound. Suitable hydroxy-protecting groups for use in the compounds described herein are pharmaceutically acceptable and may or may not need to be cleaved from the parent compound after administration to a subject in order for the compound to be active. Cleavage is through normal metabolic processes within the body. Hydroxy protecting groups are well known in the art, see, PROTECTIVE GROUPS IN ORGANIC SYNTHESIS by T. W. Greene and P. G. M. Wuts (John Wiley & sons, 3$^{rd}$ Edition) incorporated herein by reference in its entirety and for all purposes and include, for example, ether (e.g., alkyl ethers and silyl ethers including, for example, dialkylsilylether, trialkylsilylether, dialkylalkoxysilylether), ester, carbonate, carbamates, sulfonate, and phosphate protecting groups. Examples of hydroxy protecting groups include, but are not limited to, methyl ether; methoxymethyl ether, methylthiomethyl ether, (phenyldimethylsilyl)methoxymethyl ether, benzyloxymethyl ether, p-methoxybenzyloxymethyl ether, p-nitrobenzyloxymethyl ether, o-nitrobenzyloxymethyl ether, (4-methoxyphenoxy)methyl ether, guaiacolmethyl ether, t-butoxymethyl ether, 4-pentenyloxymethyl ether, siloxymethyl ether, 2-methoxyethoxymethyl ether, 2,2,2-trichloroethoxymethyl ether, bis(2-chloroethoxy)methyl ether, 2-(trimethylsilyl)ethoxymethyl ether, menthoxymethyl ether, tetrahydropyranyl ether, 1-methoxycylcohexyl ether, 4-methoxytetrahydrothiopyranyl ether, 4-methoxytetrahydrothiopyranyl ether S,S-Dioxide, 1-[(2-choro-4-methyl)phenyl]-4-methoxypiperidin-4-yl ether, 1-(2-fluorophenyl)-4-methoxypiperidin-4-yl ether, 1,4-dioxan-2-yl ether, tetrahydrofuranyl ether, tetrahydrothiofuranyl ether; substituted ethyl ethers such as 1-ethoxyethyl ether, 1-(2-chloroethoxy)ethyl ether, 1-[2-(trimethylsilyl)ethoxy]ethyl ether, 1-methyl-1-methoxyethyl ether, 1-methyl-1-benzyloxyethyl ether, 1-methyl-1-benzyloxy-2-fluoroethyl ether, 1-methyl-1phenoxyethyl ether, 2-trimethylsilyl ether, t-butyl ether, allyl ether, propargyl ethers, p-chlorophenyl ether, p-methoxyphenyl ether, benzyl ether, p-methoxybenzyl ether 3,4-dimethoxybenzyl ether, trimethylsilyl ether, triethylsilyl ether, tripropylsilylether, dimethylisopropylsilyl ether, diethylisopropylsilyl ether, dimethylhexylsilyl ether, t-butyldimethylsilyl ether, diphenylmethylsilyl ether, benzoylformate ester, acetate ester, chloroacetate ester, dichloroacetate ester, trichloroacetate ester, trifluoroacetate ester, methoxyacetate ester, triphenylmethoxyacetate ester, phenylacetate ester, benzoate ester, alkyl methyl carbonate, alkyl 9-fluorenylmethyl carbonate, alkyl ethyl carbonate, alkyl 2,2,2-trichloroethyl carbonate, 1,1-dimethyl-2,2,2-trichloroethyl carbonate, alkylsulfonate, methanesulfonate, benzylsulfonate, tosylate, methylene acetal, ethylidene acetal, and t-butylmethylidene ketal. Preferred protecting groups are represented by the formulas —R, —Si(R)(R)(R), —C(O)R, —C(O)OR, —C(O)NH(R), —S(O)$_2$R, —S(O)$_2$OH, P(O)(OH)$_2$, and —P(O)(OH)OR, wherein R is $C_1$-$C_{20}$ alkyl, $C_2$-$C_{20}$ alkenyl, $C_2$-$C_{20}$ alkynyl, —$C_1$-$C_{20}$ alkylene(carbocycle), —$C_2$-$C_{20}$ alkenylene(carbocycle), —$C_2$-$C_{20}$ alkynylene(carbocycle), —$C_6$-$C_{10}$ aryl, —$C_1$-$C_{20}$ alkylene(aryl), —$C_2$-$C_{20}$ alkenylene(aryl), —$C_2$-$C_{20}$ alkynylene(aryl), —$C_1$-$C_{20}$ alkylene(heterocycle), —$C_2$-$C_{20}$ alkenylene(heterocycle), or —$C_2$-$C_{20}$ alkynylene(heterocycle) wherein said alkyl, alkenyl, alkynyl, alkylene, alkenylene, alkynylene, aryl, carbocycle, and heterocycle radicals whether alone or as part of another group are optionally substituted.

The abbreviation "MMAE" refers to monomethyl auristatin E.

The abbreviation "MMAF" refers to dovaline-valine-dolaisoleuine-dolaproine-phenylalanine.

The abbreviation "cAC10-vcE" as used herein refers to a vc-MMAE (also known as mc-vc-MMAE) antibody drug conjugate wherein the antibody is a chimeric AC10 antibody. In an exemplary embodiment, the chimeric AC10 antibody has a heavy chain variable region having the amino acid sequence set forth in SEQ ID NO:1, a light chain variable region having the amino acid sequence set forth in SEQ ID NO:2, a human gamma I constant region having the amino acid sequence set forth in SEQ ID NO:11 and a human kappa constant region having the amino acid sequence set forth in SEQ ID NO:12. Exemplary cAC10-vcE compositions have an average of about 3 to about 5 drugs per antibody and the drugs are attached to the antibody via thioether bonds. Brentuximab vedotin is the USAN name for a cAC10-vcE conjugate that is in clinical trials (Seattle Genetics).

The abbreviation "h1F6-mcF" refers to a mc-MMAF antibody drug conjugate wherein the antibody is a humanized 1F6 antibody. In an exemplary embodiment, the h1F6 antibody has a heavy chain variable region having the amino acid sequence set forth in SEQ ID NO:5, a light chain variable region having the amino acid sequence set forth in SEQ ID NO:6, a human gamma I constant region having the amino acid sequence set forth in SEQ ID NO:11 and a human kappa constant region having the amino acid sequence set forth in SEQ ID NO:12. Exemplary h1F6-mcF compositions have an average of about 3 to about 5 drugs per antibody and the drugs are attached to the antibody via thioether bonds. SGN-75 is a h1F6-mcF conjugate that is in clinical trials (Seattle Genetics).

The abbreviation "hBU12-mcF" refers to a mc-MMAF antibody drug conjugate wherein the antibody is a humanized BU12 antibody. In an exemplary embodiment, the hBU12 antibody has a heavy chain variable region having the amino acid sequence set forth in SEQ ID NO:9, a light chain variable region having the amino acid sequence set forth in SEQ ID NO:10, a human gamma I constant region having the amino acid sequence set forth in SEQ ID NO:11 and a human kappa constant region having the amino acid sequence set forth in SEQ ID NO:12. Exemplary hBU12-mcF compositions have an average of about 3 to about 5 drugs per antibody and the drugs are attached to the antibody via thioether bonds. SGN-19A is a hBU12-mcF conjugate that is in preclinical programs (Seattle Genetics).

The term "specifically binds" means that the binding agent, e.g., antibody will react, in a highly selective manner, with its corresponding antigen and not with the multitude of other antigens.

The term "inhibitor" as used herein refers to a molecule having the ability to inhibit a biological function of a target polypeptide. The term "selective inhibition" or "selectively inhibit" refers to the agent's ability to preferentially reduce the target signaling activity as compared to off-target signaling activity, via direct or indirect interaction with the target.

The term "antibody" refers to (a) immunoglobulin polypeptides and immunologically active portions of immunoglobulin polypeptides, i.e., polypeptides of the immunoglobulin family, or fragments thereof, that contain an antigen binding site that specifically binds to a specific antigen, or (b) conservatively substituted derivatives of such immunoglobulin polypeptides or fragments that specifically bind to the antigen. Examples of antibody fragments include, but are not limited to, a Fab, Fab', F(ab')2, Fd, Fv, scFv and scFv-Fc fragment, diabody, triabody, tetrabody, linear antibody, single-chain antibody, and other multispecific antibodies formed from antibody fragments. (See Holliger and Hudson, 2005, Nat. Biotechnol. 23:1126-1136.) The immunoglobulin molecules can be of any type (e.g., IgG, IgE, IgM, IgD, IgA and IgY), class (e.g., IgG1, IgG2, IgG3, IgG4, IgA1 and IgA2) or subclass of immunoglobulin molecule. Included in the term immunoglobulin are those immunoglobulin molecules that have modifications in the constant region, including modification (e.g., substitutions, deletions or additions) in amino acid residues that interact with Fcγ receptors. Antibodies are generally described in, for example, Harlow & Lane, Antibodies: *A Laboratory Manual* (Cold Spring Harbor Laboratory Press, 1988). Unless otherwise apparent from the context reference to an antibody also includes antibody derivatives.

An "antibody derivative" means an antibody, as defined above, that is modified by covalent attachment of a heterologous molecule such as, e.g., by attachment of a heterologous polypeptide, or by glycosylation, deglycosylation, acetylation or phosphorylation not normally associated with the antibody, and the like.

Antibodies employed in the methods and compositions described herein are preferably monoclonal, and may be multispecific, human, humanized or chimeric antibodies, single chain antibodies, Fab fragments, F(ab') fragments, fragments produced by a Fab expression library, and binding fragments of any of the above, provided that they can be conjugated to an auristatin drug either directly or indirectly via a linker.

The term "monoclonal antibody" (mAb) refers to an antibody obtained from a population of substantially homogeneous antibodies; that is, the individual antibodies comprising the population are identical except for naturally occurring mutations that may be present in minor amounts. Monoclonal antibodies are highly specific, being directed against a single antigenic determinant, also referred to as an epitope. The modifier "monoclonal" is indicative of a substantially homogeneous population of antibodies directed to the identical epitope and is not to be construed as requiring production of the antibody by any particular method. Monoclonal antibodies can be made by any technique or methodology known in the art; for example, the hybridoma method first described by Kohler et al., 1975, Nature 256: 495, or recombinant DNA methods known in the art (see, e.g., U.S. Pat. No. 4,816,567). In another example, monoclonal antibodies can also be isolated from phage antibody libraries, using techniques described in Clackson et al., 1991, Nature 352: 624-628, and Marks et al., 1991, J. Mol. Biol. 222:581-597. In contrast, the antibodies in a preparation of polyclonal antibodies are typically a heterogeneous population of immunoglobulin isotypes and/or classes and also exhibit a variety of epitope specificity.

"Cytotoxic effect," in reference to the effect of an agent on a cell, means killing of the cell. "Cytostatic effect" means an inhibition of cell proliferation. A "cytotoxic agent" means an agent that has a cytotoxic or cytostatic effect on a cell, thereby depleting or inhibiting the growth of, respectively, cells within a cell population.

The term "subject" or "patient" for purposes of treatment refers to any animal, particularly an animal classified as a mammal, including humans, domesticated and farm animals, and zoo, sports, or pet animals, such as dogs, horses, cats, cows, and the like. Preferably, the subject is human.

The terms "treatment" and "therapy", and the like, as used herein, refer to slowing, stopping, or reversing the progression of cancer in a subject. Treatment can be evidenced by the inhibition of tumor growth, the arrest of tumor growth, the regression of already existing tumors, or increased survival.

The term "therapeutically effective amount" or "effective amount" refers to the amount of one or more agents or compositions as described herein that is sufficient to slow, stop, or reverse the progression of cancer in a subject or increase survival of the patient. The therapeutically effective amount may refer to a target serum concentration that has been shown to be effective in, for example, slowing disease progression. When the term "therapeutically effective amount" is used to refer to combination therapy, it refers to the amount of the combination of agents taken together so that the combined effect elicits the desired biological or medicinal response. Efficacy can be measured in conventional ways, depending on the condition to be treated. For example, in neoplastic diseases, efficacy can be measured by assessing the time to disease progression (TTP), or determining the response rates (RR).

The term "pharmaceutically acceptable" as used herein means approved by a regulatory agency of the Federal or a state government or listed in the U.S. Pharmacopeia or other generally recognized pharmacopeia for use in animals, and more particularly in humans. The term "pharmaceutically compatible ingredient" refers to a pharmaceutically acceptable diluent, adjuvant, excipient, or vehicle with which an agent or composition is administered.

Antibody Drug Conjugate

The methods described herein encompass the use of antibody drug conjugates in combination therapy for the killing of tumor cells and/or inhibition of proliferation of tumor cells. The methods described herein encompass the use of antibody drug conjugates in combination therapy for the treatment of cancer. The antibody-drug conjugates comprise an antibody as the Ligand unit and an auristatin as the Drug unit. The antibody is one that specifically binds to a cancer cell antigen which is on the surface of a cancer cell. The antibody drug conjugates have potent cytotoxic and/or cytostatic activity against cells expressing the cancer cell antigen to which the antibody specifically binds. The Drug units are covalently linked to the antibody via a Linker unit (-LU-).

In some embodiments, the Antibody Drug Conjugate has the following formula:

$$L\text{-}(LU\text{-}D)_p \qquad (I)$$

or a pharmaceutically acceptable salt thereof; wherein:
L is the Ligand unit and is an antibody that specifically binds to a cancer cell antigen which is on the surface of a cancer cell,
(LU-D) is a Linker unit-Drug unit moiety, wherein:
LU- is a Linker unit, and
-D is an auristatin drug having cytostatic or cytotoxic activity against a target cell; and
p is from 1 to 20.

In some embodiments, p ranges from 1 to 10, 1 to 9, 1 to 8, 1 to 7, 1 to 6, 1 to 5, 1 to 4, 1 to 3, or 1 to 2. In some embodiments, p ranges from 2 to 10, 2 to 9, 2 to 8, 2 to 7, 2 to 6, 2 to 5, 2 to 4 or 2 to 3. In other embodiments, p is 1, 2, 3, 4, 5 or 6.

In some embodiments, the Antibody Drug Conjugate has the following formula:

$$L\text{-}(A_a\text{-}W_w\text{—}Y_y\text{-}D)_p \qquad (II)$$

or a pharmaceutically acceptable salt thereof;
wherein:
L is the Ligand unit and is an antibody that specifically binds to a cancer cell antigen which is on the surface of a cancer cell
-$A_a$-$W_w$—$Y_y$— is a Linker unit (LU), wherein:
-A- is a Stretcher unit,
a is 0 or 1,
each —W— is independently an Amino Acid unit,
w is an integer ranging from 0 to 12,
—Y— is a Spacer unit (e.g., a self-immolative spacer unit),
y is 0, 1 or 2;
-D is an auristatin drug unit having cytostatic or cytotoxic activity against the target cell; and
p is from 1 to 20.

In some embodiments, a is 0 or 1, w is 0 or 1, and y is 0, 1 or 2. In some embodiments, a is 0 or 1, w is 0 or 1, and y is 0 or 1. In some embodiments, p ranges from 1 to 10, 1 to 9, 1 to 8, 1 to 7, 1 to 6, 1 to 5, 1 to 4, 1 to 3, or 1 to 2. In some embodiments, p ranges from 2 to 10, 2 to 9, 2 to 8, 2 to 7, 2 to 6, 2 to 5, 2 to 4 or 2 to 3. In other embodiments, p is 1, 2, 3, 4, 5 or 6. In some embodiments, when w is not zero, y is 1 or 2. In some embodiments, when w is 1 to 12, y is 1 or 2. In some embodiments, w is 2 to 12 and y is 1 or 2. In some embodiments, a is 1 and w and y are 0.

In compositions comprising a plurality of Antibody Drug Conjugates, p is the average number of Drug molecules per Ligand, also referred to as the average drug loading. Average drug loading may range from 1 to about 20 drugs (D) per Ligand. In some embodiments when p represents the average drug loading, p is about 1, about 2, about 3, about, 4, about 5 or about 6. In preferred embodiments, when p represents the average drug loading, p is from about 2 to about 6, or from about 3 to about 5. The average number of drugs per ligand in preparation of conjugation reactions may be characterized by conventional means such as mass spectroscopy, ELISA assay, and HPLC. The quantitative distribution of Antibody Drug Conjugates in terms of p may also be determined. In some instances, separation, purification, and characterization of homogeneous Antibody Drug Conjugates where p is a certain value from Antibody Drug Conjugates with other drug loadings may be achieved by means such as reverse phase HPLC or electrophoresis. In exemplary embodiments, p is from 2 to about 8.

The generation of Antibody Drug Conjugates can be accomplished by any technique known to the skilled artisan. Briefly, the Antibody Drug Conjugates comprise an antibody as the Ligand unit, a drug, and optionally a linker that joins the drug and the binding agent. A number of different reactions are available for covalent attachment of drugs and/or linkers to antibodies. This is often accomplished by reaction of the amino acid residues of the antibody molecule, including the amine groups of lysine, the free carboxylic acid groups of glutamic and aspartic acid, the sulfhydryl groups of cysteine and the various moieties of the aromatic amino acids. One of the most commonly used non-specific methods of covalent attachment is the carbodiimide reaction to link a carboxy (or amino) group of a compound to amino (or carboxy) groups of the antibody. Additionally, bifunctional agents such as dialdehydes or imidoesters have been used to link the amino group of a compound to amino groups of an antibody molecule. Also available for attachment of drugs to binding agents is the Schiff base reaction. This method involves the periodate oxidation of a drug that contains glycol or hydroxy groups, thus forming an aldehyde which is then reacted with the binding agent. Attachment occurs via formation of a Schiff base with amino groups of the binding agent. Isothiocyanates can also be used as coupling agents for covalently attaching drugs to binding agents. Other techniques are known to the skilled artisan.

In certain embodiments, an intermediate, which is the precursor of the linker, is reacted with the drug under appropriate conditions. In certain embodiments, reactive groups are used on the drug and/or the intermediate. The product of the reaction between the drug and the intermediate, or the derivatized drug, is subsequently reacted with the antibody under appropriate conditions.

Linker Units

Typically, the Antibody Drug Conjugates comprise a linker region between the drug unit and the Ligand unit. In some embodiments, the linker is cleavable under intracellular conditions, such that cleavage of the linker releases the drug unit from the ligand in the intracellular environment. In yet other embodiments, the linker unit is not cleavable and the drug is released, for example, by antibody degradation.

In some embodiments, the linker is cleavable by a cleaving agent that is present in the intracellular environment (e.g., within a lysosome or endosome or caveolea). The linker can be, e.g., a peptidyl linker that is cleaved by an intracellular peptidase or protease enzyme, including, but not limited to, a lysosomal or endosomal protease. In some embodiments, the peptidyl linker is at least two amino acids long or at least three amino acids long. Cleaving agents can include cathepsins B and D and plasmin, all of which are known to cleave dipeptide drug derivatives resulting in the release of active drug inside target cells (see, e.g., Dubowchik and Walker, 1999, *Pharm. Therapeutics* 83:67-123). Most typical are peptidyl linkers that are cleavable by enzymes that are present in the target cancer cells. For example, a peptidyl linker that is cleavable by the thiol-dependent protease cathepsin-B, which is highly expressed in cancerous tissue, can be used (e.g., a Phe-Leu or a Gly-Phe-Leu-Gly linker). Other examples of such linkers are described, e.g., in U.S. Pat. No. 6,214,345 or U.S. Pat. No. 7,659,241, each of which is incorporated herein by reference in its entirety and for all purposes. In a specific embodiment, the peptidyl linker cleavable by an intracellular protease is a Val-Cit linker or a Phe-Lys linker (see, e.g., U.S. Pat. No. 6,214,345, which describes the synthesis of doxorubicin with the val-cit linker). One advantage of using intracellular proteolytic release of the therapeutic agent is that the agent is typically attenuated when conjugated and the serum stabilities of the conjugates are typically high.

In yet other embodiments, the linker is cleavable under reducing conditions (e.g., a disulfide linker). A variety of disulfide linkers are known in the art, including, for example, those that can be formed using SATA (N-succinimidyl-S-acetylthioacetate), SPDP (N-succinimidyl-3-(2-pyridyldithio)propionate), SPDB (N-succinimidyl-3-(2-pyridyldithio)butyrate) and SMPT (N-succinimidyl-oxycarbonyl-alpha-methyl-alpha-(2-pyridyl-dithio) toluene), SPDB and SMPT (See, e.g., Thorpe et al., 1987, *Cancer Res.* 47:5924-5931; Wawrzynczak et al., In *Immunoconjugates: Antibody Conjugates in Radioimagery and Therapy of Cancer* (C. W. Vogel ed., Oxford U. Press, 1987. See also U.S. Pat. No. 4,880,935.)

In yet other specific embodiments, the linker is a malonate linker (Johnson et al., 1995, *Anticancer Res.* 15:1387-93), a maleimidobenzoyl linker (Lau et al., 1995, *Bioorg-Med-Chem.* 3(10):1299-1304), or a 3'-N-amide analog (Lau et al., 1995, *Bioorg-Med-Chem.* 3(10):1305-12).

In yet other embodiments, the linker unit is not cleavable and the drug is released by antibody degradation. (See for example U.S. Pat. No. 7,498,298 incorporated by reference herein in its entirety and for all purposes).

In one aspect, the linker is not substantially sensitive to the extracellular environment. As used herein, "not substantially sensitive to the extracellular environment," in the context of a linker, means that no more than about 20%, typically no more than about 15%, more typically no more than about 10%, and even more typically no more than about 5%, no more than about 3%, or no more than about 1% of the linkers, in a sample of Antibody Drug Conjugate, are cleaved when the Antibody Drug Conjugate presents in an extracellular environment (e.g., in plasma). Whether a linker is not substantially sensitive to the extracellular environment can be determined, for example, by incubating with plasma the Antibody Drug Conjugate for a predetermined time period (e.g., 2, 4, 8, 16, or 24 hours) and then quantitating the amount of free drug present in the plasma.

In other, non-mutually exclusive embodiments, the linker promotes cellular internalization. In certain embodiments, the linker promotes cellular internalization when conjugated to the therapeutic agent (i.e., in the milieu of the linker-therapeutic agent moiety of the Antibody Drug Conjugate as described herein). In yet other embodiments, the linker promotes cellular internalization when conjugated to both the auristatin compound and the antibody.

The synthesis and structure of exemplary linker units, stretcher units, amino acid units, self-immolative spacer unit, and drug units that can be used with the present compositions and methods are described in WO 2004010957, U.S. Publication No. 20060074008, U.S. Publication No. 20050238649, U.S. Publication No. 20060024317, and U.S. Publication No. 20090010945 (each of which is incorporated by reference herein in its entirety and for all purposes).

A "Linker unit" (LU) is a bifunctional compound that can be used to link a Drug unit and a Ligand unit to form an Antibody Drug Conjugate. In some embodiments, the Linker unit has the formula:

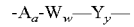

wherein: -A- is a Stretcher unit,
a is 0 or 1,
each —W— is independently an Amino Acid unit,
w is an integer ranging from 0 to 12,
—Y— is a Spacer unit (e.g., a self-immolative Spacer unit), and
y is 0, 1 or 2.

In some embodiments, a is 0 or 1, w is 0 or 1, and y is 0, 1 or 2. In some embodiments, a is 0 or 1, w is 0 or 1, and y is 0 or 1. In some embodiments, when w is 1 to 12, y is 1 or 2. In some embodiments, w is 2 to 12 and y is 1 or 2. In some embodiments, a is 1 and w and y are 0.

The Stretcher Unit

The Stretcher unit (A), when present, is capable of linking a Ligand unit (e.g., an antibody) to an Amino Acid unit (—W—), if present, to a Spacer unit (—Y—), if present; or to a Drug unit (-D). Useful functional groups that can be present on an antibody either naturally or via chemical manipulation include, but are not limited to, sulfhydryl, amino, hydroxyl, the anomeric hydroxyl group of a carbohydrate, and carboxyl. Suitable functional groups are sulfhydryl and amino. In one example, sulfhydryl groups can be generated by reduction of the intramolecular disulfide bonds of an antibody. In another embodiment, sulfhydryl groups can be generated by reaction of an amino group of a lysine moiety of an antibody with 2-iminothiolane (Traut's reagent) or other sulfhydryl generating reagents. In certain embodiments, the antibody is a recombinant antibody and is engineered to carry one or more lysines. In certain other embodiments, the recombinant antibody is engineered to carry additional sulfhydryl groups, e.g., additional cysteines.

In one embodiment, the Stretcher unit forms a bond with a sulfur atom of the Ligand unit. The sulfur atom can be derived from a sulfhydryl group of a Ligand. Representative Stretcher units of this embodiment are depicted within the square brackets of Formulas IIIa and IIIb, wherein L-, —W—, —Y—, -D, w and y are as defined above, and $R^a$ is selected from —$C_1$-$C_{10}$ alkylene-, —$C_2$-$C_{10}$ alkenylene-, —$C_2$-$C_{10}$ alkynylene-, -carbocyclo-, —O—($C_1$-$C_8$ alkylene)-, O—($C_2$-$C_8$ alkenylene)-, —O—($C_2$-$C_8$ alkynylene)-, -arylene-, —$C_1$-$C_{10}$ alkylene-arylene-, —$C_2$-$C_{10}$ alkenylene-arylene, —$C_2$-$C_{10}$ alkynylene-arylene, -arylene-$C_1$-

$C_{10}$ alkylene-, -arylene-$C_2$-$C_{10}$ alkenylene-, -arylene-$C_2$-$C_{10}$ alkynylene-, alkylene-(carbocyclo)-, —$C_2$-$C_{10}$ alkenylene-(carbocyclo)-, —$C_2$-$C_{10}$ alkynylene-(carbocyclo)-, -(carbocyclo)-$C_1$-$C_{10}$ alkylene-, -(carbocyclo)-$C_2$-$C_{10}$ alkenylene-, -(carbocyclo)-$C_2$-$C_{10}$ alkynylene, heterocyclo-, —$C_1$-$C_{10}$ alkylene-(heterocyclo)-, —$C_2$-$C_{10}$ alkenylene-(heterocyclo)-, —$C_2$-$C_{10}$ alkynylene-(heterocyclo)-, -(heterocyclo)-$C_1$-$C_{10}$ alkylene-, -(heterocyclo)-$C_2$-$C_{10}$ alkenylene-, -(heterocyclo)-$C_2$-$C_{10}$ alkynylene-, —$(CH_2CH_2O)_r$-, or —$(CH_2CH_2O)_r$—$CH_2$—, and r is an integer ranging from 1-10, wherein said alkyl, alkenyl, alkynyl, alkylene, alkenylene, alkynylene, aryl, carbocycle, carbocyclo, heterocyclo, and arylene radicals, whether alone or as part of another group, are optionally substituted. In some embodiments, said alkyl, alkenyl, alkynyl, alkylene, alkenylene, alkynylene, aryl, carbocycle, carbocyclo, heterocyclo, and arylene radicals, whether alone or as part of another group, are unsubstituted. In some embodiments, $R^a$ is selected from —$C_1$-$C_{10}$ alkylene-, -carbocyclo-, —O—($C_1$-$C_8$ alkylene)-, -arylene-, —$C_1$-$C_{10}$ alkylene-arylene-, -arylene-$C_1$-$C_{10}$ alkylene-, —$C_1$-$C_{10}$ alkylene-(carbocyclo)-, -(carbocyclo)-$C_1$-$C_{10}$ alkylene-, —$C_3$-$C_8$ heterocyclo-, —$C_1$-$C_{10}$ alkylene-(heterocyclo)-, -(heterocyclo)-$C_1$-$C_{10}$ alkylene-, —$(CH_2CH_2O)_r$—, and —$(CH_2CH_2O)_r$—$CH_2$—; and r is an integer ranging from 1-10, wherein said alkylene groups are unsubstituted and the remainder of the groups are optionally substituted.

It is to be understood from all the exemplary embodiments that even where not denoted expressly, from 1 to 20 drug moieties or drug-linker moieties can be linked to a Ligand (p=1-20).

IIIa

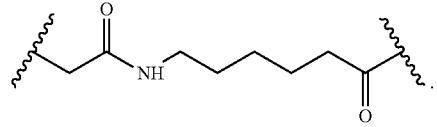

IIIb

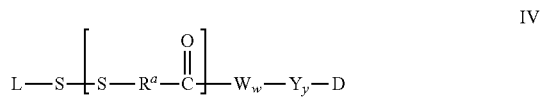

An illustrative Stretcher unit is that of Formula IIIa wherein $R^a$ is —$(CH_2)_5$—:

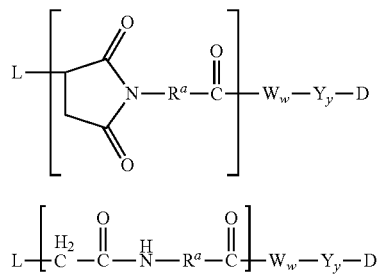

Another illustrative Stretcher unit is that of Formula IIIa wherein $R^a$ is —$(CH_2CH_2O)_r$—$CH_2$—; and r is 2:

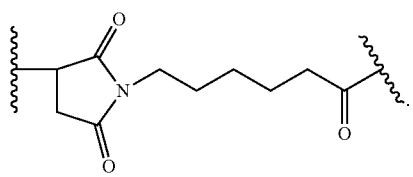 [SMILES: *C(=O)CCCCCN1C(=O)CC(*)C1=O]

An illustrative Stretcher unit is that of Formula IIIa wherein $R^a$ is -arylene- or arylene-$C_1$-$C_{10}$ alkylene-. In some embodiments, the aryl group is an unsubstituted phenyl group.

Still another illustrative Stretcher unit is that of Formula IIIb wherein $R^a$ is —$(CH_2)_5$—:

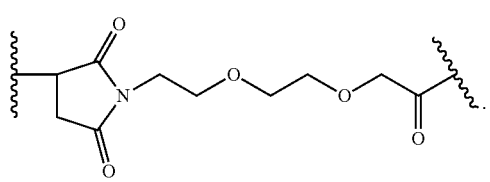 [SMILES: *C(=O)COCCOCCN1C(=O)CC(*)C1=O]

In certain embodiments, the Stretcher unit is linked to the Ligand unit via a disulfide bond between a sulfur atom of the Ligand unit and a sulfur atom of the Stretcher unit. A representative Stretcher unit of this embodiment is depicted within the square brackets of Formula IV, wherein $R^a$, L-, —W—, —Y—, -D, w and y are as defined above.

IV

L—S—[S—$R^a$—C(=O)]—$W_w$—$Y_y$—D

It should be noted that throughout this application, the S moiety in the formula below refers to a sulfur atom of the Ligand unit, unless otherwise indicated by context.

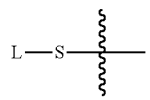

In yet other embodiments, the Stretcher, prior to attachment to L, contains a reactive site that can form a bond with a primary or secondary amino group of the Ligand. Examples of these reactive sites include, but are not limited to, activated esters such as succinimide esters, 4 nitrophenyl esters, pentafluorophenyl esters, tetrafluorophenyl esters, anhydrides, acid chlorides, sulfonyl chlorides, isocyanates and isothiocyanates. Representative Stretcher units of this embodiment are depicted within the square brackets of Formulas Va and Vb, wherein —$R^a$—, L-, —W—, —Y—, -D, w and y are as defined above;

Va

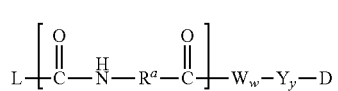

Vb

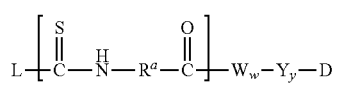

In some embodiments, the Stretcher contains a reactive site that is reactive to a modified carbohydrate's (—CHO) group that can be present on a Ligand. For example, a carbohydrate can be mildly oxidized using a reagent such as sodium periodate and the resulting (—CHO) unit of the oxidized carbohydrate can be condensed with a Stretcher that contains a functionality such as a hydrazide, an oxime, a primary or secondary amine, a hydrazine, a thiosemicarbazone, a hydrazine carboxylate, and an arylhydrazide such as those described by Kaneko et al., 1991, *Bioconjugate Chem.* 2:133-41. Representative Stretcher units of this embodiment are depicted within the square brackets of Formulas VIa, VIb, and VIc, wherein —R$^a$—, L-, —W—, —Y—, -D, w and y are as defined as above.

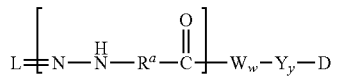

VIa

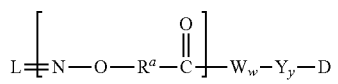

VIb

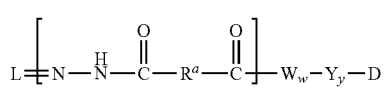

VIc

The Amino Acid Unit

The Amino Acid unit (—W—), when present, links the Stretcher unit to the Spacer unit if the Spacer unit is present, links the Stretcher unit to the Drug moiety if the Spacer unit is absent, and links the Ligand unit to the Drug unit if the Stretcher unit and Spacer unit are absent.

W$_w$— can be, for example, a monopeptide, dipeptide, tripeptide, tetrapeptide, pentapeptide, hexapeptide, heptapeptide, octapeptide, nonapeptide, decapeptide, undecapeptide or dodecapeptide unit. Each —W— unit independently has the formula denoted below in the square brackets, and w is an integer ranging from 0 to 12:

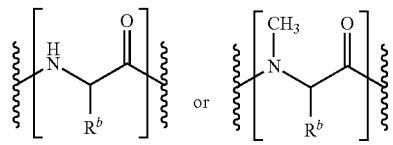

wherein R$^b$ is hydrogen, methyl, isopropyl, isobutyl, sec-butyl, benzyl, p-hydroxybenzyl, —CH$_2$OH, —CH(OH)CH$_3$, —CH$_2$CH$_2$SCH$_3$, —CH$_2$CONH$_2$, —CH$_2$COOH, —CH$_2$CH$_2$CONH$_2$, —CH$_2$CH$_2$COOH, —(CH$_2$)$_3$NHC(=NH)NH$_2$, —(CH$_2$)$_3$NH$_2$, —(CH$_2$)$_3$NHCOCH$_3$, —(CH$_2$)$_3$NHCHO, —(CH$_2$)$_4$NHC(=NH)NH$_2$, —(CH$_2$)$_4$NH$_2$, —(CH$_2$)$_4$NHCOCH$_3$, —(CH$_2$)$_4$NHCHO, —(CH$_2$)$_3$NHCONH$_2$, —(CH$_2$)$_4$NHCONH$_2$, —CH$_2$CH$_2$CH(OH)CH$_2$NH$_2$, 2-pyridylmethyl-, 3-pyridylmethyl-, 4-pyridylmethyl-, phenyl, cyclohexyl,

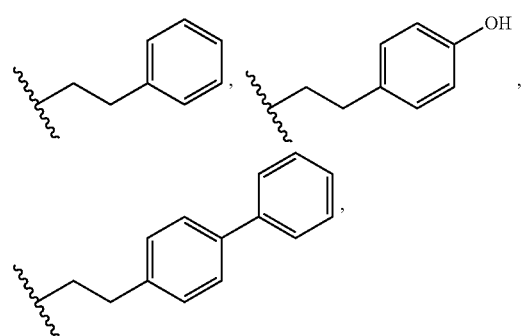

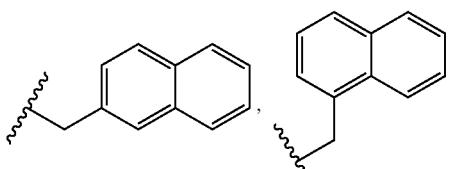

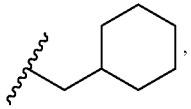

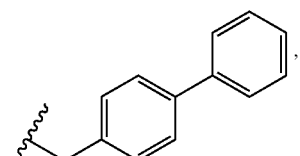

In some embodiments, the Amino Acid unit can be enzymatically cleaved by one or more enzymes, including a cancer or tumor-associated protease, to liberate the Drug unit (-D), which in one embodiment is protonated in vivo upon release to provide a Drug (D).

In certain embodiments, the Amino Acid unit can comprise natural amino acids. In other embodiments, the Amino Acid unit can comprise non-natural amino acids. Illustrative W$_w$ units are represented by formulas (VII)-(IX):

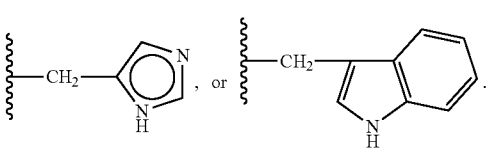

(VII)

wherein R$^c$ and R$^d$ are as follows:

| R$^c$ | R$^d$ |
| --- | --- |
| Benzyl | (CH$_2$)$_4$NH$_2$; |
| methyl | (CH$_2$)$_4$NH$_2$; |
| isopropyl | (CH$_2$)$_4$NH$_2$; |
| isopropyl | (CH$_2$)$_3$NHCONH$_2$; |
| benzyl | (CH$_2$)$_3$NHCONH$_2$; |
| isobutyl | (CH$_2$)$_3$NHCONH$_2$; |
| sec-butyl | (CH$_2$)$_3$NHCONH$_2$; |
| 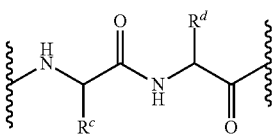 | (CH$_2$)$_3$NHCONH$_2$; |
| benzyl | methyl; |
| benzyl | (CH$_2$)$_3$NHC(=NH)NH$_2$; |

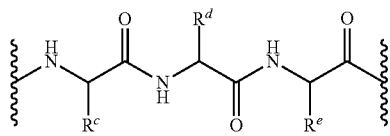

(VIII)

wherein $R^c$, $R^d$ and $R^e$ are as follows:

| $R^c$ | $R^d$ | $R^e$ |
|---|---|---|
| benzyl | Benzyl | $(CH_2)_4NH_2$; |
| isopropyl | Benzyl | $(CH_2)_4NH_2$; and |
| H | Benzyl | $(CH_2)_4NH_2$; |

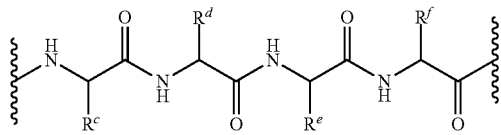

(IX)

wherein $R^c$, $R^d$, $R^e$ and $R^f$ are as follows:

| $R^c$ | $R^d$ | $R^e$ | $R^f$ |
|---|---|---|---|
| H | benzyl | isobutyl | H; and |
| methyl | isobutyl | methyl | isobutyl. |

Exemplary Amino Acid units include, but are not limited to, units of formula VII where: $R^c$ is benzyl and $R^d$ is —$(CH_2)_4NH_2$; $R^c$ is isopropyl and $R^d$ is —$(CH_2)_4NH_2$; or $R^c$ is isopropyl and $R^d$ is —$(CH_2)_3NHCONH_2$. Another exemplary Amino Acid unit is a unit of formula VIII wherein $R^c$ is benzyl, $R^d$ is benzyl, and $R^e$ is —$(CH_2)_4NH_2$.

Useful —$W_w$— units can be designed and optimized in their selectivity for enzymatic cleavage by a particular enzyme, for example, a tumor-associated protease. In one embodiment, a —$W_w$— unit is that whose cleavage is catalyzed by cathepsin B, C and D, or a plasmin protease.

In one embodiment, —$W_w$— is a dipeptide, tripeptide, tetrapeptide or pentapeptide. When $R^b$, $R^c$, $R^d$, $R^e$ or $R^f$ is other than hydrogen, the carbon atom to which $R^b$, $R^c$, $R^d$, $R^e$ or $R^f$ is attached is chiral.

Each carbon atom to which $R^b$, $R^c$, $R^d$, $R^e$ or $R^f$ is attached is independently in the (S) or (R) configuration.

In one aspect of the Amino Acid unit, the Amino Acid unit is valine-citrulline (vc or val-cit). In another aspect, the Amino Acid unit is phenylalanine-lysine (i.e., fk). In yet another aspect of the Amino Acid unit, the Amino Acid unit is N-methylvaline-citrulline. In yet another aspect, the Amino Acid unit is 5-aminovaleric acid, homo phenylalanine lysine, tetraisoquinolinecarboxylate lysine, cyclohexylalanine lysine, isonepecotic acid lysine, beta-alanine lysine, glycine serine valine glutamine and isonepecotic acid.

The Spacer Unit

The Spacer unit (—Y—), when present, links an Amino Acid unit to the Drug unit when an Amino Acid unit is present. Alternately, the Spacer unit links the Stretcher unit to the Drug unit when the Amino Acid unit is absent. The Spacer unit also links the Drug unit to the Ligand unit when both the Amino Acid unit and Stretcher unit are absent.

Spacer units are of two general types: non self-immolative or self-immolative. A non self-immolative Spacer unit is one in which part or all of the Spacer unit remains bound to the Drug moiety after cleavage, particularly enzymatic, of an Amino Acid unit from the antibody drug conjugate. Examples of a non self-immolative Spacer unit include, but are not limited to a (glycine-glycine) Spacer unit and a glycine Spacer unit (both depicted in Scheme 1) (infra). When a conjugate containing a glycine-glycine Spacer unit or a glycine Spacer unit undergoes enzymatic cleavage via an enzyme (e.g., a tumor-cell associated-protease, a cancer-cell-associated protease or a lymphocyte-associated protease), a glycine-glycine-Drug moiety or a glycine-Drug moiety is cleaved from L-Aa-Ww-. In one embodiment, an independent hydrolysis reaction takes place within the target cell, cleaving the glycine-Drug moiety bond and liberating the Drug.

Scheme 1

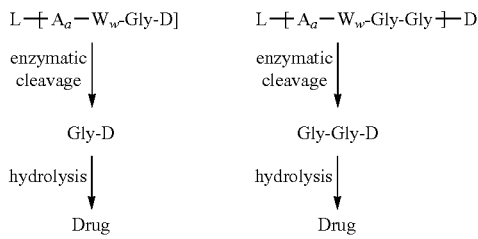

In some embodiments, a non self-immolative Spacer unit (—Y—) is -Gly-. In some embodiments, a non self-immolative Spacer unit (—Y—) is -Gly-Gly-.

In one embodiment, a Drug-Linker conjugate is provided in which the Spacer unit is absent (y=0), or a pharmaceutically acceptable salt thereof.

Alternatively, a conjugate containing a self-immolative Spacer unit can release -D. As used herein, the term "self-immolative Spacer" refers to a bifunctional chemical moiety that is capable of covalently linking together two spaced chemical moieties into a stable tripartite molecule. It will spontaneously separate from the second chemical moiety if its bond to the first moiety is cleaved.

In some embodiments, —$Y_y$— is a p-aminobenzyl alcohol (PAB) unit (see Schemes 2 and 3) whose phenylene portion is substituted with $Q_m$ wherein Q is —$C_1$-$C_8$ alkyl, —$C_2$-$C_8$ alkenyl, —$C_2$-$C_8$ alkynyl, —O—($C_1$-$C_8$ alkyl), —O—($C_2$-$C_8$ alkenyl), —O—($C_2$-$C_8$ alkynyl), -halogen, -nitro or -cyano; and m is an integer ranging from 0-4. The alkyl, alkenyl and alkynyl groups, whether alone or as part of another group, can be optionally substituted.

In some embodiments, —Y— is a PAB group that is linked to —$W_w$— via the amino nitrogen atom of the PAB group, and connected directly to -D via a carbonate, carbamate or ether group. Without being bound by any particular theory or mechanism, Scheme 2 depicts a possible mechanism of Drug release of a PAB group which is attached directly to -D via a carbamate or carbonate group as described by Told et al., 2002, *J. Org. Chem.* 67:1866-1872.

Scheme 2

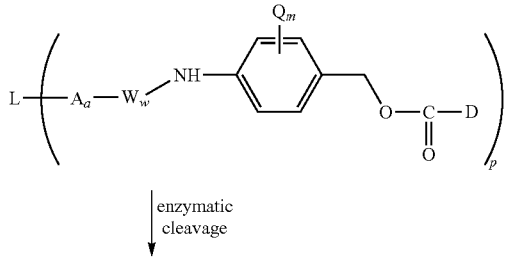

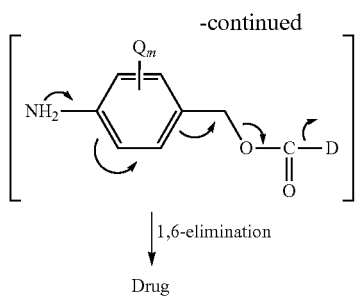

1,6-elimination

Drug

In Scheme 2, Q is —$C_1$-$C_8$ alkyl, —$C_2$-$C_8$ alkenyl, —$C_2$-$C_8$ alkynyl, —O—($C_1$-$C_8$ alkyl), —O—($C_2$-$C_8$ alkenyl), —O—($C_2$-$C_8$ alkynyl), -halogen, -nitro or -cyano; m is an integer ranging from 0-4; and p ranges from 1 to about 20. The alkyl, alkenyl and alkynyl groups, whether alone or as part of another group, can be optionally substituted.

Without being bound by any particular theory or mechanism, Scheme 3 depicts a possible mechanism of Drug release of a PAB group which is attached directly to -D via an ether or amine linkage, wherein D includes the oxygen or nitrogen group that is part of the Drug unit.

Scheme 3

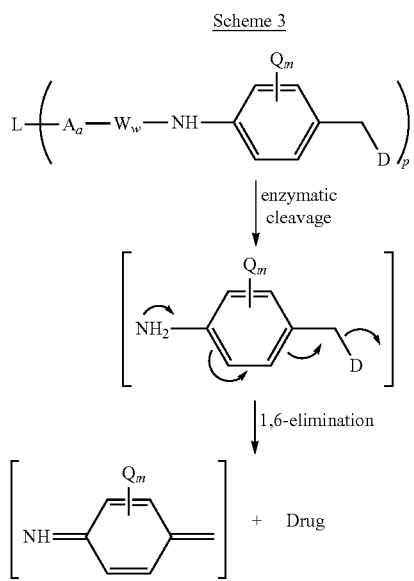

In Scheme 3, Q is —$C_1$-$C_8$ alkyl, —$C_2$-$C_8$ alkenyl, —$C_2$-$C_8$ alkynyl, —O—($C_1$-$C_8$ alkyl), —O—($C_2$-$C_8$ alkenyl), —O—($C_2$-$C_8$ alkynyl), -halogen, -nitro or -cyano; m is an integer ranging from 0-4; and p ranges from 1 to about 20. The alkyl, alkenyl and alkynyl groups, whether alone or as part of another group, can be optionally substituted.

Other examples of self-immolative spacers include, but are not limited to, aromatic compounds that are electronically similar to the PAB group such as 2-aminoimidazol-5-methanol derivatives (Hay et al., 1999, *Bioorg. Med. Chem. Lett.* 9:2237) and ortho or para-aminobenzylacetals. Spacers can be used that undergo cyclization upon amide bond hydrolysis, such as substituted and unsubstituted 4-aminobutyric acid amides (Rodrigues et al., 1995, *Chemistry Biology* 2:223), appropriately substituted bicyclo[2.2.1] and bicyclo[2.2.2] ring systems (Storm et al., 1972, *J. Amer. Chem. Soc.* 94:5815) and 2-aminophenylpropionic acid amides (Amsberry et al., 1990, *J. Org. Chem.* 55:5867). Elimination of amine-containing drugs that are substituted at the α-position of glycine (Kingsbury et al., 1984, *J. Med. Chem.* 27:1447) are also examples of self-immolative spacers.

In some embodiments, the -D moieties are the same. In yet another embodiment, the -D moieties are different.

In one aspect, Spacer units (—$Y_y$—) are represented by Formulae (X)-(XII):

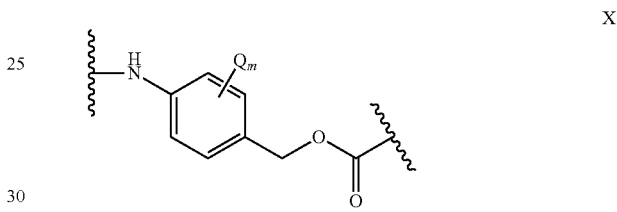

X wherein Q is —$C_1$-$C_8$ alkyl, —$C_2$-$C_8$ alkenyl, —$C_2$-$C_8$ alkynyl, —O—($C_1$-$C_8$ alkyl), —O—($C_2$-$C_8$ alkenyl), —O—($C_2$-$C_8$ alkynyl), -halogen, -nitro or -cyano; and m is an integer ranging from 0-4. The alkyl, alkenyl and alkynyl groups, whether alone or as part of another group, can be optionally substituted.

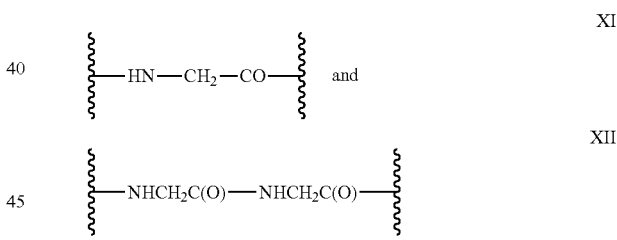

XI

XII

In a group of selected embodiments, the conjugates of Formula I and II are:

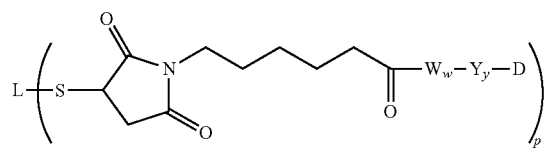
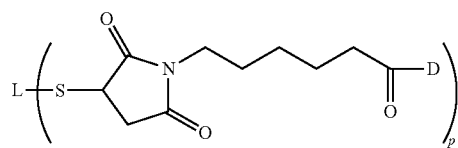

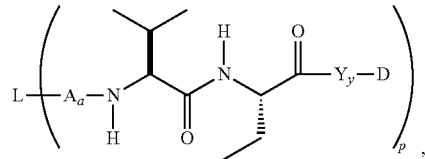
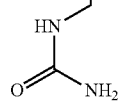

-continued

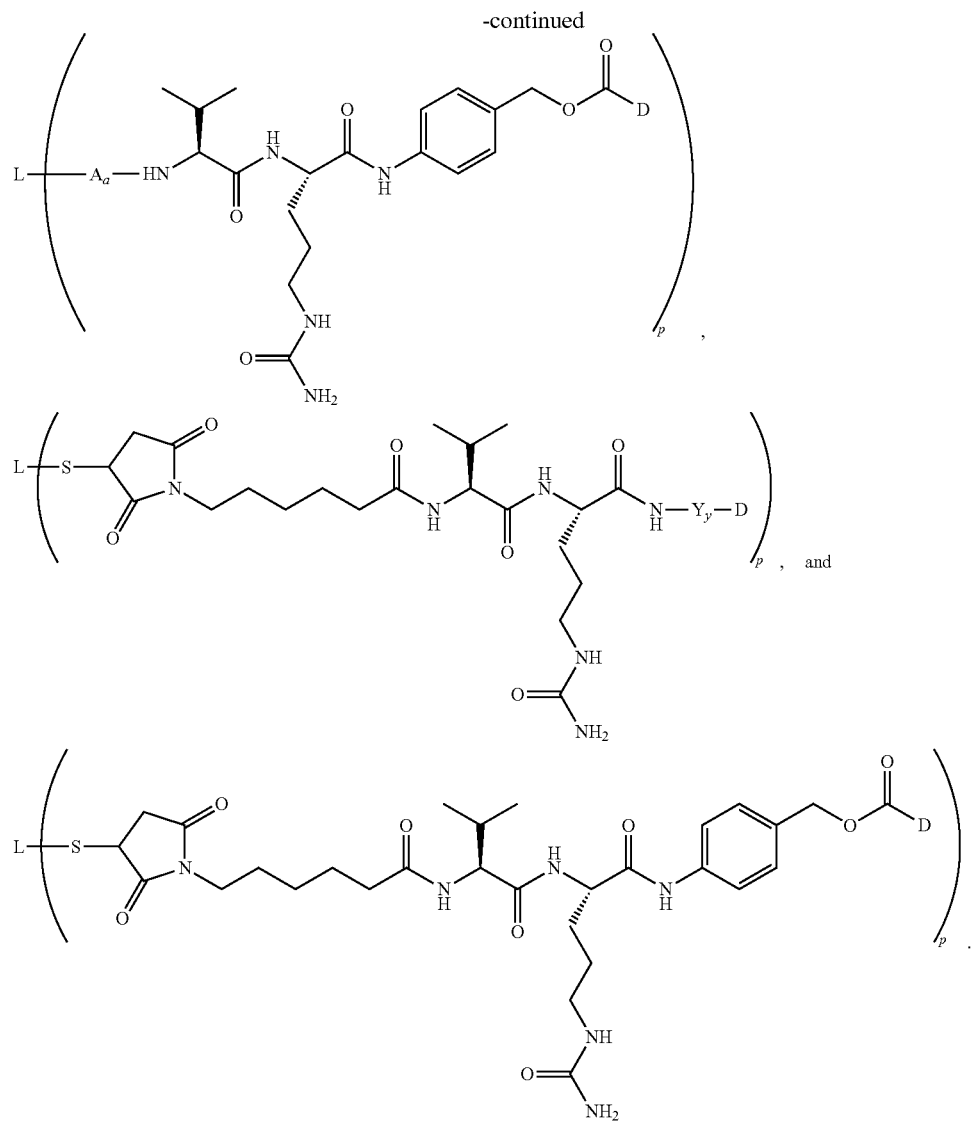

wherein $A_a$, $W_w$, $Y_y$, D and L have the meanings provided herein. In certain embodiments, w and y are each 0, 1 or 2, (preferably when w is 1 or 2, y is 1 or 2)

The Drug Unit

The Drug unit of the Antibody Drug Conjugate is an auristatin, such as auristatin E (also known in the art as a derivative of dolastatin-10) or a derivative thereof. The auristatin can be, for example, an ester formed between auristatin E and a keto acid. For example, auristatin E can be reacted with paraacetyl benzoic acid or benzoylvaleric acid to produce AEB and AEVB, respectively. Other typical auristatins include AFP, MMAF, and MMAE. The synthesis and structure of exemplary auristatins are described in U.S. Patent Application Publication Nos. 2003-0083263, 2005-0238649 and 2005-0009751; International Patent Publication No. WO 04/010957, International Patent Publication No. WO 02/088172, and U.S. Pat. Nos. 6,323,315; 6,239,104; 6,034,065; 5,780,588; 5,665,860; 5,663,149; 5,635,483; 5,599,902; 5,554,725; 5,530,097; 5,521,284; 5,504,191; 5,410,024; 5,138,036; 5,076,973; 4,986,988; 4,978,744; 4,879,278; 4,816,444; and 4,486,414, each of which is incorporated by reference herein in its entirety and for all purposes.

Auristatins have been shown to interfere with microtubule dynamics and nuclear and cellular division and have anti-cancer activity. Auristatins of the present invention bind tubulin and can exert a cytotoxic or cytostatic effect on a desired cell line. There are a number of different assays, known in the art, that can be used for determining whether an auristatin or resultant antibody-drug conjugate exerts a cytostatic or cytotoxic effect on a desired cell line.

Methods for determining whether a compound binds tubulin are known in the art. See, for example, Muller et al., *Anal. Chem* 2006, 78, 4390-4397; Hamel et al., *Molecular Pharmacology*, 1995 47: 965-976; and Hamel et al., *The Journal of Biological Chemistry*, 1990 265:28, 17141-17149. For purposes of the present invention, the relative affinity of a compound to tubulin can be determined Some preferred auristatins of the present invention bind tubulin with an affinity ranging from 10 fold lower (weaker affinity) than the binding affinity of MMAE to tubulin to 10 fold, 20 fold or even 100 fold higher (higher affinity) than the binding affinity of MMAE to tubulin.

In some embodiments, -D is an auristatin of the formula $D_E$ or $D_F$:

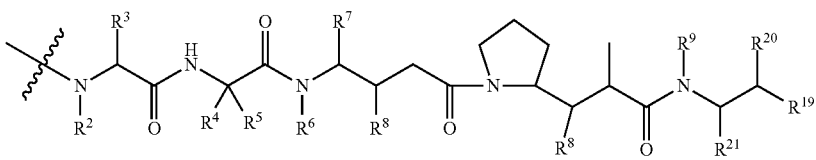

$D_E$

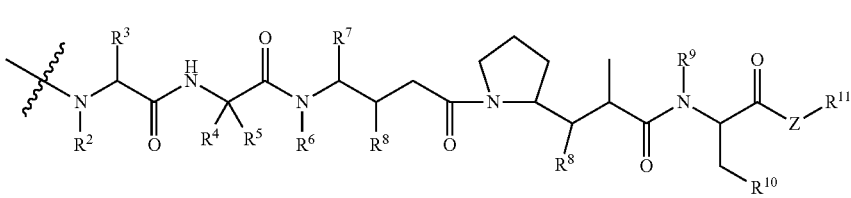

$D_F$ or a pharmaceutically acceptable salt form thereof; wherein, independently at each location:

the wavy line indicates a bond;

$R^2$ is —$C_1$-$C_{20}$ alkyl, —$C_2$-$C_{20}$ alkenyl, or —$C_2$-$C_{20}$ alkynyl;

$R^3$ is —H, —$C_1$-$C_{20}$ alkyl, —$C_2$-$C_{20}$ alkenyl, —$C_2$-$C_{20}$ alkynyl, carbocycle, —$C_1$-$C_{20}$ alkylene (carbocycle), —$C_2$-$C_{20}$ alkenylene(carbocycle), —$C_2$-$C_{20}$ alkynylene (carbocycle), -aryl, —$C_1$-$C_{20}$ alkylene(aryl), —$C_2$-$C_{20}$ alkenylene(aryl), —$C_2$-$C_{20}$ alkynylene(aryl), -heterocycle, —$C_1$-$C_{20}$ alkylene(heterocycle), —$C_2$-$C_{20}$ alkenylene(heterocycle), or —$C_2$-$C_{20}$ alkynylene(heterocycle);

$R^4$ is —H, —$C_1$-$C_{20}$ alkyl, —$C_2$-$C_{20}$ alkenyl, —$C_2$-$C_{20}$ alkynyl, carbocycle, alkylene (carbocycle), —$C_2$-$C_{20}$ alkenylene(carbocycle), —$C_2$-$C_{20}$ alkynylene(carbocycle), -aryl, —$C_1$-$C_{20}$ alkylene(aryl), —$C_2$-$C_{20}$ alkenylene (aryl), —$C_2$-$C_{20}$ alkynylene(aryl), -heterocycle, —$C_1$-$C_{20}$ alkylene(heterocycle), —$C_2$-$C_{20}$ alkenylene(heterocycle), or —$C_2$-$C_{20}$ alkynylene(heterocycle);

$R^5$ is —H or —$C_1$-$C_8$ alkyl;

or $R^4$ and $R^5$ jointly form a carbocyclic ring and have the formula —$(CR^aR^b)_s$— wherein $R^a$ and $R^b$ are independently —H, —$C_1$-$C_{20}$ alkyl, —$C_2$-$C_{20}$ alkenyl, —$C_2$-$C_{20}$ alkynyl, or -carbocycle and s is 2, 3, 4, 5 or 6, $R^6$ is —H, —$C_1$-$C_{20}$ alkyl, —$C_2$-$C_{20}$ alkenyl, or —$C_2$-$C_{20}$ alkynyl;

$R^7$ is —H, —$C_1$-$C_{20}$ alkyl, —$C_2$-$C_{20}$ alkenyl, —$C_2$-$C_{20}$ alkynyl, -carbocycle, —$C_1$-$C_{20}$ alkylene (carbocycle), —$C_2$-$C_{20}$ alkenylene(carbocycle), —$C_2$-$C_{20}$ alkynylene (carbocycle), -aryl, —$C_1$-$C_{20}$ alkylene(aryl), —$C_2$-$C_{20}$ alkenylene(aryl), —$C_2$-$C_{20}$ alkynylene(aryl), heterocycle, —$C_1$-$C_{20}$ alkylene(heterocycle), —$C_2$-$C_{20}$ alkenylene (heterocycle), or —$C_2$-$C_{20}$ alkynylene(heterocycle);

each $R^8$ is independently —H, —OH, —$C_1$-$C_{20}$ alkyl, —$C_2$-$C_{20}$ alkenyl, —$C_2$-$C_{20}$ alkynyl, —O—($C_1$-$C_{20}$ alkyl), —O—($C_2$-$C_{20}$ alkenyl), —O—($C_1$-$C_{20}$ alkynyl), or -carbocycle;

$R^9$ is —H, —$C_1$-$C_{20}$ alkyl, —$C_2$-$C_{20}$ alkenyl, or —$C_2$-$C_{20}$ alkynyl;

$R^{19}$ is -aryl, -heterocycle, or -carbocycle;

$R^{20}$ is —H, —$C_1$-$C_{20}$ alkyl, —$C_2$-$C_{20}$ alkenyl, —$C_2$-$C_{20}$ alkynyl, -carbocycle, —O—($C_1$-$C_{20}$ alkyl), —O—($C_2$-$C_{20}$ alkenyl), —O—($C_2$-$C_{20}$ alkynyl), or $OR^{18}$ wherein $R^{18}$ is —H, a hydroxyl protecting group, or a direct bond where $OR^{18}$ represents =O;

$R^{21}$ is —H, —$C_1$-$C_{20}$ alkyl, —$C_2$-$C_{20}$ alkenyl, or —$C_2$-$C_{20}$ alkynyl, -aryl, -heterocycle, or -carbocycle;

$R^{10}$ is -aryl or -heterocycle;

Z is —O—, —S—, —NH—, or —$NR^{12}$—, wherein $R^{12}$ is —$C_1$-$C_{20}$ alkyl, —$C_2$-$C_{20}$ alkenyl, —$C_2$-$C_{20}$ alkynyl;

$R^{11}$ is —H, —$C_1$-$C_{20}$ alkyl, —$C_2$-$C_{20}$ alkenyl, —$C_2$-$C_{20}$ alkynyl, -aryl, -heterocycle, —$(R^{13}O)_m$—$R^{14}$, or —$(R^{13}O)_m$—$CH(R^{15})_2$;

m is an integer ranging from 0-1000;

$R^{13}$ is —$C_2$-$C_{20}$ alkylene, —$C_2$-$C_{20}$ alkenylene, or —$C_2$-$C_{20}$ alkynylene;

$R^{14}$ is —H, —$C_1$-$C_{20}$ alkyl, —$C_2$-$C_{20}$ alkenyl, or —$C_2$-$C_{20}$ alkynyl;

each occurrence of $R^{15}$ is independently —H, —COOH, —$(CH_2)_n$—$N(R^{16})_2$, —$(CH_2)_n$—$SO_3H$, —$(CH_2)_n$—$SO_3$—$C_1$-$C_{20}$ alkyl, —$(CH_2)_n$—$SO_3$—$C_2$-$C_{20}$ alkenyl, or —$(CH_2)_n$—$SO_3$—$C_2$-$C_{20}$ alkynyl;

each occurrence of $R^{16}$ is independently —H, —$C_1$-$C_{20}$ alkyl, —$C_2$-$C_{20}$ alkenyl, —$C_2$-$C_{20}$ alkynyl or —$(CH_2)_n$—COOH; and n is an integer ranging from 0 to 6; wherein said alkyl, alkenyl, alkynyl, alkylene, alkenylene, alkynylene, aryl, carbocycle, and heterocycle radicals, whether alone or as part of another group, are optionally substituted.

Auristatins of the formula $D_E$ include those wherein said alkyl, alkenyl, alkynyl, alkylene, alkenylene, alkynylene, aryl, carbocycle, and heterocycle radicals are unsubstituted.

Auristatins of the formula $D_E$ include those wherein the groups of $R^2$, $R^3$, $R^4$, $R^5$, $R^6$, $R^7$, $R^8$, and $R^9$ are unsubstituted and the groups of $R^{19}$, $R^{20}$ and $R^{21}$ are optionally substituted as described herein.

Auristatins of the formula $D_E$ include those wherein $R^2$ is —$C_1$-$C_8$ alkyl;

$R^3$, $R^4$ and $R^7$ are independently selected from —H, —$C_1$-$C_{20}$ alkyl, —$C_2$-$C_{20}$ alkenyl, —$C_2$-$C_{20}$ alkynyl, monocyclic $C_3$-$C_6$ carbocycle, —$C_1$-$C_{20}$ alkylene(monocyclic $C_3$-$C_6$ carbocycle), —$C_2$-$C_{20}$ alkenylene(monocyclic $C_3$-$C_6$ carbocycle), —$C_2$-$C_{20}$ alkynylene(monocyclic $C_3$-$C_6$ carbocycle), —$C_6$-$C_{10}$ aryl, —$C_1$-$C_{20}$ alkylene($C_6$-$C_{10}$ aryl), —$C_2$-$C_{20}$ alkenylene($C_6$-$C_{10}$ aryl), —$C_2$-$C_{20}$ alkynylene ($C_6$-$C_{10}$ aryl), -heterocycle, —$C_1$-$C_{20}$ alkylene(heterocycle), —$C_2$-$C_{20}$ alkenylene(heterocycle), or —$C_2$-$C_{20}$ alkynylene (heterocycle); wherein said alkyl, alkenyl, alkynyl, alkylene, alkenylene, alkynylene, carbocycle, aryl, and heterocycle radicals are optionally substituted;

$R^5$ is -hydrogen;

$R^6$ is —$C_1$-$C_8$ alkyl;

each $R^8$ is independently selected from —OH, —O—($C_1$-$C_{20}$ alkyl), —O—($C_2$-$C_{20}$ alkenyl), or —O—($C_2$-$C_{20}$ alkynyl) wherein said alkyl, alkenyl, and alkynyl radicals are optionally substituted;

$R^9$ is -hydrogen or —$C_1$-$C_8$ alkyl;

$R^{19}$ is optionally substituted phenyl;

$R^{20}$ is $OR^{18}$; wherein $R^{18}$ is H, a hydroxyl protecting group, or a direct bond where $OR^{18}$ represents =O;

$R^{21}$ is selected from —H, —$C_1$-$C_{20}$ alkyl, —$C_2$-$C_{20}$ alkenyl, —$C_2$-$C_{20}$ alkynyl, or -carbocycle; wherein said alkyl, alkenyl, alkynyl, and carbocycle radicals are optionally substituted; or a pharmaceutically acceptable salt form thereof.

Auristatins of the formula $D_E$ include those wherein $R^2$ is methyl;

$R^3$ is —H, —$C_1$-$C_8$ alkyl, —$C_2$-$C_8$ alkenyl, or —$C_2$-$C_8$ alkynyl, wherein said alkyl, alkenyl and alkynyl radicals are optionally substituted;

$R^4$ is —H, —$C_1$-$C_8$ alkyl, —$C_2$-$C_8$ alkenyl, —$C_2$-$C_8$ alkynyl, monocyclic $C_3$-$C_6$ carbocycle, —$C_6$-$C_{10}$ aryl, —$C_1$-$C_8$ alkylene($C_6$-$C_{10}$ aryl), —$C_2$-$C_8$ alkenylene($C_6$-$C_{10}$ aryl), —$C_2$-$C_8$ alkynylene($C_6$-$C_{10}$ aryl), —$C_1$-$C_8$ alkylene (monocyclic $C_3$-$C_6$ carbocycle), —$C_2$-$C_8$ alkenylene (monocyclic $C_3$-$C_6$ carbocycle), —$C_2$-$C_8$ alkynylene(monocyclic $C_3$-$C_6$ carbocycle); wherein said alkyl, alkenyl, alkynyl, alkylene, alkenylene, alkynylene, aryl, and carbocycle radicals whether alone or as part of another group are optionally substituted;

$R^5$ is H; $R^6$ is methyl;

$R^7$ is —$C_1$-$C_8$ alkyl, —$C_2$-$C_8$ alkenyl or —$C_2$-$C_8$ alkynyl;

each $R^8$ is methoxy;

$R^9$ is -hydrogen or —$C_1$-$C_8$ alkyl;

$R^{19}$ is phenyl;

$R^{20}$ is $OR^{18}$; wherein $R^{18}$ is —H, a hydroxyl protecting group, or a direct bond where $OR^{18}$ represents =O;

$R^{21}$ is methyl; or a pharmaceutically acceptable salt form thereof.

Auristatins of the formula $D_E$ include those wherein $R^2$ is methyl; $R^3$ is H or $C_1$-$C_3$ alkyl; $R^4$ is $C_1$-$C_5$ alkyl; $R^5$ is H; $R^6$ is methyl; $R^7$ is isopropyl or sec-butyl; $R^8$ is methoxy; $R^9$ is hydrogen or $C_1$-$C_8$ alkyl; $R^{19}$ is phenyl; $R^{20}$ is $OR^{18}$; wherein $R^{18}$ is H, a hydroxyl protecting group, or a direct bond where $OR^{18}$ represents =O; and $R^{21}$ is methyl; or a pharmaceutically acceptable salt form thereof.

Auristatins of the formula $D_E$ include those wherein $R^2$ is methyl or $C_1$-$C_3$ alkyl; $R^3$ is H or $C_1$-$C_3$ alkyl; $R^4$ is $C_1$-$C_5$ alkyl; $R^5$ is H; $R^6$ is $C_1$-$C_3$ alkyl; $R^7$ is $C_1$-$C_5$ alkyl; $R^8$ is $C_1$-$C_3$ alkoxy; $R^9$ is hydrogen or $C_1$-$C_8$ alkyl; $R^{19}$ is phenyl; $R^{20}$ is $OR^{18}$; wherein $R^{18}$ is H, a hydroxyl protecting group, or a direct bond where $OR^{18}$ represents =O; and $R^{21}$ is $C_1$-$C_3$ alkyl; or a pharmaceutically acceptable salt form thereof.

Auristatins of the formula $D_F$ include those wherein $R^2$ is methyl;

$R^3$, $R^4$, and $R^7$ are independently selected from —H, —$C_1$-$C_{20}$ alkyl, —$C_2$-$C_{20}$ alkenyl, —$C_2$-$C_{20}$ alkynyl, monocyclic $C_3$-$C_6$ carbocycle, —$C_1$-$C_{20}$ alkylene(monocyclic $C_3$-$C_6$ carbocycle), —$C_2$-$C_{20}$ alkenylene(monocyclic $C_3$-$C_6$ carbocycle), —$C_2$-$C_{20}$ alkynylene(monocyclic $C_3$-$C_6$ carbocycle), —$C_6$-$C_{10}$ aryl, —$C_1$-$C_{20}$ alkylene($C_6$-$C_{10}$ aryl), —$C_2$-$C_{20}$ alkenylene($C_6$-$C_{10}$ aryl), —$C_2$-$C_{20}$ alkynylene ($C_6$-$C_{10}$ aryl), -heterocycle, —$C_1$-$C_{20}$ alkylene(heterocycle), —$C_2$-$C_{20}$ alkenylene(heterocycle), or —$C_2$-$C_{20}$ alkynylene (heterocycle); wherein said alkyl, alkenyl, alkynyl, alkylene, alkenylene, alkynylene, carbocycle, aryl, and heterocycle radicals whether alone or as part of another group are optionally substituted;

$R^5$ is —H;

$R^6$ is methyl;

each $R^8$ is methoxy;

$R^9$ is —H, —$C_1$-$C_{20}$ alkyl, —$C_2$-$C_{20}$ alkenyl, or —$C_2$-$C_{20}$ alkynyl; wherein said alkyl, alkenyl and alkynyl radical are optionally substituted;

$R^{10}$ is optionally substituted aryl or optionally substituted heterocycle;

Z is —O—, —S—, —NH—, or —$NR^{12}$—, wherein $R^{12}$ is —$C_1$-$C_{20}$ alkyl, —$C_2$-$C_{20}$ alkenyl, or —$C_2$-$C_{20}$ alkynyl, each of which is optionally substituted;

$R^{11}$ is —H, —$C_1$-$C_{20}$ alkyl, —$C_2$-$C_{20}$ alkenyl, —$C_2$-$C_{20}$ alkynyl, -aryl, -heterocycle, —$(R^{13}O)_m$—$R^{14}$, or —$(R^{13}O)_m$—$CH(R^{15})_2$, wherein said alkyl, alkenyl, alkynyl, aryl, and heterocycle radicals are optionally substituted;

m is an integer ranging from 0-1000;

$R^{13}$ is —$C_2$-$C_{20}$ alkylene, —$C_2$-$C_{20}$ alkenylene, or —$C_2$-$C_{20}$ alkynylene, each of which is optionally substituted;

$R^{14}$ is —H, —$C_1$-$C_{20}$ alkyl, —$C_2$-$C_{20}$ alkenyl, or —$C_2$-$C_{20}$ alkynyl wherein said alkyl, alkenyl and alkynyl radicals are optionally substituted;

each occurrence of $R^{15}$ is independently —H, —COOH, —$(CH_2)_n$—$N(R^{16})_2$, —$(CH_2)_n$—$SO_3H$, —$(CH_2)_n$—$SO_3$—$C_1$-$C_{20}$ alkyl, —$(CH_2)_n$—$SO_3$—$C_2$-$C_{20}$ alkenyl, or —$(CH_2)_n$—$SO_3$—$C_2$-$C_{20}$ alkynyl wherein said alkyl, alkenyl and alkynyl radicals are optionally substituted;

each occurrence of $R^{16}$ is independently —H, —$C_1$-$C_{20}$ alkyl, —$C_2$-$C_{20}$ alkenyl, —$C_2$-$C_{20}$ alkynyl or —$(CH_2)_n$—COOH wherein said alkyl, alkenyl and alkynyl radicals are optionally substituted;

n is an integer ranging from 0 to 6; or a pharmaceutically acceptable salt form thereof.

In certain of these embodiments, $R^{10}$ is optionally substituted phenyl;

Auristatins of the formula $D_F$ include those wherein the groups of $R^2$, $R^3$, $R^4$, $R^5$, $R^6$, $R^7$, $R^8$, and $R^9$ are unsubstituted and the groups of $R^{10}$ and $R^{11}$ are as described herein.

Auristatins of the formula $D_F$ include those wherein said alkyl, alkenyl, alkynyl, alkylene, alkenylene, alkynyklene, aryl, carbocycle, and heterocycle radicals are unsubstituted.

Auristatins of the formula $D_F$ include those wherein $R^2$ is $C_1$-$C_3$ alkyl; $R^3$ is H or $C_1$-$C_3$ alkyl; $R^4$ is $C_1$-$C_5$ alkyl; $R^5$ is H; $R^6$ is $C_1$-$C_3$ alkyl; $R^7$ is $C_1$-$C_5$ alkyl; $R^8$ is $C_1$-$C_3$ alkoxy; $R^9$ is hydrogen or $C_1$-$C_8$ alkyl; $R^{10}$ is optionally substituted phenyl; Z is O, S, or NH; and $R^{11}$ is as defined herein; or a pharmaceutically acceptable salt form thereof.

Auristatins of the formula $D_F$ include those wherein $R^2$ is methyl; $R^3$ is H or $C_1$-$C_3$ alkyl; $R^4$ is $C_1$-$C_5$ alkyl; $R^5$ is H; $R^6$ is methyl; $R^7$ is isopropyl or sec-butyl; $R^8$ is methoxy; $R^9$ is hydrogen or $C_1$-$C_8$ alkyl; $R^{10}$ is optionally substituted phenyl; Z is O, S, or NH; and $R^{11}$ is as defined herein; or a pharmaceutically acceptable salt form thereof.

Auristatins of the formula $D_F$ include those wherein $R^2$ is methyl; $R^3$ is H or $C_1$-$C_3$ alkyl; $R^4$ is $C_1$-$C_5$ alkyl; $R^5$ is H; $R^6$ is methyl; $R^7$ is isopropyl or sec-butyl; $R^8$ is methoxy; $R^9$ is hydrogen or $C_1$-$C_8$ alkyl; $R^{10}$ is phenyl; and Z is O or NH and $R^{11}$ is as defined herein, preferably hydrogen; or a pharmaceutically acceptable salt form thereof.

Auristatins of the formula $D_F$ include those wherein $R^2$ is $C_1$-$C_3$ alkyl; $R^3$ is H or $C_1$-$C_3$ alkyl; $R^4$ is $C_1$-$C_5$ alkyl; $R^5$ is H; $R^6$ is $C_1$-$C_3$ alkyl; $R^7$ is $C_1$-$C_5$ alkyl; $R^8$ is $C_1$-$C_3$ alkoxy; $R^9$ is hydrogen or $C_1$-$C_8$ alkyl; $R^{10}$ is phenyl; and Z is O or NH and $R^{11}$ is as defined herein, preferably hydrogen; or a pharmaceutically acceptable salt form thereof.

Auristatins of the formula $D_E$ or $D_F$ include those wherein $R^3$, $R^4$ and $R^7$ are independently isopropyl or sec-butyl and $R^5$ is —H. In an exemplary embodiment, $R^3$ and $R^4$ are each isopropyl, $R^5$ is H, and $R^7$ is sec-butyl. The remainder of the substituents are as defined herein.

Auristatins of the formula $D_E$ or $D_F$ include those wherein $R^2$ and $R^6$ are each methyl, and $R^9$ is H. The remainder of the substituents are as defined herein.

Auristatins of the formula $D_E$ or $D_F$ include those wherein each occurrence of $R^8$ is —OCH$_3$. The remainder of the substituents are as defined herein.

Auristatins of the formula $D_E$ or $D_F$ include those wherein $R^3$ and $R^4$ are each isopropyl, $R^2$ and $R^6$ are each methyl, $R^5$ is H, $R^7$ is sec-butyl, each occurrence of $R^8$ is —OCH$_3$, and $R^9$ is H. The remainder of the substituents are as defined herein.

Auristatins of the formula $D_F$ include those wherein Z is —O— or —NH—. The remainder of the substituents are as defined herein.

Auristatins of the formula $D_F$ include those wherein $R^{10}$ is aryl. The remainder of the substituents are as defined herein.

Auristatins of the formula $D_F$ include those where $R^{10}$ is -phenyl. The remainder of the substituents are as defined herein.

Auristatins of the formula $D_F$ include those wherein Z is —O—, and $R^{11}$ is H, methyl or t-butyl. The remainder of the substituents are as defined herein.

Auristatins of the formula $D_F$ include those wherein, when Z is —NH, $R^{11}$ is —($R^{13}$O)$_m$—CH($R^{15}$)$_2$, wherein $R^{15}$ is —(CH$_2$)$_n$—N(R$_{16}$)$_2$, and $R^{16}$ is —C$_1$-C$_8$ alkyl or —(CH$_2$)$_n$—COOH. The remainder of the substituents are as defined herein.

Auristatins of the formula $D_F$ include those wherein when Z is —NH, $R^{11}$ is —($R^{13}$O)$_m$—CH($R^{15}$)$_2$, wherein $R^{15}$ is H or —(CH$_2$)$_n$—SO$_3$H. The remainder of the substituents are as defined herein.

In preferred embodiments, when D is an auristatin of formula $D_E$, w is an integer ranging from 1 to 12, preferably 2 to 12, y is 1 or 2, and a is 1 or 2, preferably 1.

In some embodiments, wherein D is an auristatin of formula $D_F$, a is 1 and w and y are 0.

Illustrative Drug units (-D) include the drug units having the following structures:

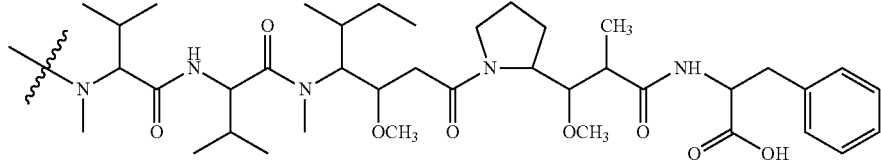

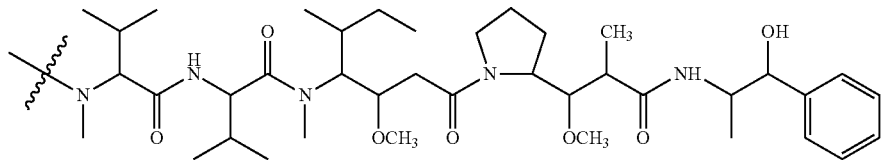

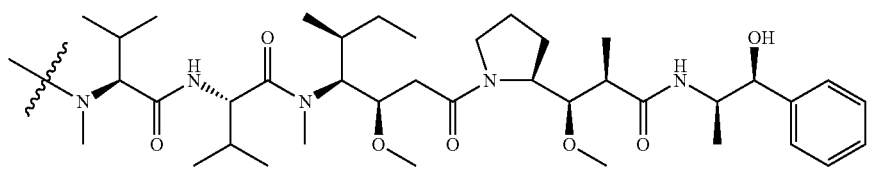

-continued

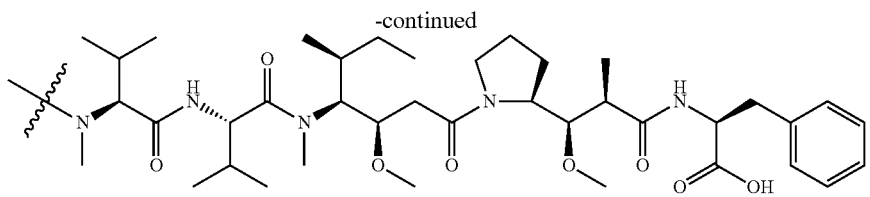

or pharmaceutically acceptable salts or solvates thereof.

In one aspect, hydrophilic groups, such as but not limited to triethylene glycol esters (TEG) can be attached to the Drug Unit at $R^{11}$. Without being bound by theory, the hydrophilic groups assist in the internalization and non-agglomeration of the Drug unit.

Exemplary Antibody Drug Conjugates have the following structures wherein "mAb" represents a monoclonal antibody and S is a sulfur atom of the antibody. In one aspect, the sulfur atom is a sulfur atom from a cysteine residue. In one embodiment, the cysteine residue is cysteine residue of a reduced interchain thiol. In another aspect, the cysteine residue is a cysteine residue introduced into the antibody. The subscript p is an integer of from 1 to about 20 and is preferably 1 to about 5. In embodiments, wherein p represents the average number of Drug molecules per Ligand in a composition comprising a plurality of Antibody Drug Conjugates, p is preferably from about 2 to about 6, or from about 3 to about 5.

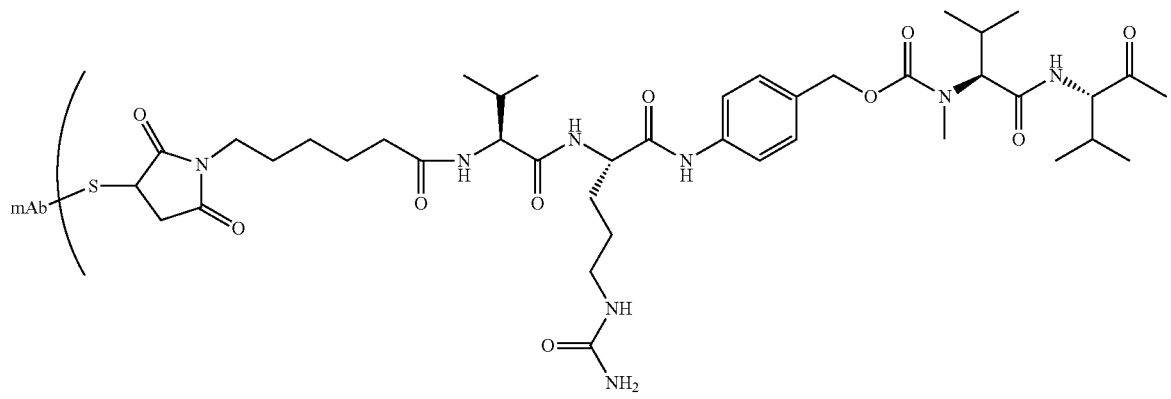

L-mc-vc-MMAF

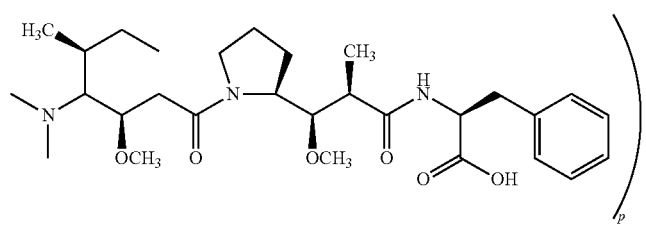

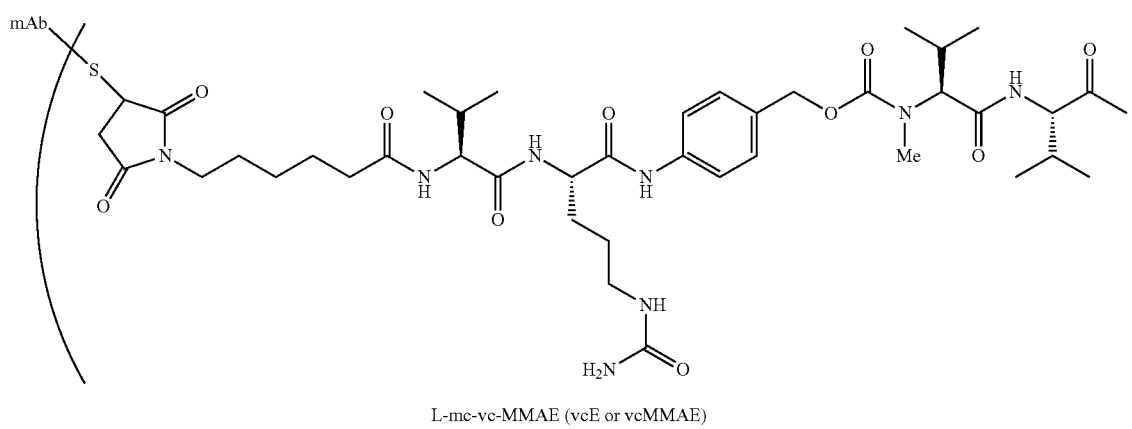

L-mc-vc-MMAE (vcE or vcMMAE)

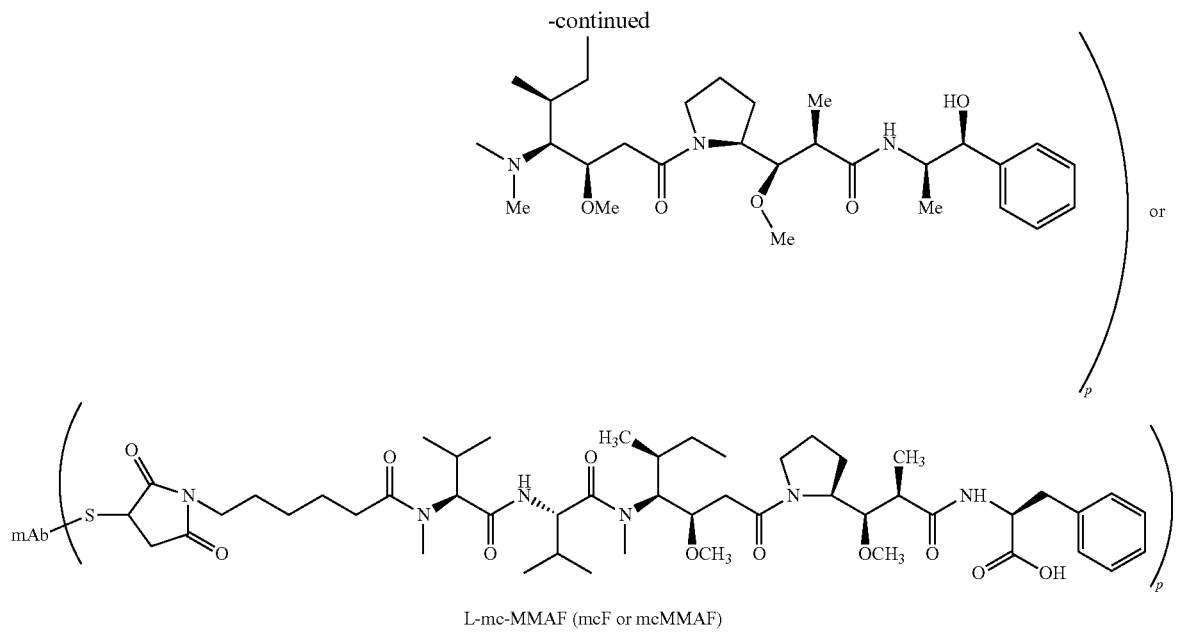

L-mc-MMAF (mcF or mcMMAF)

or pharmaceutically acceptable salt forms thereof.

Ligand Unit

In the present invention, the Ligand unit (e.g., antibody) in the Antibody Drug Conjugate specifically binds to a cancer cell antigen that is on the surface of a cancer cell.

In exemplary embodiments, the antibody will specifically binds to a cancer cell antigen that is on the surface of a cancer cell that demonstrates upregulation of the PI3K-AKT-mTOR pathway, including constitutive activation of the PI3K/AKT mTOR pathway. In one aspect, the Antibody Drug Conjugate exhibits cytotoxic activity via internalization.

The Ligand unit (L) has at least one functional group that can form a bond with a functional group of a Linker unit. Useful functional groups that can be present on a Ligand unit, either naturally, via chemical manipulation or via engineering, include, but are not limited to, sulfhydryl (—SH), amino, hydroxyl, carboxy, the anomeric hydroxyl group of a carbohydrate, and carboxyl. In some embodiments, a Ligand unit functional group is a sulfhydryl group. The sulfhydryl group is typically a solvent accessible sulfhydryl group, such as a solvent accessible sulfhydryl group on a cysteine residue. Sulfhydryl groups can be generated by reduction of an intramolecular or intermolecular disulfide bond of a Ligand. Sulfhydryl groups also can be generated by reaction of an amino group of a lysine moiety of a Ligand using 2-iminothiolane (Traut's reagent) or another sulfhydryl generating reagent.

In some embodiments, one or more sulfhydryl groups are engineered into a Ligand unit, such as by amino acid substitution. For example, a sulfhydryl group can be introduced into a Ligand unit. In some embodiments, a sulfhydryl group is introduced by an amino acid substitution of serine or threonine to a cysteine residue, and/or by addition of a cysteine residue into a Ligand unit (an engineered cysteine residue). In some embodiments, the cysteine residue is an internal cysteine residue, i.e., not located at the N-terminus or C-terminus of the Ligand moiety.

To control the number of Drug or Linker unit-Drug units attached to a Ligand unit, one or more cysteine residues can be eliminated by amino acid substitution. For example, the number of solvent accessible cysteine residues in an immunoglobulin hinge region can be reduced by amino acid substitution of cysteine to serine residues.

In some embodiments, a Ligand unit contains 1, 2, 3, 4, 5, 6 7 or 8 solvent-accessible cysteine residues. In some embodiments, a Ligand unit contains 2 or 4 solvent-accessible cysteine residues.

Antibodies employed in the methods and compositions described herein are preferably monoclonal, and may be multispecific, human, humanized or chimeric antibodies, single chain antibodies, Fab fragments, F(ab') fragments, fragments produced by a Fab expression library, and binding fragments of any of the above, provided that they can be conjugated to an auristatin drug either directly or indirectly via a linker. Typically, the antibodies are human antibodies, humanized antibodies, or chimeric antibodies having a variable region derived from a murine monoclonal antibody and a human immunoglobulin constant region. In some embodiments, the antibodies can be rodent (e.g., mouse and rat), donkey, sheep, rabbit, goat, guinea pig, camelid, horse, or chicken.

The antibodies can be mono-specific, bi-specific, tri-specific, or of greater multi-specificity. Multi-specific antibodies maybe specific for different epitopes of different target antigens or may be specific for different epitopes on the same target antigen. (See, e.g., WO 93/17715; WO 92/08802; WO 91/00360; WO 92/05793; Tutt et al., 1991, *J. Immunol.* 147:60-69; U.S. Pat. Nos. 4,474,893; 4,714,681; 4,925,648; 5,573,920; and 5,601,819; Kostelny et al., 1992, *J. Immunol.* 148:1547-1553.)

The antibodies can also be described in terms of their binding affinity to a target antigen of $10^{-7}$ M, $5\times10^{-8}$ M, $10^{-8}$ M, $5\times10^{-9}$ M, $10^{-9}$ M, $5\times10^{-10}$ M, $10^{-10}$ M, $5\times10^{-11}$ M, $10^{-11}$ M, $5\times10^{-12}$ M, $10^{-12}$ M, $5\times10^{-13}$ M, $10^{-13}$ M, $5\times10^{-14}$ M, $10^{-14}$ M, $5\times10^{-15}$ M, or $10^{-15}$ M.

In some embodiments, the antibody is a chimeric antibody. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. (See, e.g., Morrison, *Science*, 1985, 229:1202; Oi et al., 1986, *BioTechniques* 4:214; Gillies et al., 1989, *J. Immunol. Methods* 125:191-202; U.S. Pat. Nos. 5,807,715; 4,816,567; and 4,816,397.)

In some embodiments, the antibody can be a humanized antibody, including a veneered antibody. Humanized antibodies are antibody molecules that bind the desired antigen and have one or more complementarity determining regions (CDRs) from a non-human species, and framework and constant regions from a human immunoglobulin molecule. Often, framework residues in the human framework regions will be substituted with the corresponding residue from the CDR donor antibody to alter, or preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riecbmann et al., 1988, *Nature* 332:323.)

The antibody can also be a human antibody. Human antibodies can be made by a variety of methods known in the art such as phage display methods using antibody libraries derived from human immunoglobulin sequences. See e.g., U.S. Pat. No. 4,444,887 and U.S. Pat. No. 4,716,111; WO 98/46645, WO 98/50433, WO 98/24893, WO 98/16654, WO 96/34096, WO 96/33735, and WO 91/10741.

Examples of antibodies include those that specifically bind to antigens expressed by cancers that demonstrate upregulation of the PI3K-AKT-mTOR pathway, including constitutive activation of the PI3K/AKT mTOR pathway. In an exemplary embodiment, the antibody will bind to the CD19, CD30, or CD70 antigen.

Exemplary antibodies include, for example, chimeric or humanized forms of the murine AC10 (anti-CD30), murine 1F6 (anti-CD70), and murine BU12 (anti-CD19) antibodies. The murine AC10 antibody has a heavy chain variable region having the amino acid sequence set forth in SEQ ID NO:1 and a light chain variable region having the amino acid sequence set forth in SEQ ID NO:2. The murine 1F6 antibody has a heavy chain variable region having the amino acid sequence set forth in SEQ ID NO:3 and a light chain variable region having the amino acid sequence set forth in SEQ ID NO:4. The murine BU12 antibody has a heavy chain variable region having the amino acid sequence set forth in SEQ ID NO:7 and a light chain variable region having the amino acid sequence set forth in SEQ ID NO:8. These antibodies are further described in U.S. Pat. No. 7,090,843; and US Publications Number 20090148942, and 20090136526 which are incorporated herein by reference in their entirety and for all purposes.

In an exemplary embodiment, the antibody is a chimeric or humanized version of a mouse antibody having (i) a heavy chain variable region having the amino acid sequence set forth in SEQ ID NO:1 and a light chain variable region having the amino acid sequence set forth in SEQ ID NO:2; (ii) a heavy chain variable region having the amino acid sequence set forth in SEQ ID NO:3 and a light chain variable region having the amino acid sequence set forth in SEQ ID NO:4; or (iii) a heavy chain variable region having the amino acid sequence set forth in SEQ ID NO:7 and a light chain variable region having the amino acid sequence set forth in SEQ ID NO:8. In an exemplary embodiment, such an antibody further comprises the amino acid sequence of the human gamma I constant region set forth in SEQ ID NO:11 or amino acids 1 to 329 of SEQ ID NO:11 and the amino acid sequence of the human kappa constant region set forth in SEQ ID NO:12.

In an exemplary embodiment, the antibody is a chimeric AC10 antibody having a heavy chain variable region having the amino acid sequence set forth in SEQ ID NO:1 and a light chain variable region having the amino acid sequence set forth in SEQ ID NO:2. In an exemplary embodiment, such an antibody further comprises the amino acid sequence of the human gamma I constant region set forth in SEQ ID NO:11 or amino acids 1 to 329 of SEQ ID NO:11 and the amino acid sequence of the human kappa constant region set forth in SEQ ID NO:12.

In an exemplary embodiment, the antibody is a humanized h1F6 antibody having a heavy chain variable region having the amino acid sequence set forth in SEQ ID NO:5 and a light chain variable region having the amino acid sequence set forth in SEQ ID NO:6. In an exemplary embodiment, such an antibody further comprises the amino acid sequence of the human gamma I constant region set forth in SEQ ID NO:11 or amino acids 1 to 329 of SEQ ID NO:11 and the amino acid sequence of the human kappa constant region set forth in SEQ ID NO:12.

In an exemplary embodiment, the antibody is a humanized hBU12 antibody having a heavy chain variable region having the amino acid sequence set forth in SEQ ID NO:9 and a light chain variable region having the amino acid sequence set forth in SEQ ID NO:10. In an exemplary embodiment, such an antibody further comprises the amino acid sequence of the human gamma I constant region set forth in SEQ ID NO:11 or amino acids 1 to 329 of SEQ ID NO:11 and the amino acid sequence of the human kappa constant region set forth in SEQ ID NO:12.

Antibodies can be assayed for specific binding to a target antigen by conventional methods, such as for example, competitive and non-competitive immunoassay systems using techniques such as Western blots, radioimmunoassays, ELISA (enzyme linked immunosorbent assay), "sandwich" immunoassays, immunoprecipitation assays, immunoradiometric assays, fluorescent immunoassays, protein A immunoassays, and flow cytometry. (See, e.g., Ausubel et al., eds., *Short Protocols in Molecular Biology* (John Wiley & Sons, Inc., New York, 4th ed. 1999); Harlow & Lane, *Using Antibodies: A Laboratory Manual* (Cold Spring Harbor Laboratory Press, Cold Spring Harbor, N.Y., 1999.)

Further, the binding affinity of an antibody to a target antigen and the off-rate of an antibody-antigen interaction can be determined by surface plasmon resonance, competition FACS using labeled antibodies or other competitive binding assays.

Antibodies can be made from antigen-containing fragments of the target antigen by standard procedures according to the type of antibody (see, e.g., Kohler, et al., *Nature*, 256:495, (1975); Harlow & Lane, *Antibodies, A Laboratory Manual* (C.S.H.P., NY, 1988); Queen et al., *Proc. Natl. Acad. Sci. USA* 86:10029-10033 (1989) and WO 90/07861; Dower et al., WO 91/17271 and McCafferty et al., WO 92/01047 (each of which is incorporated by reference for all purposes).

Cytotoxicity Assays for Antibody Drug Conjugates

Methods of determining whether a Drug or Antibody Drug Conjugate exerts a cytostatic and/or cytotoxic effect on a cell are known. Generally, the cytotoxic or cytostatic activity of an Antibody Drug Conjugate can be measured by: exposing cells expressing a target protein of the Antibody Drug Conjugate in a cell culture medium; culturing the cells for a period from about 6 hours to about 5 days; and measuring cell viability. Cell-based in vitro assays can be used to measure viability (proliferation), cytotoxicity, and induction of apoptosis (caspase activation) of the Antibody Drug Conjugate.

For determining whether an Antibody Drug Conjugate exerts a cytostatic effect, a thymidine incorporation assay may be used. For example, cancer cells expressing a target antigen at a density of 5,000 cells/well of a 96-well plated can be cultured for a 72-hour period and exposed to 0.5 µCi of $^3$H-thymidine during the final 8 hours of the 72-hour period. The incorporation of $^3$H-thymidine into cells of the culture is measured in the presence and absence of the Antibody Drug Conjugate.

For determining cytotoxicity, necrosis or apoptosis (programmed cell death) can be measured. Necrosis is typically accompanied by increased permeability of the plasma membrane; swelling of the cell, and rupture of the plasma membrane. Apoptosis is typically characterized by membrane blebbing, condensation of cytoplasm, and the activation of endogenous endonucleases. Determination of any of these effects on cancer cells indicates that an Antibody Drug Conjugate is useful in the treatment of cancers.

Cell viability can be measured by determining in a cell the uptake of a dye such as neutral red, trypan blue, or ALAMAR™ blue (see, e.g., Page et al., 1993, *Intl. J. Oncology* 3:473-476). In such an assay, the cells are incubated in media containing the dye, the cells are washed, and the remaining dye, reflecting cellular uptake of the dye, is measured spectrophotometrically. The protein-binding dye sulforhodamine B (SRB) can also be used to measure cytoxicity (Skehan et al., 1990, *J. Natl. Cancer Inst.* 82:1107-12).

Alternatively, a tetrazolium salt, such as MTT, is used in a quantitative colorimetric assay for mammalian cell survival and proliferation by detecting living, but not dead, cells (see, e.g., Mosmann, 1983, *J. Immunol. Methods* 65:55-63).

Apoptosis can be quantitated by measuring, for example, DNA fragmentation. Commercial photometric methods for the quantitative in vitro determination of DNA fragmentation are available. Examples of such assays, including TUNEL, (which detects incorporation of labeled nucleotides in fragmented DNA) and ELISA-based assays, are described in *Biochemica*, 1999, no. 2, pp. 34-37 (Roche Molecular Biochemicals).

Apoptosis can also be determined by measuring morphological changes in a cell. For example, as with necrosis, loss of plasma membrane integrity can be determined by measuring uptake of certain dyes (e.g., a fluorescent dye such as, for example, acridine orange or ethidium bromide). A method for measuring apoptotic cell number has been described by Duke and Cohen, Current Protocols in Immunology (Coligan et al. eds., 1992, pp. 3.17.1-3.17.16). Cells also can be labeled with a DNA dye (e.g., acridine orange, ethidium bromide, or propidium iodide) and the cells observed for chromatin condensation and margination along the inner nuclear membrane. Other morphological changes that can be measured to determine apoptosis include, e.g., cytoplasmic condensation, increased membrane blebbing, and cellular shrinkage.

The presence of apoptotic cells can be measured in both the attached and "floating" compartments of the cultures. For example, both compartments can be collected by removing the supernatant, trypsinizing the attached cells, combining the preparations following a centrifugation wash step (e.g., 10 minutes at 2000 rpm), and detecting apoptosis (e.g., by measuring DNA fragmentation). (See, e.g., Piazza et al., 1995, *Cancer Research* 55:3110-16).

The effects of Antibody Drug Conjugates can be tested or validated in animal models. A number of established animal models of cancers are known to the skilled artisan, any of which can be used to assay the efficacy of an Antibody Drug Conjugate. Non-limiting examples of such models are described infra. Moreover, small animal models to examine the in vivo efficacies of Antibody Drug Conjugates can be created by implanting human tumor cell lines into appropriate immunodeficient rodent strains, e.g., athymic nude mice or SCID mice.

Inhibitors of the PI3K-AKT-mTOR Pathway mTOR exists in two types of complexes, mTORC1 containing the raptor subunit and mTORC2 containing rictor. As known in the art, "rictor" refers to a cell growth regulatory protein having human gene locus 5p13.1. These complexes are regulated differently and have a different spectrum of substrates.

mTORC2 is generally insensitive to rapamycin and selective inhibitors. mTORC2 is thought to modulate growth factor signaling by phosphorylating the C-terminal hydrophobic motif of some AGC kinases such as Akt. In many cellular contexts, mTORC2 is required for phosphorylation of the S473 site of Akt. Thus, mTORC1 activity is partly controlled by Akt whereas Akt itself is partly controlled by mTORC2.

Growth factor stimulation of the phosphatidylinositol 3-kinase (PI3K) causes activation of Akt by phosphorylation at the two key sites, S473 and T308. It has been reported that full activation of Akt requires phosphorylation of both S473 and T308Active. Akt promotes cell survival and proliferation in many ways including suppressing apoptosis, promoting glucose uptake, and modifying cellular metabolism. Of the two phosphorylation sites on Akt, activation loop phosphorylation at T308, mediated by PDK1, is believed to be indispensable for kinase activity, while hydrophobic motif phosphorylation at 5473 enhances Akt kinase activity. AKT phosphorylation at S473 can be used as a marker for constitutive activation of the PI3K/AKT mTOR pathway. In some aspects, AKT phosphorylation at both S473 and T308 is used as a maker for constitutive activation of the PI3K/AKT mTOR pathway.

mTOR Inhibitors

The mTOR inhibitors used in the present invention can provide synergistic effect when used in combination therapy with auristatin based antibody-drug conjugates for the treatment of cancer, for the killing of tumor cells and/or for inhibiting the proliferation of tumor cells.

As used herein, the term "mTOR inhibitor" refers to a compound or a ligand that inhibits at least one activity of an mTOR protein, such as, for example, the serine/threonine protein kinase activity on at least one of its substrates (e.g., p70S6 kinase 1, 4E-BP1, AKT/PKB and eEF2).

The mTOR inhibitors of the present invention are able to bind directly to and inhibit mTORC1, mTORC2 or both mTORC1 and mTORC2 by binding to mTORC1 and/or mTORC1.

One class of mTOR inhibitors for use in the present invention are active site inhibitors. These are mTOR inhibitors that bind to the ATP binding site (also referred to as ATP binding pocket) of mTOR and inhibit the catalytic activity of both mTORC1 and mTORC2. Accordingly, in one aspect, an mTOR inhibitor for use in the present invention competes with ATP for binding to the ATP-binding site on mTORC1 and/or mTORC2. Exemplary assays for whether a compound competes with ATP are known in the art. One such assay is provided in example 12.

A class of active site inhibitors for use in the present invention are dual specificity inhibitors as they target and directly inhibit both PI3K and mTOR. Dual specificity inhibitors bind to both the ATP binding site of mTOR and PI3K. Examples of such inhibitors include wortmannin, LY294002, PI-103 (Cayman chemical), SF1126 (Semafore), BGT226 (Novartis), XL765 (Exelixis) and NVP-BEZ235 (Novartis). (Liu et al., Nature Review, 8, 627-644, 2009). In some aspects, the dual specificity inhibitor will be an imidazoquinazoline (e.g., imidazo[4,5-c]quinoline derivative). Exemplary assays for whether a compound binds to and/or inhibit PI3K and/or mTOR are known in the art. One such assay is provided in example 12.

Another class of active site inhibitors for use in the present invention are selective mTOR inhibitors. This class of mTOR inhibitors selectively inhibit mTORC1 and mTORC2 activity relative to one or more type I phophatidylinositol 3-kinases. The type I phophatidylinositol 3-kinases can be selected from, for example, PI3 kinase α, PI3 kinase β, PI3 kinase γ, or PI3 kinase δ. These active site inhibitors bind to the active site of mTOR but not PI3K. Examples of such inhibitors include Torin1 (Guertin and Sabatini), PP242 (2-(4-Amino-1-isopropyl-1H-pyrazolo[3,4-d]pyrimidin-3-yl)-1H-indol-5-ol), PP30, Ku-0063794, WAY-600 (Wyeth), WAY-687 (Wyeth), WAY-354 (Wyeth), and AZD8055 (Sparks and Guertin, Oncogene, 29, 2733-2744, 2010, Liu et al., Nature Review, 8, 627-644, 2009). In some aspects, the mTor inhibitor will be a pyrazolopyrimidine. Methods for determining selectivity of mTOR inhibitors are known in the art. One such assay is provided in example 12.

In one aspect, a selective mTOR inhibitor alternatively can be understood to refer to an agent that exhibits a 50% inhibitory concentration (IC50) with respect to mTORC1 and/or mTORC2, that is at least 10-fold, at least 20-fold, at least 50-fold, at least 100-fold, at least 1000-fold, or more, lower than the inhibitor's IC50 with respect to one, two, three, or more type I PI3-kinases.

In some embodiments, a selective mTOR inhibitor alternatively can be understood to refer to an agent that exhibits a 50% inhibitory concentration (IC50) with respect to mTORC1 and/or mTORC2, that is at least 10-fold, at least 20-fold, at least 50-fold, at least 100-fold, at least 1000-fold, or more, lower than the inhibitor's IC50 with respect to all of the type I PI3-kinases.

In yet another aspect, a selective mTOR inhibitor can be understood to refer to a compound that exhibits a 50% inhibitory concentration (IC50) with respect to mTOR, that is at least 10-fold, at least 20-fold, at least 50-fold, at least 100-fold, at least 1000-fold, or more, lower than the inhibitor's IC50 with respect to one or more protein kinases.

Another class of mTOR inhibitors for use in the present invention are referred to herein as "rapalogs". As used herein the term "rapalogs" refers to compounds that specifically bind to the mTOR FRB domain (FKBP rapamycin binding domain), are structurally related to rapamycin, and retain the mTOR inhibiting properties. The term rapalogs excludes rapamycin. Rapalogs include esters, ethers, oximes, hydrazones, and hydroxylamines of rapamycin, as well as compounds in which functional groups on the rapamycin core structure have been modified, for example, by reduction or oxidation. Pharmaceutically acceptable salts of such compounds are also considered to be rapamycin derivatives. In some embodiments, rapalogs, like rapamycin, selectively inhibit mTORC1 relative to mTORC2. Exemplary rapalogs for use in the present invention include, for example, temsirolimus (CC1779), everolimus (RAD001), deforolimus (AP23573), AZD8055 (AstraZeneca), and OSI-027 (OSI). Exemplary assays for identifying whether a compound binds to the mTOR FRB domain are known in the art. See, for example, Chen et al. (1995) PNAS vol 92 pp. 4947-4951.

Another mTOR inhibitor for use in the present invention is rapamycin (sirolimus).

Any of the mTOR inhibitors, including any of the classes of mTOR inhibitors described above, can be used in combination with the auristatin based antibody drug conjugates of the present invention. In some embodiments, the mTOR inhibitor used in the present invention is not rapamycin (sirolimus).

In one aspect, exemplary mTOR inhibitors for use in the present invention inhibit either mTORC1, mTORC2 or both mTORC1 and mTORC2 with an IC50 (concentration that inhibits 50% of the activity) of about 200 nM or less, preferably about 100 nm or less, even more preferably about 60 nM or less, about 25 nM, about 10 nM, about 5 nM, about 1 nM, 100 pM, 50 pM, 25 pM, 10 pM, 1 pM, or less. In one aspect, a mTOR inhibitor for use in the present invention inhibits either mTORC1, mTORC2 or both mTORC1 and mTORC2 with an IC50 from about 2 nM to about 100 nm, more preferably from about 2 nM to about 50 nM, even more preferably from about 2 nM to about 15 nM.

In one aspect, exemplary mTOR inhibitors for use in the present invention inhibit either PI3K and mTORC1 or mTORC2 or both mTORC1 and mTORC2 and PI3K with an IC50 (concentration that inhibits 50% of the activity) of about 200 nM or less, preferably about 100 nm or less, even more preferably about 60 nM or less, about 25 nM, about 10 nM, about 5 nM, about 1 nM, 100 pM, 50 pM, 25 pM, 10 pM, 1 pM, or less. In one aspect, a mTOR inhibitor for use in the present invention inhibits PI3K and mTORC1 or mTORC2 or both mTORC1 and mTORC2 and PI3K with an IC50 from about 2 nM to about 100 nm, more preferably from about 2 nM to about 50 nM, even more preferably from about 2 nM to about 15 nM.

IC50 determinations can be accomplished using any conventional techniques known in the art. For example, an IC50 can be determined by measuring the activity of a given enzyme in the presence of a range of concentrations of the inhibitor under study. The experimentally obtained values of enzyme activity then are plotted against the inhibitor concentrations used. The concentration of the inhibitor that shows 50% enzyme activity (as compared to the activity in the absence of any inhibitor) is taken as the "IC50" value. Analogously, other inhibitory concentrations can be defined through appropriate determinations of activity.

mTOR has been shown to demonstrate a robust and specific catalytic activity toward the physiological substrate proteins, p70 S6 ribosomal protein kinase I (p70S6K1) and eIF4E binding protein 1 (4EBP1) as measured by phosphor-specific antibodies in Western blotting. In one aspect, IC50 determinations can be accomplished by measuring the phosphorylation level of substrate proteins, such as p70S6K1 and 4EBP1. Cells, for example, may be contacted with the inhibitor under study under conditions which would normally yield phosphorylation of mTOR substrates p70S6K1 and 4EBP1. Cells may then be prepared by various methods known to the art including fixation or lysis, and analyzed for the phosphorylation levels of mTOR substrates. Phosphorylation levels may be analyzed using any methods known to the art including but not limited to the use of antibodies specific for the phosphorylated forms of the substrates to be assayed via immunoblot or flow cytometry.

Inhibition of mTORC1 and/or mTORC2 activity can be determined by a reduction in signal transduction of the PI3K/Akt/mTOR pathway. A wide variety of readouts can be utilized to establish a reduction of the output of such signaling pathway. Some non-limiting exemplary readouts include (1) a decrease in phosphorylation of Akt at residues, including but not limited to 5473 and T308; (2) a decrease in activation of Akt as evidenced, for example, by a reduction of phosphorylation of Akt substrates including but not limited to Fox01/O3a T24/32, GSK3α/β; S21/9, and TSC2 T1462; (3) a decrease in phosphorylation of signaling molecules downstream of mTOR, including but not limited to ribosomal S6 S240/244, 70S6K T389, and 4EBP1 T37/46; and (4) inhibition of proliferation of cancerous cells.

Cell-based assays for establishing selective inhibition of mTORC1 and/or mTORC2 can take a variety of formats. This generally will depend on the biological activity and/or the signal transduction readout that is under investigation. For example, the ability of the agent to inhibit mTORC1 and/or mTORC2 to phosphorylate the downstream substrate(s) can be determined by various types of kinase assays known in the art. Representative assays include but are not limited to immunoblotting and immunoprecipitation with antibodies such as anti-phosphotyrosine, anti-phosphoserine or anti-phosphothreonine antibodies that recognize phosphorylated proteins. Alternatively, antibodies that specifically recognize a particular phosphorylated form of a kinase substrate (e.g. anti-phospho AKT S473 or anti-phospho AKT T308) can be used. In addition, kinase activity can be detected by high throughput chemiluminescent assays. In another aspect, single cell assays such as flow cytometry as described in the phosflow experiment can be used to measure phosphorylation of multiple downstream mTOR substrates in mixed cell populations.

Effect of inhibition of mTORC1 and/or mTORC2 and/or PI3K can be established by cell colony formation assay or other forms of cell proliferation assay. A wide range of cell proliferation assays are available in the art, and many of which are available as kits. Non-limiting examples of cell proliferation assays include testing for tritiated thymidine uptake assays, BrdU (5'-bromo-2'-deoxyuridine) uptake (kit marketed by Calibochem), MTS uptake (kit marketed by Promega), MTT uptake (kit marketed by Cayman Chemical), CyQUANT® dye uptake (marketed by Invitrogen).

Apoptosis and cell cycle arrest analysis can be performed with any methods exemplified herein as well other methods known in the art. Many different methods have been devised to detect apoptosis.

The dissociation-enhanced lanthanide fluorescence immunoassay and assays described in Toral-Barz et al., Biochemical and Biophysical Research Communications, 332 (2005), 304-310, can be used to determine whether a compound is an mTOR inhibitor.

PI3K Inhibitors

The PI3K inhibitors used in the present invention can provide synergistic effect when used in combination therapy with auristatin based antibody-drug conjugates.

As used herein, the term "PI3K inhibitor" refers to a compound or a ligand that binds to and inhibits at least one activity of PI3K. The PI3K proteins can be divided into three classes, class 1 PI3Ks, class 2 PI3Ks, and class 3 PI3Ks. Class 1 PI3Ks exist as heterodimers consisting of one of four p110 catalytic subunits (p110α, p110β, p110δ, and p110γ) and one of two families of regulatory subunits. A PI3K inhibitor of the present invention preferably targets the class 1 PI3K inhibitors. In one aspect, a PI3K inhibitor will display selectivity for one or more isoforms of the class 1 PI3K inhibitors (i.e., selectivity for p110α, p110β, p110δ, and p110γ or one or more of p110α, p110β, p110δ, and p110γ). In another aspect, a PI3K inhibitor will not display isoform selectivity. In one aspect, a PI3K inhibitor will compete for binding with ATP to the PI3K catalytic domain.

A PI3K inhibitor can, for example, target PI3K as well as additional proteins in the PI3K-AKT-mTOR pathway. A PI3K inhibitor that targets both mTOR and PI3K can be referred to as either a mTOR inhibitor or a PI3K inhibitor. A PI3K inhibitor that only targets PI3K can be referred to as a selective PI3K inhibitor. In one aspect, a selective PI3K inhibitor can be understood to refer to an agent that exhibits a 50% inhibitory concentration with respect to PI3K that is at least 10-fold, at least 20-fold, at least 30-fold, at least 50-fold, at least 100-fold, at least 1000-fold, or more, lower than the inhibitor's IC50 with respect to mTOR and/or other proteins in the pathway.

In one aspect, exemplary PI3K inhibitors for use in the present invention inhibit PI3K with an IC50 (concentration that inhibits 50% of the activity) of about 200 nM or less, preferably about 100 nm or less, even more preferably about 60 nM or less, about 25 nM, about 10 nM, about 5 nM, about 1 nM, 100 pM, 50 pM, 25 pM, 10 pM, 1 pM, or less. In one aspect, a PI3K inhibitor for use in the present invention inhibits PI3K with an IC50 from about 2 nM to about 100 nm, more preferably from about 2 nM to about 50 nM, even more preferably from about 2 nM to about 15 nM.

Examples of PI3K inhibitors for use in combination with auristatin based antibody-drug conjugates include, for example, BKM120 (class 1 PI3K inhibitor, Novartis), XL147 (class 1 PI3K inhibitor, Exelixis), GDC0941 (class 1 PI3K inhibitor, Genentech), GSK1059615 (pan-PI3K inhibitor, GlaxoSmithKline), PX-866 (class 1 PI3K inhibitor; p110α, p110β, and p110γ isoforms, Oncothyreon), and CAL-101 (class 1 PI3K inhibitor; p110δ isoform, Calistoga).

AKT Inhibitors

The AKT inhibitors used in the present invention can provide synergistic effect when used in combination therapy with auristatin based antibody-drug conjugates.

As used herein, the term "AKT inhibitor" refers to a compound or a ligand that binds to and inhibits at least one activity of AKT. AKT inhibitors can be grouped into several classes, including lipid-based inhibitors (e.g., inhibitors that target the pleckstrin homology domain of AKT which prevents AKT from localizing to plasma membranes), ATP-competitive inhibitors, and allosteric inhibitors. In one aspect, AKT inhibitors act by binding to the AKT catalytic site. In one aspect, Akt inhibitors act by inhibiting phosphorylation of downstream AKT targets such as mTOR.

The AKT inhibitors can target all three AKT isoforms, AKT1, AKT2, AKT3 or may be isoform selective and target only one or two of the AKT isoforms. An AKT inhibitor can, for example, target AKT as well as additional proteins in the PI3K-AKT-mTOR pathway. An AKT inhibitor that only targets AKT can be referred to as a selective AKT inhibitor. In one aspect, a selective AKT inhibitor can be understood to refer to an agent that exhibits a 50% inhibitory concentration with respect to AKT that is at least 10-fold, at least 20-fold, at least 30-fold, at least 50-fold, at least 100-fold, at least 1000-fold, or more lower than the inhibitor's IC50 with respect to other proteins in the pathway.

In one aspect, exemplary AKT inhibitors for use in the present invention inhibit AKT with an IC50 (concentration that inhibits 50% of the activity) of about 200 nM or less, preferably about 100 nm or less, even more preferably about 60 nM or less, about 25 nM, about 10 nM, about 5 nM, about 1 nM, 100 pM, 50 pM, 25 pM, 10 pM, 1 pM, or less. In one aspect, a AKT inhibitor for use in the present invention inhibits AKT with an IC50 from about 2 nM to about 100 nm, more preferably from about 2 nM to about 50 nM, even more preferably from about 2 nM to about 15 nM.

Examples of AKT inhibitors for use in combination with auristatin based antibody-drug conjugates include, for example, perifosine (Keryx), MK2206 (Merck), VQD-002 (VioQuest), XL418 (Exelixis), and PX316 (PROLX Pharmaceuticals).

Cancers

The methods of the present invention encompass administering combination therapy to a subject for the treatment of cancer. In exemplary embodiments, the cancer to be treated by the present invention demonstrates upregulation of the PI3K-AKT-mTOR pathway.

The methods of the present invention encompass administering combination therapy to a subject for the treatment of cancer. In exemplary embodiments, the cancer to be treated by the present invention demonstrates upregulation of the PI3K-AKT-mTOR pathway.

Upregulation of PI3K-AKT-mTOR pathway can be determined by an increase in signal transduction of the PI3K/Akt/mTOR pathway. A wide variety of readouts can be utilized to establish an increase in the output of such signaling pathway. Some non-limiting exemplary readouts include (1) an increase in phosphorylation of Akt at residues, including but not limited to S473 and T308; (2) an increase in activation of Akt as evidenced by a reduction of phosphorylation of Akt substrates including but not limited to Fox01/03a T24/32, GSK3α/β; S21/9, and TSC2 T1462; and (3) an increase in phosphorylation of signaling molecules downstream of mTOR, including but not limited to ribosomal S6 S240/244, 70S6K T389, and 4EBP1 T37/46.

Accordingly, in one aspect, a cancer to be treated by the present methods is one in which the PI3K/AKT mTOR pathway is constitutively activated as demonstrated by the presence of phosphorylated AKT (pAKT) and, in particular, phosphorylation of AKT at at least one of two key sites, S473 and T308, and, preferably, at both sites. In one aspect, cancerous tissue will have elevated levels of pAKT as compared to non-cancerous tissue.

In another aspect, a cancer to be treated by the present methods is one in which the PI3K/AKT mTOR pathway is upregulated as demonstrated by the presence of phosphorylated p70 S6 ribosomal protein kinase I (p70S6K1), phosphorylated S6 ribosomal protein, and/or e1F4E binding protein 1. In one aspect, cancerous tissue will have elevated levels of p70S6K1 and/or phospho-e1F4E binding protein 1 as compared to non-cancerous tissue.

The presence of pAKT has been previously reported in many cancers. Such cancers include hematological malignancies. Accordingly, in some embodiments, the methods described herein are for treating hematological malignancies. In one aspect, the hematological malignancies are lymphomas. In one aspect, the hematological malignancies are B cell lymphomas. In another embodiment, the hematological malignancies are T cell lymphomas. Examples of particular lymphomas include, Hodgkin lymphoma and Non-Hodgkin lymphoma (NHL). Examples of NHL include, for example, mantle cell lymphoma, anaplastic large cell lymphoma, cutaneous T-cell lymphoma, peripheral T-cell lymphoma, diffuse large B-cell lymphoma, Burkitt lymphoma, and follicular lymphoma. In another embodiment, the hematological malignancies is a leukemia, such as, for example, acute lymphoblastic leukemia or chronic lymphocytic leukemia The presence of pAKT has been previously reported in many solid tumors, including, for example, colorectal, renal, gastric, prostate, thyroid, endometrial, lung, brain and breast cancer. Accordingly, in some embodiments, the methods described herein are for treating solid tumors. Examples of solid tumors treatable by the methods include, for example, colorectal, renal, gastric, prostate, thyroid, endometrial, lung, brain and breast cancer. In one aspect, the cancer is renal cell carcinoma.

The present invention encompasses combination therapy for the treatment of cancers characterized by the presence of pAKT. For example, in some embodiments, the hematological malignancy, lymphoma, Hogkin lymphoma, NHL, or leukemia treatable by the present invention will express phosphorylated AKT. Similarly, in some embodiments, the solid tumor, colorectal, renal, gastric, prostate, thyroid, endometrial, lung, brain or breast cancer will express phosphorylated AKT. Expression can be cytoplasmic or nuclear. In one aspect, the expression is substantially cytoplasmic. In another aspect, the expression is substantially nuclear. In another aspect the expression is cytoplasmic and nuclear.

The present invention encompasses combination therapy for the treatment of cancers characterized by the presence of phosphorylated p70 S6 ribosomal protein kinase I (p70S6K1) and/or e1F4E binding protein 1. For example, in some embodiments, the hematological malignancy, lymphoma, Hogkin lymphoma, or NHL treatable by the present invention will express phosphorylated p70 S6 ribosomal protein kinase I (p70S6K1) and/or e1F4E binding protein 1. Similarly, in some embodiments, the solid tumor, colorectal, renal, gastric, prostate, thyroid, endometrial, lung, brain or breast cancer will express phosphorylated p70 S6 ribosomal protein kinase I (p70S6K1) and/or e1E4E (phopho-e1F4E binding protein 1).

In some embodiments, the cancer will have high pAKT expression. In exemplary embodiments, high pAKT expression refers to a median number of p-AKT+ cells/mm$^2$ tumor area greater than about 25 cells/mm$^2$, greater than 50 cells/mm$^2$, or even greater than 100 cells/mm$^2$. Determination of the amount of pAKT+ cells is generally performed using immunohistochemistry techniques.

Any of the cancers described herein can be treated using combination therapy with an auristatin based antibody drug conjugate and a mTOR inhibitor, including any of the classes of mTOR inhibitors described herein, and any of the auristatin based antibody drug conjugates described herein. The antibody component of the auristatin based antibody drug conjugate will specifically bind to a cancer cell antigen which is expressed on the surface of the cancer cell to be treated.

In some embodiments, the cancer will be one that expresses a CD30 antigen and the auristatin based antibody drug conjugate will be one that specifically binds to the CD30 antigen (e.g., the antibody component is an anti-CD30 antibody, preferably an anti-CD30 monoclonal antibody). The auristatin based antibody drug conjugate after binding to the antigen will be internalized into the cancer cells, where it exerts its effect. In one aspect, the cancer that expresses the CD30 antigen expresses pAKT (AKT phosphorylated on S473 and T308). In one aspect, the cancer will have high pAKT expression. The cancer can be, for example, a hematological malignancy, including, for example, B cell or T cell lymphoma or leukemia. In some embodiments, the cancer is Hodgkin lymphoma, Mantle Cell lymphoma, Diffuse large B Cell Lymphoma, chronic lymphocytic leukemia, acute lymphoblastic leukemia, cutaneous T-cell lymphoma, peripheral T-cell lymphoma, or any of the other CD30 expressing cancers described herein, including solid tumors. Accordingly, combination therapy according to the present methods can include administration of the anti-CD30 auristatin based antibody drug conjugate with an inhibitor of the PI3K-AKT-mTOR pathway for the treatment of a CD30 expressing cancer (e.g., B cell or T cell lymphoma, Hodgkin lymphoma, NHL, leukemia, or solid tumor). In some aspects, the inhibitor will be a mTOR inhibitor, a PI3K inhibitor, or an AKT inhibitor. In one aspect, the mTOR inhibitor will be an active site inhibitor, including, for example, a dual specificity inhibitor such as wortmannin, LY294002, PI-103, BGT226, SF1126, XL765 and NVP-BEZ235 (Liu et al., Nature Review, 8, 627-644, 2009) or a selective mTOR inhibitor, including, for example, Torin1, PP242, PP30, Ku-0063794, WAY-600, WAY-687, WAY-354, and AZD8055. In other aspects, the mTOR inhibitor will be a rapalog, including, for example, temsirolimus (CC1779), everolimus (RAD001), and deforolimus (AP23573). In one aspect, the inhibitor will be an AKT inhibitor including, for example, perifosine, MK2206, VQD-002, XL418, and PX316. In another aspect, the inhibitor will be a PI3K inhibitor, including, for example, BKM120, XL147, GDC0941, GSK1059615, PX-866, or CAL-101.

In some embodiments, the cancer will be one that expresses a CD70 antigen and the auristatin based antibody drug conjugate will be one that specifically binds to the CD70 antigen (e.g., the antibody component is an anti-CD70 antibody, preferably an anti-CD70 monoclonal antibody). The auristatin based antibody drug conjugate after binding to the antigen will be internalized into the cancer cells, where it exerts its effect. In one aspect, the cancer that expresses the CD70 antigen expresses pAKT (AKT phosphorylated on 5473 and T308). In one aspect, the cancer will have high pAKT expression. The cancer can be, for example, a hematological malignancy, including, for example, B cell or T cell lymphoma or leukemia. In some embodiments, the cancer is a Non-Hodgkin lymphoma, including any of the NHLs described herein (e.g., Mantle Cell Lymphoma and Diffuse Large B Cell Lymphoma). In some embodiments, the cancer is a solid tumor, including, for example, renal cell carcinoma. In some embodiments, the cancer is a leukemia, including, for example, chronic lymphocytic leukemia or acute lymphoblastic leukemia. Accordingly, combination therapy according to the present methods can include administration of the anti-CD70 auristatin based antibody drug conjugate with an inhibitor of the PI3K-AKT-mTOR pathway for the treatment of a CD70 expressing cancer (e.g., B cell or T cell lymphoma, leukemia, NHL, or solid tumor including renal cell carcinoma). In some aspects, the inhibitor will be a mTOR inhibitor, a PI3K inhibitor, or an AKT inhibitor. In some aspects, the mTOR inhibitor will be an active site inhibitor, including, for example, a dual specificity inhibitor such as wortmannin, LY294002, PI-103, BGT226, SF1126, XL765 and NVP-BEZ235 (Liu et al., Nature Review, 8, 627-644, 2009) or a selective mTOR inhibitor, including, for example, Torin1, PP242, PP30, Ku-0063794, WAY-600, WAY-687, WAY-354, and AZD8055. In other aspects, the mTOR inhibitor will be a rapalog, including, for example, temsirolimus (CC1779), everolimus (RAD001), and deforolimus (AP23573). In one aspect, the inhibitor will be an AKT inhibitor including, for example, perifosine, MK2206, VQD-002, XL418, and PX316. In another aspect, the inhibitor will be a PI3K inhibitor, including, for example, BKM120, XL147, GDC0941, GSK1059615, PX-866, or CAL-101.

In some embodiments, the cancer will be one that expresses a CD19 antigen and the auristatin based antibody drug conjugate will be one that specifically binds to the CD19 antigen (e.g., the antibody component is an anti-CD19 antibody, preferably an anti-CD19 monoclonal antibody). The auristatin based antibody drug conjugate after binding to the antigen will be internalized into the cancer cells, where it exerts its effect. In one aspect, the cancer that expresses the CD19 antigen expresses pAKT (AKT phosphorylated on 5473 and T308). In one aspect, the cancer will have high pAKT expression. The cancer can be, for example, a hematological malignancy, including, for example, a B cell lymphoma or leukemia. In some embodiments, the cancer a Non-Hodgkin lymphoma, including any of the NHLs described herein (e.g., Mantle Cell Lymphoma and Diffuse Large B Cell Lymphoma). In some embodiments, the cancer is a leukemia, including, for example, chronic lymphocytic leukemia or acute lymphoblastic leukemia. Accordingly, combination therapy according to the present methods can include administration of the anti-CD19 auristatin based antibody drug conjugate with an inhibitor of the PI3K-AKT-mTOR pathway for the treatment of a CD19 expressing cancer (e.g., B cell lymphoma, leukemia, or NHL). In some aspects, the inhibitor will be a mTOR inhibitor, a PI3K inhibitor, or an AKT inhibitor. In some aspects, the mTOR inhibitor will be an active site inhibitor, including, for example, a dual specificity inhibitor such as wortmannin, LY294002, PI-103, BGT226, SF1126, XL765 and NVP-BEZ235 (Liu et al., Nature Review, 8, 627-644, 2009) or a selective mTOR inhibitor, including, for example, Torin1, PP242, PP30, Ku-0063794, WAY-600, WAY-687, WAY-354, and AZD8055. In other aspects, the mTOR inhibitor will be a rapalog, including, for example, temsirolimus (CC1779), everolimus (RAD001), and deforolimus (AP23573). In one aspect, the inhibitor will be an AKT inhibitor including, for example, perifosine, MK2206, VQD-002, XL418, and PX316. In another aspect, the inhibitor will be a PI3K inhibitor, including, for example, BKM120, XL147, GDC0941, GSK1059615, PX-866, or CAL-101.

The anti-CD30, anti-CD19, or anti-CD70 auristatin based antibody drug conjugate for use in combination therapy with a mTOR inhibitor can have any of the structures provided herein for auristatin based antibody drug conjugates. In one aspect, the anti-CD30, anti-CD19, or anti-CD70 auristatin based antibody drug conjugate is conjugated via a linker to the auristatins MMAE or MMAF. The anti-CD30, anti-CD19, or anti-CD70 auristatin based antibody drug conjugate can be, for example, an anti-CD30, anti-CD19, or anti-CD70 vcMMAE or mcF antibody drug conjugate (e.g., cAC10-vcE, h1F6-mcF, or hBU12-mcF). In one aspect, a composition comprising anti-CD30, anti-CD19, or anti-CD70 vcMMAE or mcF antibody drug conjugates have an average of from about 2 to about 6, or from about 3 to about 5 drugs per antibody. In one aspect, each drug is attached to the antibody via a sulfur atom of a cysteine residue of a reduced interchain disulfide bond. In another aspect, each drug is attached to the antibody via a sulfur atom of an introduced cysteine residue. The cysteine residue is preferably introduced into the CH2 region of the antibody.

Combination Therapy

It has been found that combination therapy with an auristatin based antibody drug conjugate and an inhibitor of the PI3K-AKT-mTOR pathway can provide a synergistic effect.

As used herein, the term "synergy" or "synergistic effect" when used in connection with a description of the efficacy of a combination of agents, means any measured effect of the combination which is greater that the effect predicted from a sum of the effects of the individual agents.

Synergy of two compounds can be determined by use of an in vitro method. For example, synergism, additivity, or antagonism for each drug combination may be determined using the median-effect equation of Chou-Talalay:

$$D=D_m[f_a/(1-f_a)]^{1/m}$$  Median-effect equation (D) is the dose of the drug. ($D_m$) is the median-effect dose signifying the potency. This is determined by the x-intercept of the median-effect plot. ($f_a$) is the fraction affected by the dose. ($f_u$) is the fraction unaffected, ($1-f_a$). (m) is an exponent signifying the sigmoidicity (shape) of the dose-effect curve. It is determined by the slope of the median-effect plot. The linear correlation coefficient "r" should be greater than or equal to 0.90. The drug concentration units are arbitrary. Combination index (CI) values<0.9 indicate synergism, CI values 0.9-1.1 indicate additivity, and CI values>1.1 indicate antagonism.

In one example for determining in vivo synergy, tumors are harvested from donor animals, disaggregated, counted and then injected back into host mice. Anticancer combinations are typically then injected at some later time point(s), either by intraperitoneal, intravenous or administered by the oral routes, and tumor growth rates and/or survival are determined, compared to untreated controls and controls exposed only to one of the therapies. Growth rates are typically measured for tumors growing in the front flank of the animal, wherein perpendicular diameters of tumor width are translated into an estimate of total tumor mass or volume. The time to reach a predetermined mass (e.g., time for tumor to triple) is then compared to the time required for equal tumor growth in the control animals. If the time to reach the predetermined mass for the animal treated with the combination therapy is greater than the value obtained from adding the time to reach the predetermined mass for the animal treated with therapy "A" and the animal treated with therapy "B" (i.e., each therapy alone), the combination therapy can be said to provide a synergistic effect. In another example, the time to reach the predetermined mass for the animal treated with the combination therapy might not be greater than the value obtained from adding the time to reach the predetermined mass for the animal treated with therapy "A" and the animal treated with therapy "B"; however, another measured effect of the combination which is greater than that predicted from a sum of the effects of the individual agents is sufficient to identify/determine the combination therapy as synergistic. For example, if the number of durable or complete responses for the animals treated with the combination therapy is greater than the sum of the number of durable or complete responses in each treatment arm alone, the combined therapy provides a synergistic effect. A durable response (DR) is defined as the absence of palpable tumor in the animal.

Generally, the amount of the auristatin based conjugate and inhibitor of the PI3K-AKT-mTOR pathway that is effective in the treatment of cancer can be determined by standard clinical techniques. In addition, in vitro assays may optionally be employed to help identify optimal dosage ranges. The precise dose to be employed in the formulation will also depend on the route of administration, and the stage of malignancy, and should be decided according to the judgment of the practitioner and each patient's circumstances. Effective doses may be extrapolated from dose-response curves derived from in vitro or animal model test systems.

For example, in determining a synergistic interaction between two or more components, the optimum range for the effect and absolute dose range of each component for the effect may be measured by administration of the components over different w/w ratio ranges and doses to patients in need of treatment. The observation of synergy in one species can be predictive of the effect in other species and animal models exist to measure a synergistic effect and the results of such studies can be used to predict effective dose and plasma concentration ranges and the absolute doses and plasma concentrations required in other species by the application of pharmacokinetic and pharmacodynamic methods.

In some embodiments, the two drugs, the inhibitor of the PI3K-AKT-mTOR pathway and the auristatin based antibody drug conjugate will be administered to a subject at their respective maximal tolerable doses (MTD). The MTD corresponds to the highest dose of a medicine that can be given without unacceptable side effects. It is within the art to determine MTD. In some aspects, the auristatin based antibody drug conjugate will be provided at its MTD and the mTOR inhibitor will be dosed at 50%-100%, preferably at 50% to 90% of the MTD. Alternatively, the mTOR inhibitor will be dosed at 50%-100%, preferably at 50% to 90% of the MTD and the auristatin based antibody drug conjugate will be dosed at at 50%400%, preferably at 50% to 90% of the MTD. In some aspects, both the auristatin based antibody drug conjugate and mTOR inhibitor will be dosed at 60% to 90% of the MTD. In certain aspects, by dosing the mTOR inhibitor at a reduced dosage as compared to the MTD in combination with the auristatin based antibody drug conjugate, toxicity associated with treatment (i.e., adverse effects) can be reduced. In an example, in methods of treating a CD70 expressing cancer, the auristatin based antibody drug conjugate will be provided at its MTD and the inhibitor of the PI3K-AKT-mTOR pathway will be dosed at 50% to 90% of the MTD or even at 30% to 75% of the MTD. In one aspect, the inhibitor of the PI3K-AKT-mTOR pathway will be dosed at 50% to 90% of the MTD or even at 30% to 75% of the MTD and the anti-CD70 auristatin drug conjugate (e.g., h1F6-mcF) will be dosed at 0.5 mg/kg, 0.8 mg/kg, 1 mg/kg, 1.5 mg/kg, 2 mg/kg, 2.5 mg/kg, 3 mg/kg, 4.5 mg/kg or 6 mg/kg per dose (e.g., 1 mg/kg, 1.5 mg/kg, 2 mg/kg, 2.5 mg/kg 3 mg/kg, 4.5 mg/kg or 6 mg/kg every 3 weeks).

mTOR inhibitors, PI3K inhibitors and AKT inhibitors are currently provided both in oral dosage form and in i.v. form. In one exemplary embodiment, based on the results obtained with temsirolimus, the mTOR inhibitor will be provided in an i.v. infusion dosage. In one aspect, the dosage will be between, for example, about 0.1 and 100 mg/m$^2$, with between about 2.5 and 70 mg/m$^2$ being preferred. Currently, the mTOR inhibitor temsirolimus is administered at a dose of 25 to 50 mg in a weekly infusion (generally 25 mg) for the treatment of renal cell carcinoma. In another exemplary embodiment, based on the results obtained with the everolimus, the mTOR inhibitor will be provided in oral form. In one aspect, the dosage will be between from about 1 mg to about 50 mg daily, with from about 2.5 mg to 20 mg daily being preferred. Currently, the mTOR inhibitor everolimus is administered orally in a daily dose of from about 2.5 mg to 20 mg daily (generally 10 mg) for the treatment of renal cell carcinoma.

The dosage of the auristatin based antibody drug conjugate will typically be between about 0.5 mg/kg and about 15 mg/kg of the subject's body weight per dose. In some embodiments, the dosage will be between about 0.5 mg/kg to about 10 mg/kg per dose or between about 1 mg/kg to about 7 mg/kg per dose. In particular embodiments, the dosage will be about 0.8 mg/kg, about 1.0 mg/kg, about 1.2 mg/kg, about 1.8 mg/kg, about 2.0 mg/kg, about 2.7 mg/kg, about 3 mg/kg, about 3.6 mg/kg, about 4.5 mg/kg or about 6 mg/kg of the subject's body weight.

As used in this invention, the combination regimen can be given simultaneously or can be given in a sequenced regimen, with the inhibitor of the PI3K-AKT-mTOR pathway being given at a different time during the course of therapy than the auristatin based antibody drug conjugate. In one aspect, the inhibitor of the PI3K-AKT-mTOR pathway is provided prior to the drug conjugate. In another aspect, the inhibitor of the PI3K-AKT-mTOR pathway is provided following the drug conjugate. This time differential may range from several minutes, hours, days, or weeks, between administration of the two agents. Therefore, the term combination does not necessarily mean administered at the same time or as a unitary dose, but that each of the components are administered during a desired treatment period. In some methods, the respective agents are administered with sufficient proximity that for some period of time the agents are simultaneously present at detectable levels in the patient being treated, e.g., both the mTOR inhibitor and auristatin based antibody drug conjugate are detectable in the blood (e.g., serum or plasma). The agents may be administered by different routes. As typical for chemotherapeutic regimens, a course of chemotherapy may be repeated several weeks later, and may follow the same timeframe for administration of the two agents, or may be modified based on patient response. As typical with chemotherapy, dosage regimens are closely monitored by the treating physician, based on numerous factors including the severity of the disease, response to the disease, any treatment related toxicities, age, health of the patient, and other concomitant disorders or treatments.

The present invention encompasses treatment schedules wherein the antibody-drug conjugate compound is administered once during a treatment cycle. For example, in some embodiments, the antibody-drug conjugate will be administered on day 1 of a 21 day treatment cycle. In some such embodiments, the dosage of the antibody-drug conjugate compound administered to a patient will typically be, for example, 0.8 mg/kg to 8 mg/kg of the subject's body weight over the treatment cycle, preferably from about 1.5 to about 7 mg/kg, from about 1.5 mg/kg to about 6 mg/kg, from about 1.5 mg/kg to about 2.2 mg/kg, or from 1 mg/kg to about 3 mg/kg over the treatment cycle.

The present invention encompasses treatment schedules wherein the antibody-drug conjugate compound will be administered more than once during a treatment cycle. For example, in some embodiments, the antibody-drug conjugate compound will be administered weekly for three consecutive weeks in a 28 day cycle. For example, in some embodiments, the antibody-drug conjugate compound will be administered on days 1, 8, and 15 of each 28 day treatment cycle. In some such embodiments, the dosage of the antibody-drug conjugate compound administered to a patient will be 0.8 mg/kg to 8 mg/kg of the subject's body weight over the treatment cycle, preferably from about 1.5 to about 7 mg/kg, from about 1.5 mg/kg to about 6 mg/kg, from about 1.5 mg/kg to about 2.2 mg/kg, or from 1 mg/kg to about 3 mg/kg over the treatment cycle.

In one aspect, for the treatment of a CD30 expressing hematopoetic cancer such as Hodgkin lymphoma or ALCL, the auristatin based antibody drug conjugate is administered weekly at a dose of about 1 mg/kg or every three weeks at a dose of about 1.8 mg/kg.

In one aspect, for the treatment of a CD70 expressing cancer (e.g., NHL or renal cell carcinoma), the auristatin based antibody drug conjugate is administered every three weeks at a dose of about 0.5 mg/kg, 1 mg/kg, 1.5 mg/kg, 1.8 mg/kg, 2 mg/kg, 2.5 mg/kg, 3 mg/kg, 4.5 mg/kg, 6 mg/kg or 8 mg/kg.

In certain exemplary embodiments, administration of both the auristatin based antibody drug conjugate and the inhibitor of the PI3K-AKT-mTOR pathway is by infusion. In one aspect, the administration of the inhibitor of the PI3K-AKT-mTOR pathway is by i.v. (e.g., infusion) or oral administration.

The auristatin based antibody-drug conjugate and inhibitor of the PI3K-AKT-mTOR pathway can be administered as compositions including pharmaceutical compositions comprising one or more pharmaceutically compatible ingredients. For example, the pharmaceutical composition typically includes one or more pharmaceutical carriers (e.g., sterile liquids, such as water and oils, including those of petroleum, animal, vegetable or synthetic origin, such as peanut oil, soybean oil, mineral oil, sesame oil and the like). Water is a more typical carrier when the pharmaceutical composition is administered intravenously. Saline solutions and aqueous dextrose and glycerol solutions can also be employed as liquid carriers, particularly for injectable solutions. Suitable pharmaceutical excipients are known in the art. The composition, if desired, can also contain minor amounts of wetting or emulsifying agents, or pH buffering agents. Examples of suitable pharmaceutical carriers are described in "Remington's Pharmaceutical Sciences" by E. W. Martin. The formulations correspond to the mode of administration.

In typical embodiments, the pharmaceutical composition is formulated in accordance with routine procedures as a pharmaceutical composition adapted for intravenous administration to human beings. Typically, compositions for intravenous administration are solutions in sterile isotonic aqueous buffer. Where necessary, the pharmaceutical can also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the pharmaceutical is to be administered by infusion, it can be dispensed, for example, with an infusion bottle containing sterile pharmaceutical grade water or saline. Where the pharmaceutical is administered by injection, an ampoule of sterile water for injection or saline can be, for example, provided so that the ingredients can be mixed prior to administration.

In certain embodiments, the inhibitor of the PI3K-AKT-mTOR pathway may be in a form suitable for oral administration, such as in the form of a pill, capsule, solution or suspension. Such formulations may be prepared according to any method known to the art for producing oral formulations and may contain one or more agents including sweetening agents, flavoring agents, coloring agents and preserving agents. If in a tablet form, the compositions may comprise tablet excipients, such as a filler or diluent (e.g., calcium or sodium carbonate, calcium or sodium phosphate), a disintegrant (maize starch or alginic acid), a binder (e.g., starch, gelatin or acacia), a glidant, a lubricant (e.g., magnesium stearate, stearic acid or talc), an anti-adherent, a flavor, or a colorant.

The invention is further described in the following examples, which are in not intended to limit the scope of the invention.

EXAMPLES

Examples are provided to assist in a further understanding of the inventions. Particular materials used, protocols and conditions are intended to be further illustrative of the inventions and should not be construed to limit the reasonable scope thereof.

Example 1

Cell Line Culture

786-O cells were cultured in Roswell Park Memorial Institute medium (RPMI) 1640+10% fetal bovine serum (FBS). Caki-1 cells were cultured in McCoy's 5A medium+ 10% FBS. Caki-2 cells were cultured in McCoy's 5A medium+2% FBS. 786-O, Caki-1, and Caki-2 cells (renal cell carcinoma cell lines) were all cultured at 37° C. with 5% $CO_2$. L540cy cells were cultured in RPMI 1640+20% FBS. L428 cells were cultured in RPMI 1640+10% FBS. L540cy and L428 cell lines are Hodgkin lymphoma cell lines. Karpas-299 cells were cultured in RPMI 1640+10% FBS. The Karpas-299 cell line is an anaplastic large cell lymphoma cell (ALCL) line. HT cells were cultured in RPMI 1640+10% FBS. Raji 4RII cells (clone-11) were a gift from Francisco J. Hernandez-Ilizaliturri and cultured in RPMI 1640+10% FBS. HT and Raji 4RH cell lines are Non-Hodgkin lymphoma cell lines. Jeko-1 cells were cultured in RPMI-1640+10% FBS. Jeko-1 cell lines are mantle cell lymphoma cell lines.

Example 2

In Vitro Methods of Testing Auristatin ADC or Free Auristatin and mTOR Pathway Inhibitor Combinations Cells were plated in 100 µL growth media per well into black-sided clear-bottom 96-well plates. Next, 4× concentration working stocks of small molecule inhibitor and antibody drug conjugate were prepared, and then titrated as 2-fold serial dilutions producing 10-point dose curves. For the single drug conditions, 50 µL small molecule inhibitor or ADC or free auristatin was added to each well in quadruplicate with 50 µL of media producing a final volume of 200 µL per well. For the combination conditions, 50 small molecule inhibitor and 50 µL ADC or free auristatin dilution were added to the cells (overlaying the dose titrations of each drug: high to low) in quadruplicate producing a final volume of 200 µL per well. Treated cells were incubated 96 hours at 37° C., 5% $CO_2$. Cytotoxicity was measured by incubating with 100 µL Cell Titer Glo (Promega) solution for 1 hour, and then luminescence was measured on a Fusion HT plate reader (Perkin Elmer). Data was processed with Excel (Microsoft) and GraphPad (Prism) to produce dose response curves and calculate the fraction affected ($f_a$) at each dose concentration. Then CalcuSyn (Biosoft) software was used to determine synergism, additivity, or antagonism for each drug combination using the median-effect equation of Chou-Talalay:

$$D=D_m[f_a/(1-f_a)]^{1/m}$$  Median-effect equation (D) is the dose of the drug. ($D_m$) is the median-effect dose signifying the potency. This is determined by the x-intercept of the median-effect plot. ($f_a$) is the fraction affected by the dose. ($f_u$) is the fraction unaffected, $(1-f_a)$. (m) is an exponent signifying the sigmoidicity (shape) of the dose-effect curve. It is determined by the slope of the median-effect plot. The linear correlation coefficient "r" should be greater than or equal to 0.90. The drug concentration units are arbitrary.

Combination index (CI) values<0.9 indicate synergism, CI values 0.9-1.1 indicate additivity, and CI values>1.1 indicate antagonism. Table 4 shows the values of CI that correspond to synergism, additivity and antagonism.

TABLE 4

| Combination Index (CI) | Description |
| --- | --- |
| <0.1 | Very Strong Synergism |
| 0.1-0.3 | Strong Synergism |
| 0.3-0.7 | Synergism |
| 0.7-0.85 | Moderate Synergism |
| 0.85-0.90 | Slight Synergism |
| 0.90-1.10 | Nearly Additive |
| 1.10-1.20 | Slight Antagonism |
| 1.20-1.45 | Moderate Antagonism |
| 1.45-3.3 | Antagonism |
| 3.3-10 | Strong Antagonism |
| >10 | Very Strong Antagonism |

Each combination study was repeated on separate days a total of n=3 times unless otherwise noted, and the mean combination index value reported with standard error of the mean (sem).

Example 3

ELISA Assays to Test Drug Potency

Cells were plated into two 6-well plates per cell line at $2.5 \times 10^5$ cells/well in 4.5 mLs growth media. Working stocks of temsirolimus (Wyeth, Madison, N.J.) were made up at 10× concentration, and then titrated as 2-fold serial dilutions producing 10-point dose curves. Temsirolimus (0.5 mL) was added to the cells, with final concentrations equivalent to that used in the in vitro combination studies above. Treated cells were incubated 24 hours at 37° C., 5% $CO_2$. Cell pellets were collected, and lysates were prepared with the lysis buffer provided in the PathScan Phospho-S6 Ribosomal Protein (Ser235/236) Sandwich ELISA Kit (Cell Signaling, Beverly, Mass.), plus Complete Mini EDTA-free protease inhibitor (Roche Diagnostics, Mannheim, Germany). Protein concentrations were determined and 10 µg total protein extract per sample was loaded onto the ELISA plate and processed according to instructions. Plates were read using the HT Fusion (Perkin Elmer). ELISAs were performed to detect the amount of phospho-S6 phosphorylation in the presence of temsirolimus at the concentrations used in the following combination studies.

Example 4

Western Blotting of Components of the PI3K-AKT-mTOR Signaling Pathway

Primary antibodies used to measure PI3K-AKT-mTOR signaling were anti-human phospho-AKT (Ser 473) (clone: 193H12), anti-human AKT, anti-human phospho-4E-BP1 (Thr37/46), anti-human 4E-BP1, anti-human phospho-S6 ribosomal protein (Ser235/236) (clone: 2F9), and anti-human S6 ribosomal protein (clone: 54D2) (Cell Signaling; Beverly, Mass.). Secondary antibodies used were Peroxidase-AffiniPure F(ab')$_2$ Fragment Goat anti-Rabbit IgG, F(ab')$_2$ Fragment Specific, and Peroxidase-AffiniPure F(ab')2 Fragment Goat anti-Mouse IgG, Fcγ Fragment Specific (Jackson ImmunoResearch, West Grove, Pa.). Western blots were developed using SuperSignal West Pico Luminol Enhancer Solution (Thermo Scientific; Rockford, Ill.) chemiluminescent substrate and visualized following exposure to film.

Example 5

Combination Treatment with Rapalogs in Renal Cell Carcinoma

Dose response curves were generated for ADC h1F6-mcF, temsirolimus sirolimus, everolimus, h1F6-mcF+temsirolimus, h1F6-mcF+sirolimus, and h1F6-mcF+everolimus in RCC cell lines. In the RCC cell lines 786-O and Caki-2, temsirolimus and sirolimus alone are not potent cytotoxic drugs except in the Caki-2 cell line grown in media with low FBS. However, both temsirolimus and sirolimus potentiate the cytotoxicity of h1F6-mcF.

Figure 2:
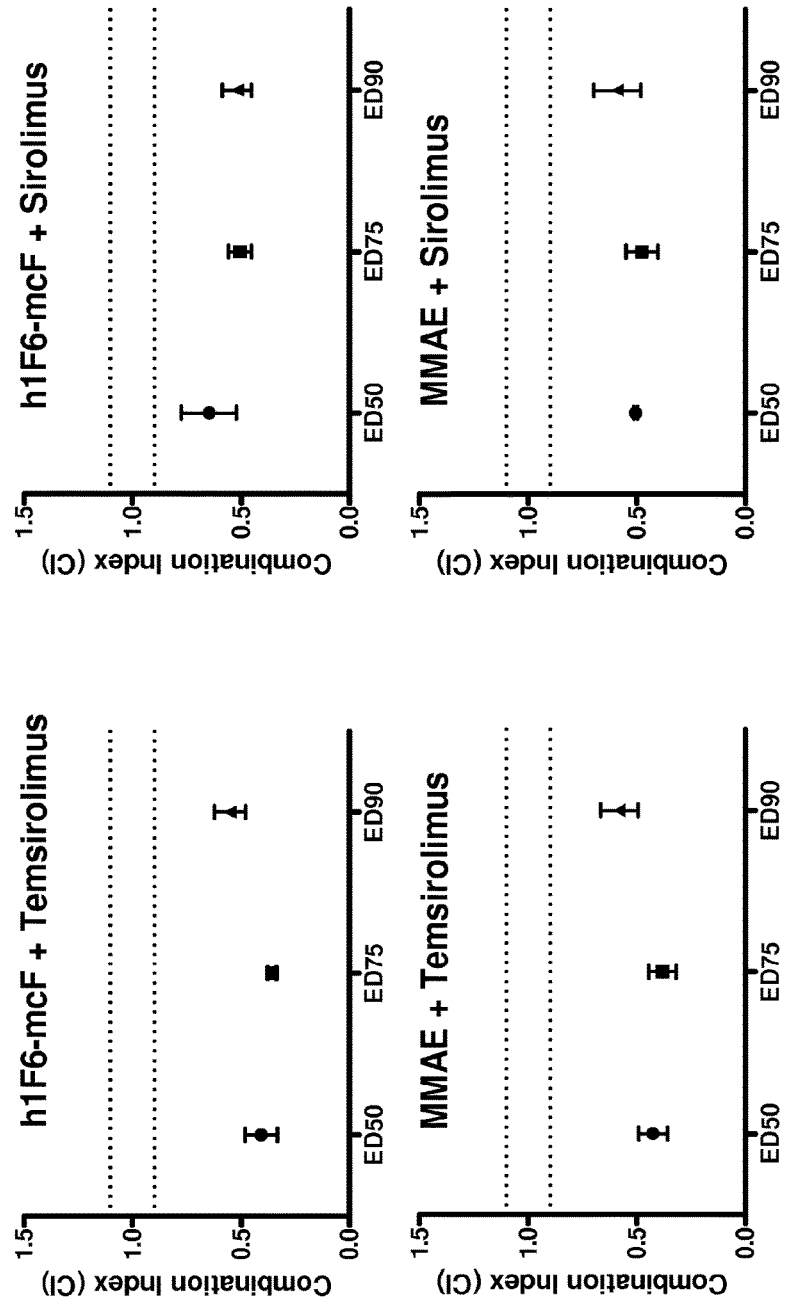
FIG. 2 shows combination indices (CIs) calculated at effective dose 50, effective dose 75 and effective dose 90 for h1F6-mcF+temsirolimus, h1F6-mcF+sirolimus, MMAE and temsirolimus and MMAE+sirolimus in the 786-O (RCC) cell line.

CIs were calculated for h1F6-mcF+temsirolimus, h1F6-mcF+temsirolimus, and h1F6-mcF+everolimus in the 786-O cell line as described above. FIG. 2 demonstrates that h1F6-mcF and MMAE alone are synergistic with the rapalogs temsirolimus, sirolimus, and everolimus in the 786-O cell line.

Figure 3:
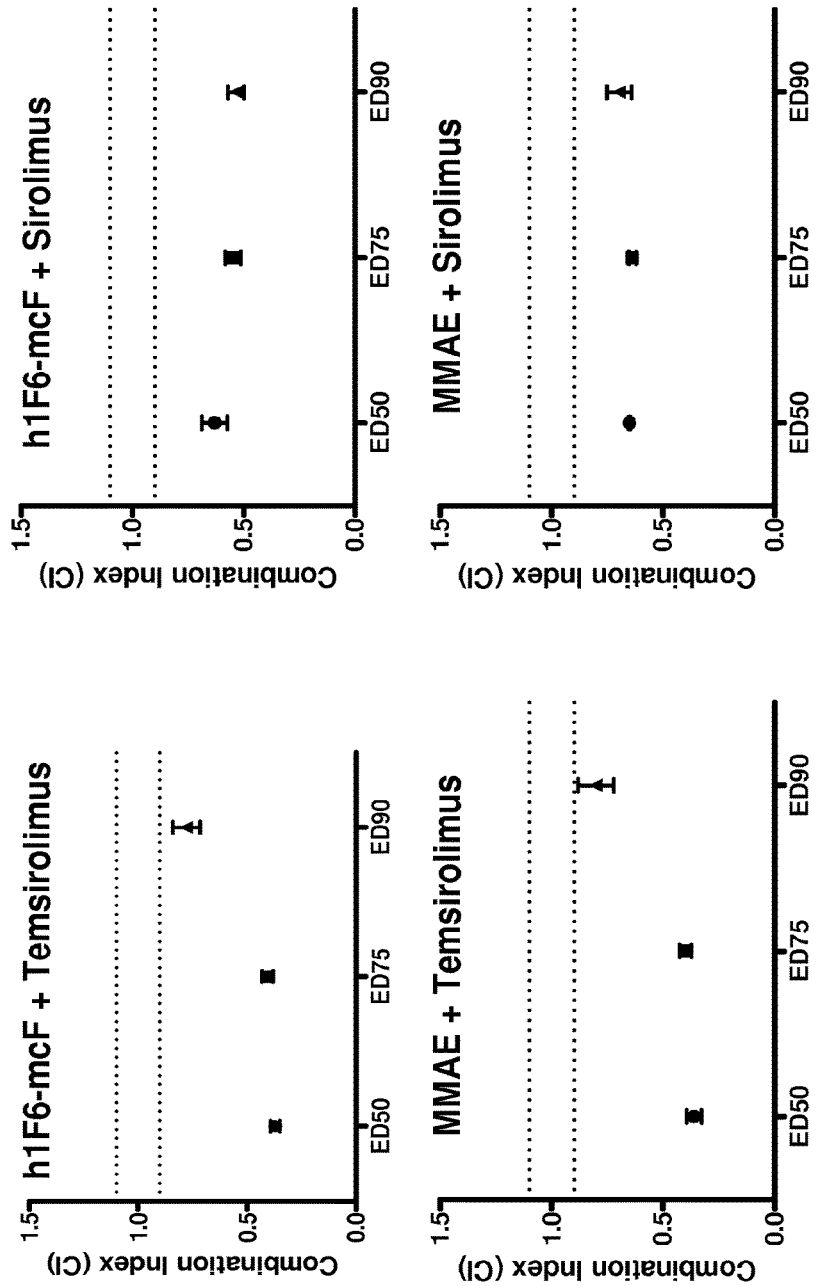
FIG. 3 shows CIs calculated at effective dose 50, effective dose 75 and effective dose 90 for h1F6-mcF+temsirolimus, h1F6-mcF+sirolimus, MMAE+temsirolimus and MMAE+sirolimus in the Caki-1 (RCC) cell line.

CIs were also calculated for h1F6-mcF+temsirolimus and h1F6-mcF+temsirolimus in the Caki-1 cell line as described above. FIG. 3 demonstrates that h1F6-mcF and MMAE alone are synergistic with the rapalogs temsirolimus and sirolimus in the Caki-1 cell line.

The results showing that h1F6-mcF is synergistic with sirolimus, temsirolimus, and everolimus are summarized in Table 5.

TABLE 5

| Cell Line | Treatment | Expt # | Average CI Values (ED50, ED75, ED90) |
|---|---|---|---|
| 786-O | h1F6-mcF + sirolimus | n = 3 | 0.65, 0.51, 0.52 |
|  | h1F6-mcF + temsirolimus | n = 3 | 0.41, 0.36, 0.55 |
|  | h1F6-mcF + everolimus | n = 3 | 0.45, 0.47, 0.59 |
|  | MMAE + sirolimus | n = 3 | 0.51, 0.48, 0.59 |
|  | MMAE + temsirolimus | n = 3 | 0.43, 0.38, 0.58 |
| Caki-1 | h1F6-mcF + sirolimus | n = 3 | 0.63, 0.55, 0.54 |
|  | h1F6-mcF + temsirolimus | n = 3 | 0.37, 0.41, 0.78 |
|  | MMAE + sirolimus | n = 3 | 0.65, 0.64, 0.70 |
|  | MMAE + temsirolimus | n = 3 | 0.36, 0.40, 0.80 |
| Caki-2 | h1F6-mcF + sirolimus | n = 3 | 0.31, 0.53, 1.33 |
|  | h1F6-mcF + temsirolimus | n = 3 | 0.11, 0.19, 0.75 |
|  | MMAE + sirolimus | n = 3 | 0.38, 0.57, 1.06 |
|  | MMAE + temsirolimus | n = 3 | 0.28, 0.51, 1.20 |

Example 6

Combination Treatment with Rapalogs in Hodgkin Lymphoma and ALCL

Figure 4:
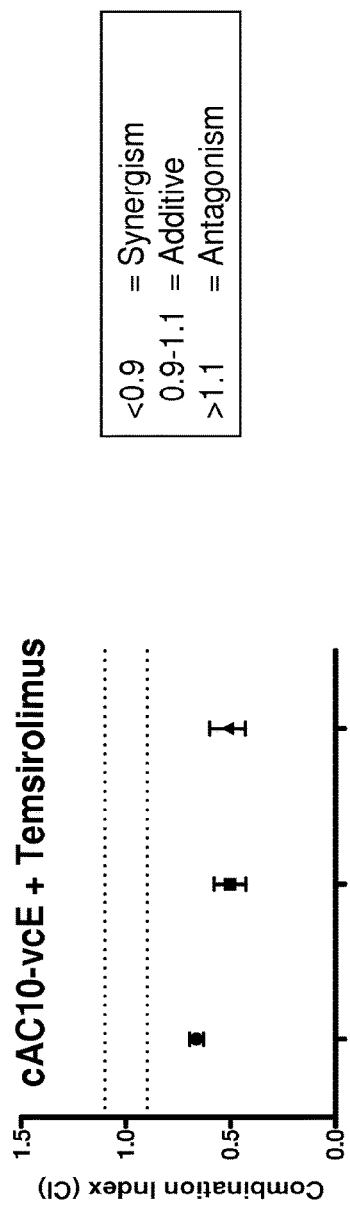
FIG. 4 shows CIs calculated at effective dose 50, effective dose 75 and effective dose 90 for cAC10-vcMMAE+temsirolimus in the L540cy (T-cell like HL) cell line and for cAC10-vcMMAE+temsirolimus and cAC10-vcMMAE+sirolimus in the Karpas-299 (ALCL) cell line.
Figure 4:
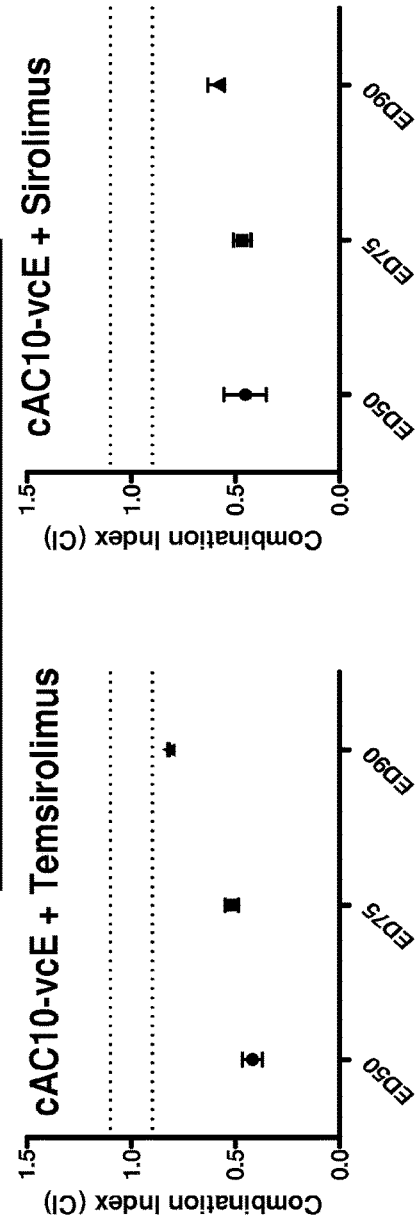

CIs were calculated for cAC10-vcE+temsirolimus, MMAE+temsirolimus, and cAC10-vcE+everolimus in the L540cy cell line as described above. CIs were calculated for cAC10-vcE+temsirolimus, MMAE+temsirolimus, and cAC10-vcE+sirolimus in the Karpas 299 cell lines as described above. FIG. 4 demonstrates that cAC10-vcE and MMAE are synergistic with the rapalogs temsirolimus and sirolimus.

The results showing that cAC10-vcE is synergistic with sirolimus, everolimus and temsirolimus are summarized in Table 6.

TABLE 6

| Cell Line | Treatment | Expt # | Average CI Values (ED50, ED75, ED90) |
|---|---|---|---|
| L540cy (T-like HL) | cAC10-vcE + temsirolimus | n = 3 | 0.66, 0.50, 0.51 |
|  | MMAE + temsirolimus | n = 3 | 0.49, 0.37, 0.40 |
| L540cy (T-like HL) | cAC10-vcE + everolimus | n = 2 | 0.31, 0.28, 0.38 |
| L428* (B-like HL) | MMAE + temsirolimus | n = 3 | 0.89, 0.70, 0.56 |
| Karpas-299 (ALCL) | cAC10-vcE + temsirolimus | n = 3 | 0.42, 0.52, 0.82 |
|  | MMAE + temsirolimus | n = 3 | 0.45, 0.47, 0.59 |
| Karpas-299 (ALCL) | cAC10-vcE + sirolimus | n = 3 | 0.45, 0.47, 0.59 |

*cAC10-vcE does not show in vitro cytotoxicity on the L428 cell line therefore a combination study was not possible.

Example 7

Figure 5:
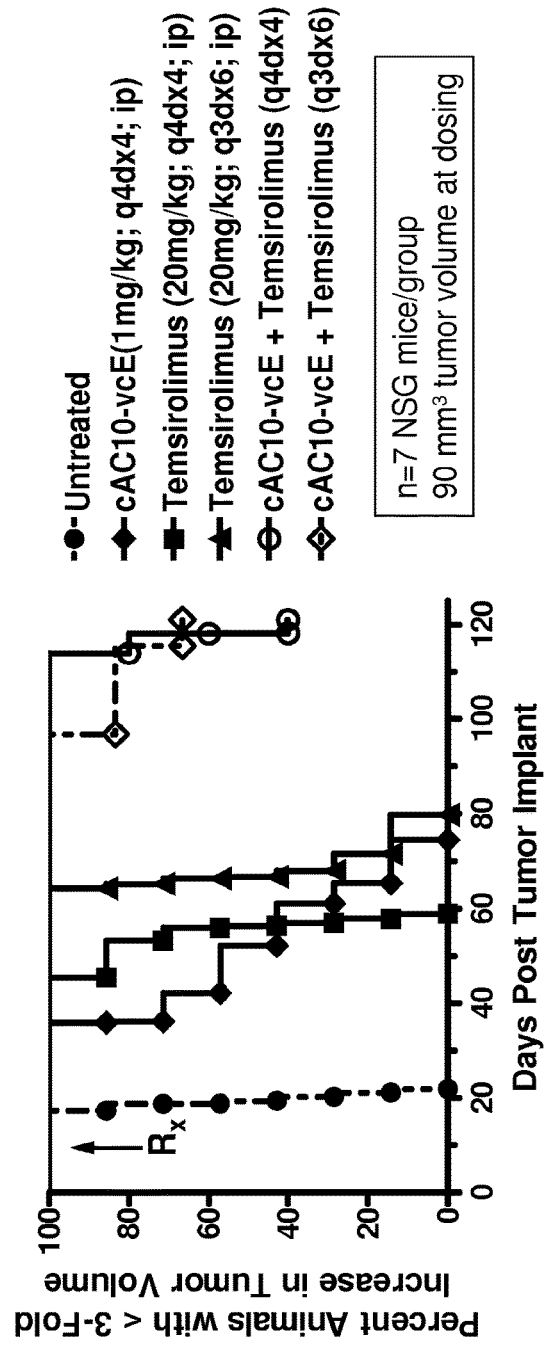
FIG. 5 shows that cAC10-vcMMAE is synergistic with temsirolimus in delaying tumor growth in vivo in a B-like IIL murine xenograft model.

In Vivo Combination Treatment of cAC10-vcE and Temsirolimus in B-Like Hodgkin Lymphoma To test combination treatments in B-like Hodgkin lymphoma in vivo, a murine xenograft model was used. L428 cells were implanted into NOD-SCID-gamma mice (The Jackson Laboratory) to generate tumors. Tumors were grown to an average of 90 mm$^3$, then sorted into groups of 7 mice. Mice were not treated, treated with temsirolimus (20 mg/kg), treated with cAC10-vcE (1.0 mg/kg), or treated with cAC10-vcE and temsirolimus. The cAC10-vcE was administered q4d×4 ip. The temsirolimus was administered q4d×4 ip or q3d×6 ip. In the combination treatment, the cAC10-vcE was dosed 2 days before temsirolimus. Tumor volume was measured periodically for 120 days post initial dosing. Data was plotted as a Kaplan-Meier plot showing rate of tumor tripling. P-values were calculated using the Log-rank test to confirm statistical significance. As can be seen in FIG. 5, cAC10-vcE plus temsirolimus has significantly better antitumor activity than either treatment alone (P-Value=0.0011 by the Log-Rank test).

TABLE 7

| Treatment | Median Days to Triple Volume | Combination vs Single Agent (P-value) |
|---|---|---|
| Untreated | 19 |  |
| cAC10-vcE | 52 | p = 0.001 |
| Temsirolimus | 56 | p = 0.001 |
| cAC10-vcE + Temsirolimus | 118 |  |

Example 8

In Vivo Combination Treatment of cAC10-vcE and Everolimus in B-Like Hodgkin Lymphoma To test combination treatments in B-like Hodgkin lymphoma in vivo, a murine xenograft model was used. L428 cells were implanted into NOD-SCID-gamma mice (The Jackson Laboratory) to generate tumors. Tumors were grown to an average of 90 mm$^3$, then sorted into groups of 10 mice. Mice were not treated, treated with everolimus (15 mg/kg), treated with cAC10 (1 mg/kg), treated with cAC10-vcE (1.0 mg/kg), treated with cAC10 and everolimus, or treated with cAC10-vcE and everolimus. The cAC10-vcE and cAC10 was administered q4dx4 ip. The everolimus was administered q1dx14 po. At day 61, the cAC10-vcE and everolimus combination treatment arm has 10/10 complete responses and the cAC10-vcE and everolimus single treatment arms had no complete responses.

Example 9

Combination Treatment with Rapalogs in Non-Hodgkin Lymphoma

Figure 6:
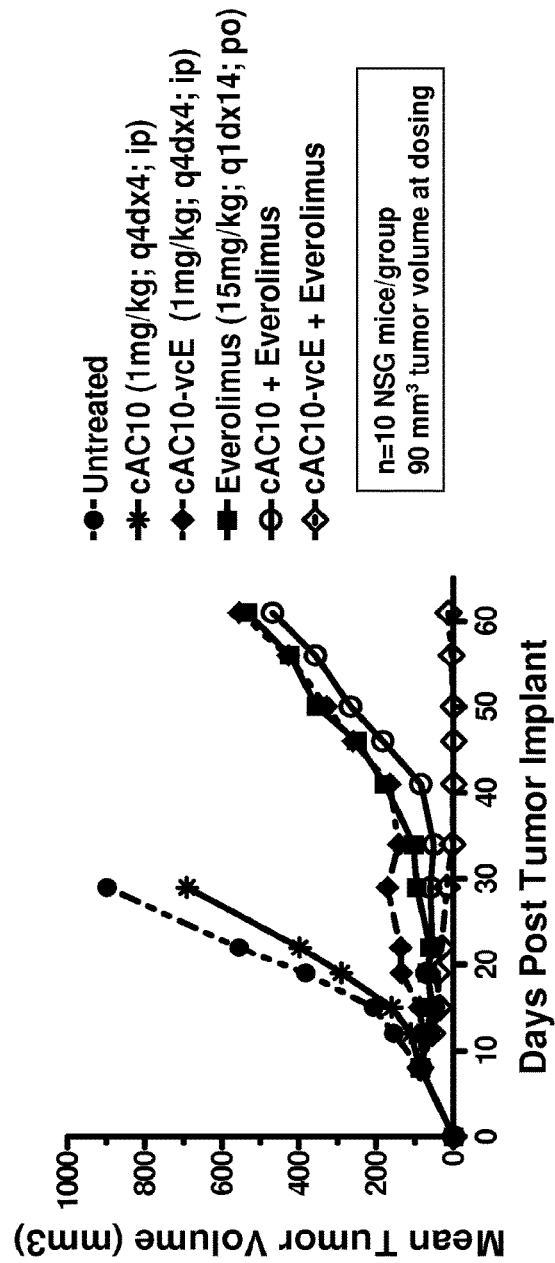
FIG. 6 shows that cAC10-vcMMAE is synergistic with everolimus in delaying tumor growth in vivo in a B-like HL murine xenograft model.
Figure 7:
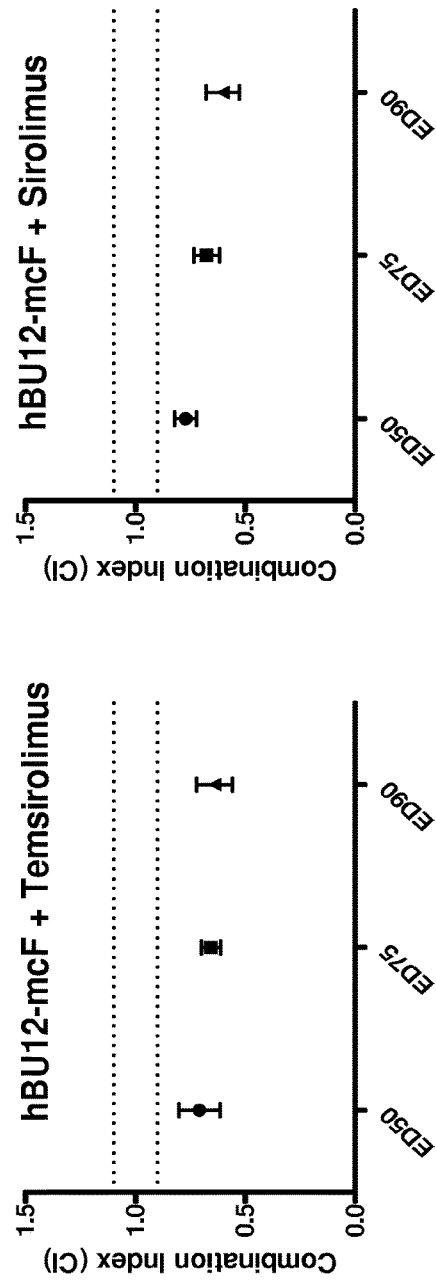
FIG. 7 shows CIs calculated at effective dose 50, effective dose 75 and effective dose 90 for hBU12-mcF+temsirolimus and hBU12-mcF+sirolimus in the HT (NHL) cell line.

CIs were calculated for hBU12-mcF+temsirolimus and hBU12-mcF+sirolimus in the HT cell line as described above. FIG. 6 demonstrates that hBU12-mcF is synergistic with the rapalogs temsirolimus and sirolimus in the HT cell line.

The results showing that hBU12-mcF is synergistic with sirolimus, temsirolimus, and everolimus are summarized in Table 8.

TABLE 8

| Cell Line | Treatment | Expt # | Average CI Values (ED50, ED75, ED90) |
|---|---|---|---|
| HT | hBU12-mcF + temsiro. | n = 3 | 0.71, 0.66, 0.64 |
|  | hBU12-mcF + sirolimus | n = 3 | 0.77, 0.68, 0.60 |
|  | hBU12-mcF + everolimus | n = 2 | 0.54, 0.55, 0.65 |
| Jeko-1 | h1F6-mcF + everolimus | n = 3 | 091, 0.69, 0.54 |

Example 10

Figure 8:
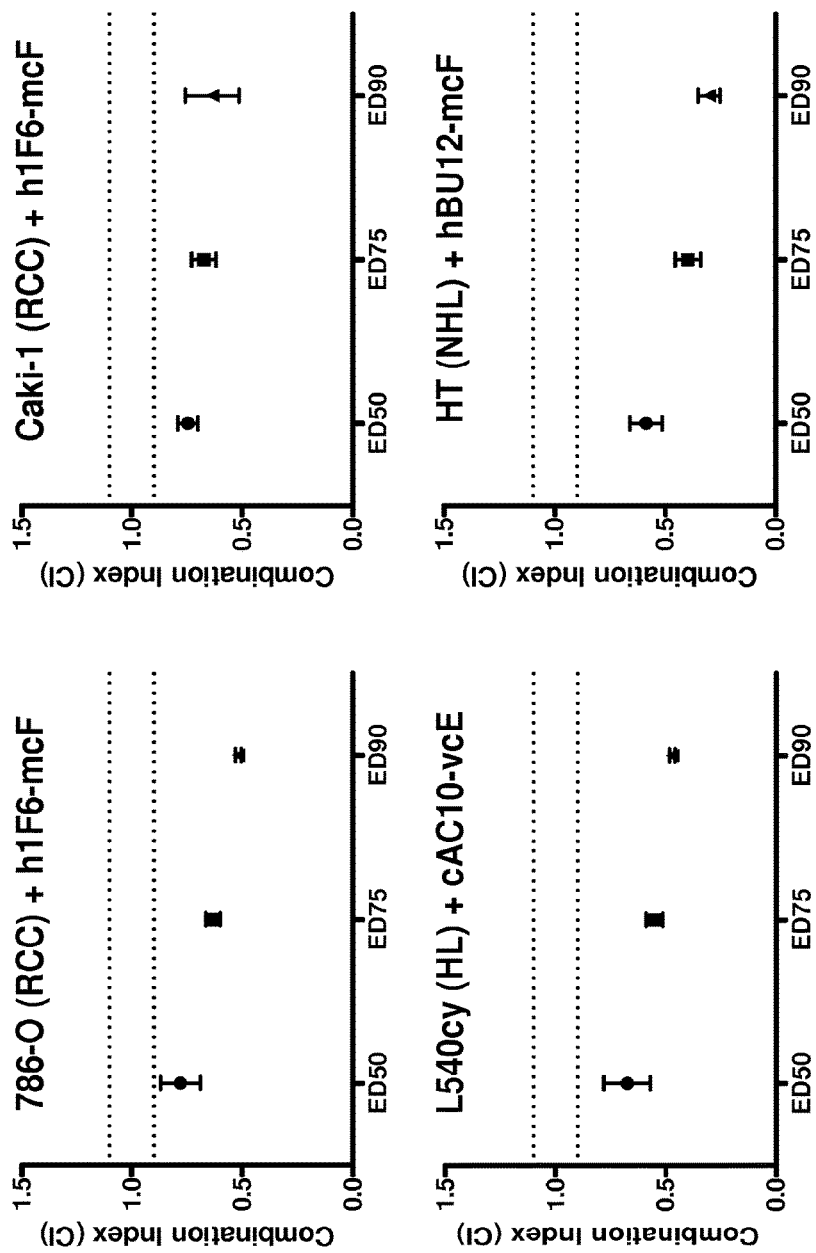
FIG. 8 shows CIs calculated at effective dose 50, effective dose 75 and effective dose 90 for h1F6-mcF+BEZ235 in the 786-O (RCC) cell line, h1F6-mcF+BEZ235 in the Caki-1 (RCC) cell line, cAC10-vcMMAE+BEZ235 in the L540cy (HL) cell line, and hBU12-mcF+BEZ235 in the HT (NHL) cell line.

Combination Treatment with Dual Specificity PI3K-mTOR Inhibitors and Selective mTor Inhibitors CIs were calculated for h1F6-mcF+BEZ235 in 786-O cells, Caki-1 cells, Jeko-1 cells, and Raji-4RH-11 cells; cAC10-vcE+BEZ235 and cAC10-vcE+PP242 in L540cy (HL) cells; cAC10-vcE+BEZ235 in Karpas-299 cells; hBU12-mcF+BEZ235 in HT cells, and h1F6-mcF+PP242 in Jeko-1 cells as described above. FIG. 8 demonstrates that NVP-BEZ235 is synergistic with auristatin ADCs (like the rapalogs temsirolimus and sirolimus) in multiple cell lines. Lower CI values were demonstrated in RCC and NHL cell lines (especially at $ED_{90}$), which suggests greater synergism.

The results showing that NVP-BEZ235 and PP242 is synergistic with auristatin ADCs is summarized in Table 9.

TABLE 9

| Cell Line | Treatment | Expt # | Average CI Values (ED5U, ED75, ED90) |
|---|---|---|---|
| 786-O | h1F6-mcF + BEZ235 | n = 3 | 0.78, 0.63, 0.52 |
| Caki-1 | h1F6-mcF + BEZ235 | n = 3 | 0.75, 0.68, 0.64 |
| L540cy | cAC10-vcE + BEZ235 | n = 3 | 0.68, 0.56, 0.47 |
|  | cAC10-vcE + PP242 | n = 2 | 0.74, 0.76, 0.79 |
|  | MMAE + BEZ235 | n = 3 | 0.91, 0.75, 0.63 |
| L428 | MMAE + BEZ235 | n = 3 | 0.62, 0.59, 0.56 |
| Karpas-299 | cAC10-vcE + BEZ235 | n = 2 | 0.81, 0.79, 0.78 |
| Raji-4RH-11 | h1F6-mcF + BEZ235 | n = 3 | 0.91, 0.71, 0.58 |

TABLE 9-continued

| Cell Line | Treatment | Expt # | Average CI Values (ED5U, ED75, ED90) |
|---|---|---|---|
| HT | hBU12-mcF + BEZ235 | n = 3 | 0.59, 0.40, 0.30 |
| Jeko-1 | h1F6-mcF + PP242 | n = 3 | 0.91, 0.76, 0.66 |
| Jeko-1 | h1F6-mcF + BEZ235 | n = 3 | 0.72, 0.55, 0.42 |

Example 11

Combination Treatment with PI3K and AKT Inhibitors

CIs were calculated for h1F6-mcF+MK-2206 in Jeko-1 cells and hBU12-mcF and XL147 in HT cells.

The results showing that PI3K and AKT inhibitors are synergistic with the auristatin ADCs is summarized in Table 10.

TABLE 10

| Cell Line | Treatment | Expt # | Average CI Values (ED50, ED75, ED90) |
|---|---|---|---|
| Jeko-1 | h1F6-mcF + MK2206 | n = 3 | 0.69, 0.54, 0.44 |
| HT | hBU12-mcF + XL147 | n = 1 | 1.08, 0.36, 0.12 |
| HT | hBU12-mcF + MK-2206 | n = 3 | 1.3, 0.95, 0.75 |
| HT | hBU12-mcF + BKM-120 | n = 3 | 0.74, 0.75, 0.79 |

Example 12

Exemplary Assays

An exemplary assay for determining whether a compound inhibits PI3K is provided in Knight et al (2006) Cell vol. 125 pp. 733-747 incorporated herein by reference in its entirety. Briefly, IC50 values are measured using either a standard TLC assay for lipid kinase activity or a high-throughput membrane capture assay. Kinase reactions are performed by preparing a reaction mixture containing kinase, inhibitor (2% DMSO final concentration), buffer (25 mM HEPES, pH 7.4, 10 mM MgCl2), and freshly sonicated phosphatidylinositol (100 μg/ml). Reactions are initiated by the addition of ATP containing 10 μCi of γ-32P-ATP to a final concentration 10 or 100 The reactions are allowed to proceed for 20 minutes at room temperature. For TLC analysis, reactions are terminated by the addition of 105 μl 1N HCl followed by 160 μl CHCl3:MeOH (1:1). The biphasic mixture is vortexed, briefly centrifuged, and the organic phase transferred to a new tube using a gel loading pipette tip precoated with CHCl3. This extract is spotted on TLC plates and developed for 3-4 hours in a 65:35 solution of n-propanol:1M acetic acid. The TLC plates are dried, exposed to a phosphorimager screen (Storm, Amersham), and quantitated. For each compound, kinase activity is typically measured at 10-12 inhibitor concentrations representing two-fold dilutions from the highest concentration tested (100 μM).

An exemplary assay for determining kinase selectivity (mTORC1/2) is as follows. To determine selectivity of a kinase inhibitor, the compound is tested against a large panel of purified protein kinases in vitro (in the presence of 10 uM ATP) at a concentration 100-fold higher than its IC50 value for inhibition of mTOR (Feldman et al. (2009) PLOS Biology vol 7(2) pp. 371-383). A difference in IC50 value of about 100-fold or more (for mTOR vs. other kinases) indicates selectivity. Each kinase has a unique protein or lipid substrate.

An exemplary assay for determining whether a compound competes with ATP for binding utilizes Michaelis-Menten kinetics to establish that the compound decreases kinase enzyme activity, but can be overcome by increasing the substrate concentration (ATP). Radiolabelled ATP (32P-ATP) incorporation into a kinase substrate (protein or peptide) is the read-out of the kinase assay. Titrating the compound will decrease the amount of 32P-ATP incorporated into the substrate. Increasing the amount of ATP present in the assay will overcome the potency of the compound only if the compound is an ATP-competitive compound.

What is claimed:

1. A method for treating cancer in a subject, comprising administering to a subject in need thereof an auristatin-based antibody drug conjugate and an inhibitor of the PI3K-AKT-mTOR pathway, wherein cells of the cancer express an antigen internalizable on binding of the antibody of the antibody drug conjugate, which antigen is CD19, CD30 or CD70, and the inhibitor is an active site mTOR inhibitor and the PI3K-AKT-mTOR pathway is constitutively activated in the cells of the cancer, and the cancer is a hematological malignancy expressing CD19, CD30 or CD70 or renal cell carcinoma expressing CD70, wherein the auristatin-based antibody drug conjugate and the inhibitor of the PI3K-AKT-mTOR pathway act synergistically in killing cancer cells in an in vitro or animal model of the cancer.

2. The method of claim 1 wherein the cancer is a lymphoma or renal cell carcinoma.

3. The method of claim 1 wherein the active site mTOR inhibitor is a selective mTOR inhibitor or a dual specificity inhibitor of PI3K and mTORC1/2.

4. The method of claim 1 wherein the auristatin based antibody drug conjugate has the following formula:

L-(LU-D)$_p$     (I)

or a pharmaceutically acceptable salt thereof;

wherein:
L is the antibody of the antibody drug conjugate; and
(LU-D) is a Linker unit-Drug unit moiety, wherein:
LU- is a Linker unit, and
-D is an auristatin having cytostatic or cytotoxic activity against the target cells; and
p is from 1 to 20.

5. The method of claim 4 wherein the auristatin has the formula:

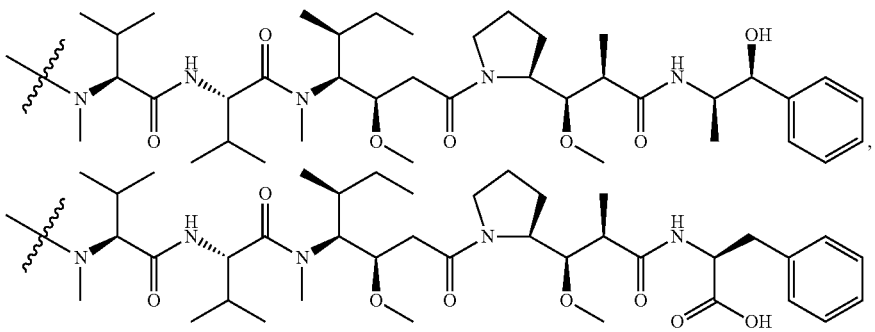

or a pharmaceutically acceptable salt form thereof.

6. The method of claim 4 wherein the auristatin based antibody drug conjugate has the formula:

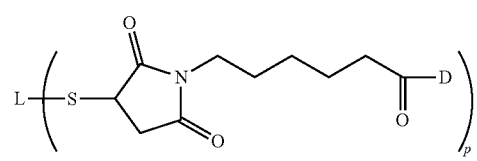

or a pharmaceutically acceptable salt form thereof.

7. The method of claim 4 wherein the auristatin based antibody drug conjugate has the formula:

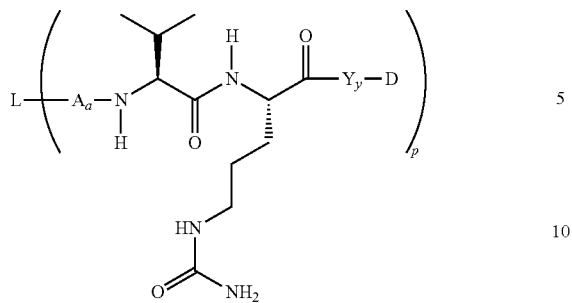

or a pharmaceutically acceptable salt form thereof, wherein a and y are independently 0 or 1.

8. The method of claim 7 wherein the auristatin based antibody drug conjugate has the formula

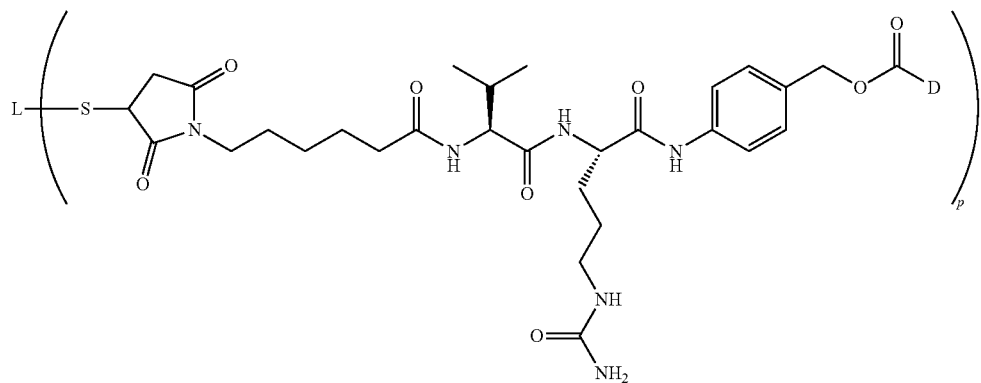

or a pharmaceutically acceptable salt form thereof wherein S is a sulfur atom of the antibody L.

9. The method of claim 1 wherein the auristatin based antibody drug conjugate has the formula:

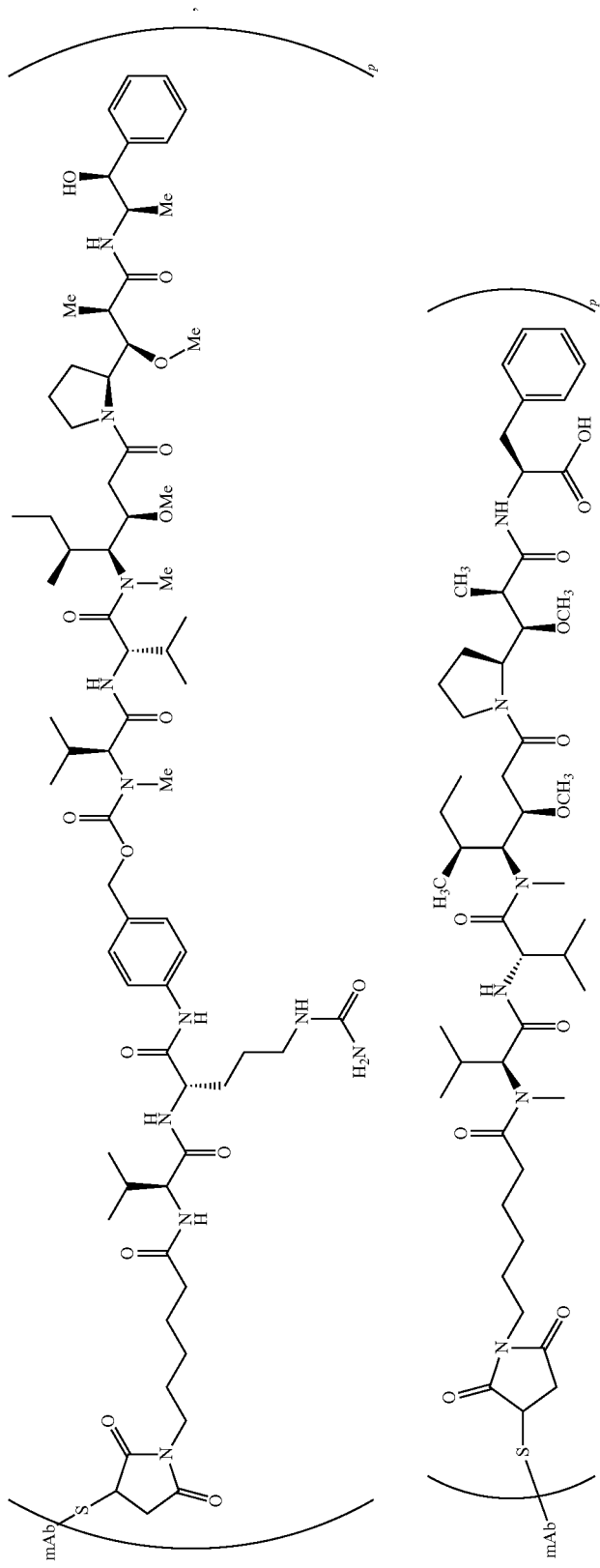

or a pharmaceutically acceptable salt form thereof, wherein mAb is a monoclonal antibody, S is a sulfur atom of the monoclonal antibody, and p is from 1 to 8 or about 2 to about 6.

10. The method of claim 1 wherein the cancer cells express the CD30 antigen and the auristatin based antibody drug conjugate is an anti-CD30 auristatin based antibody drug conjugate.

11. The method of claim 10 wherein the cancer is Hodgkin Lymphoma.

12. The method of claim 10 wherein the auristatin based antibody drug conjugate is a cAC10-vcE antibody drug conjugate.

13. The method of claim 12 wherein the cAC10-vcE antibody drug conjugate is brentuximab vedotin.

14. The method of claim 1 wherein the cancer cells express the CD70 antigen and the auristatin based antibody drug conjugate is an anti-CD70 auristatin based antibody drug conjugate.

15. The method of claim 14 wherein the cancer is renal cell carcinoma or NHL.

16. The method of claim 14 wherein the auristatin based antibody drug conjugate is h1F6-mcF.

17. The method of claim 16 wherein the h1F6-mcF antibody drug conjugate is SGN-75.

18. The method of claim 1 wherein the cancer cells express the CD19 antigen and the auristatin based antibody drug conjugate is an anti-CD19 auristatin based antibody drug conjugate.

19. The method of claim 18 wherein the cancer is diffuse large B cell lymphoma, chronic lymphocytic leukemia or acute lymphoblastic leukemia.

20. The method of claim 18 wherein the auristatin based antibody drug conjugate is hBU12-mcF.

21. The method of claim 20 wherein the hBU12-mcF conjugate is SGN-19A.

* * * * *

SEQUENCE LISTING

```
<160> NUMBER OF SEQ ID NOS: 12

<210> SEQ ID NO 1
<211> LENGTH: 117
<212> TYPE: PRT
<213> ORGANISM: Mus musculus

<400> SEQUENCE: 1

Gln Ile Gln Leu Gln Gln Ser Gly Pro Glu Val Val Lys Pro Gly Ala
1               5                   10                  15

Ser Val Lys Ile Ser Cys Lys Ala Ser Gly Tyr Thr Phe Thr Asp Tyr
            20                  25                  30

Tyr Ile Thr Trp Val Lys Gln Lys Pro Gly Gln Gly Leu Glu Trp Ile
        35                  40                  45

Gly Trp Ile Tyr Pro Gly Ser Gly Asn Thr Lys Tyr Asn Glu Lys Phe
    50                  55                  60

Lys Gly Lys Ala Thr Leu Thr Val Asp Thr Ser Ser Ser Thr Ala Phe
65                  70                  75                  80

Met Gln Leu Ser Ser Leu Thr Ser Glu Asp Thr Ala Val Tyr Phe Cys
                85                  90                  95

Ala Asn Tyr Gly Asn Tyr Trp Phe Ala Tyr Trp Gly Gln Gly Thr Gln
            100                 105                 110

Val Thr Val Ser Ala
        115

<210> SEQ ID NO 2
<211> LENGTH: 111
<212> TYPE: PRT
<213> ORGANISM: Mus musculus

<400> SEQUENCE: 2

Asp Ile Val Leu Thr Gln Ser Pro Ala Ser Leu Ala Val Ser Leu Gly
1               5                   10                  15

Gln Arg Ala Thr Ile Ser Cys Lys Ala Ser Gln Ser Val Asp Phe Asp
            20                  25                  30

Gly Asp Ser Tyr Met Asn Trp Tyr Gln Gln Lys Pro Gly Gln Pro Pro
        35                  40                  45

Lys Val Leu Ile Tyr Ala Ala Ser Asn Leu Glu Ser Gly Ile Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln Gln Ser Asn
                85                  90                  95

Glu Asp Pro Trp Thr Phe Gly Gly Gly Thr Lys Leu Glu Ile Lys
            100                 105                 110

<210> SEQ ID NO 3
<211> LENGTH: 118
<212> TYPE: PRT
<213> ORGANISM: Mus musculus
```

```
<400> SEQUENCE: 3

Gln Ile Gln Leu Val Gln Ser Gly Pro Glu Val Lys Lys Pro Gly Glu
 1               5                  10                  15

Thr Val Lys Ile Ser Cys Lys Ala Ser Gly Tyr Thr Phe Thr Asn Tyr
            20                  25                  30

Gly Met Asn Trp Val Lys Gln Ala Pro Gly Lys Gly Leu Lys Trp Met
        35                  40                  45

Gly Trp Ile Asn Thr Tyr Thr Gly Glu Pro Tyr Ala Asp Ala Phe
    50                  55                  60

Lys Gly Arg Phe Ala Phe Ser Leu Glu Thr Ser Ala Ser Thr Ala Tyr
 65                  70                  75                  80

Leu Gln Ile Asn Asn Leu Lys Asn Glu Asp Thr Ala Thr Tyr Phe Cys
                85                  90                  95

Ala Arg Asp Tyr Gly Asp Tyr Gly Met Asp Tyr Trp Gly Gln Gly Thr
            100                 105                 110

Ser Val Thr Val Ser Ser
        115

<210> SEQ ID NO 4
<211> LENGTH: 112
<212> TYPE: PRT
<213> ORGANISM: Mus musculus

<400> SEQUENCE: 4

Asp Ile Val Leu Thr Gln Ser Pro Ala Ser Leu Ala Val Ser Leu Gly
 1               5                  10                  15

Gln Arg Ala Thr Ile Ser Cys Arg Ala Ser Lys Ser Val Ser Thr Ser
            20                  25                  30

Gly Tyr Ser Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Ala
    50                  55                  60

Arg Phe Ser Gly Ser Gly Ser Gly Thr Asp Phe Thr Leu Asn Ile His
 65                  70                  75                  80

Pro Val Glu Glu Glu Asp Ala Ala Thr Tyr Tyr Cys Gln His Ser Arg
                85                  90                  95

Glu Val Pro Trp Thr Phe Gly Gly Gly Thr Lys Leu Glu Ile Lys Arg
            100                 105                 110

<210> SEQ ID NO 5
<211> LENGTH: 118
<212> TYPE: PRT
<213> ORGANISM: Artificial Sequence
<220> FEATURE:
<223> OTHER INFORMATION: Synthesized humanized heavy chain 1F6

<400> SEQUENCE: 5

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Asn Tyr
            20                  25                  30

Gly Met Asn Trp Val Arg Gln Ala Pro Gly Gln Gly Leu Lys Trp Met
        35                  40                  45

Gly Trp Ile Asn Thr Tyr Thr Gly Glu Pro Thr Tyr Ala Asp Ala Phe
    50                  55                  60

Lys Gly Arg Val Thr Met Thr Arg Asp Thr Ser Ile Ser Thr Ala Tyr
 65                  70                  75                  80
```

Met Glu Leu Ser Arg Leu Arg Ser Asp Asp Thr Ala Val Tyr Tyr Cys
                85                  90                  95

Ala Arg Asp Tyr Gly Asp Tyr Gly Met Asp Tyr Trp Gly Gln Gly Thr
            100                 105                 110

Thr Val Thr Val Ser Ser
        115

<210> SEQ ID NO 6
<211> LENGTH: 112
<212> TYPE: PRT
<213> ORGANISM: Artificial Sequence
<220> FEATURE:
<223> OTHER INFORMATION: Synthesized humanized light chain 1F6

<400> SEQUENCE: 6

Asp Ile Val Met Thr Gln Ser Pro Asp Ser Leu Ala Val Ser Leu Gly
 1               5                  10                  15

Glu Arg Ala Thr Ile Asn Cys Arg Ala Ser Lys Ser Val Ser Thr Ser
            20                  25                  30

Gly Tyr Ser Phe Met His Trp Tyr Gln Gln Lys Pro Gly Gln Pro Pro
        35                  40                  45

Lys Leu Leu Ile Tyr Leu Ala Ser Asn Leu Glu Ser Gly Val Pro Asp
50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Val Tyr Tyr Cys Gln His Ser Arg
                85                  90                  95

Glu Val Pro Trp Thr Phe Gly Gln Gly Thr Lys Val Glu Ile Lys Arg
            100                 105                 110

<210> SEQ ID NO 7
<211> LENGTH: 120
<212> TYPE: PRT
<213> ORGANISM: Mus musculus

<400> SEQUENCE: 7

Gln Val Thr Leu Lys Glu Ser Gly Pro Gly Ile Leu Gln Pro Ser Gln
 1               5                  10                  15

Thr Leu Ser Leu Thr Cys Ser Phe Ser Gly Phe Ser Leu Ser Thr Ser
            20                  25                  30

Gly Met Gly Val Gly Trp Ile Arg Gln Pro Ser Gly Lys Gly Leu Glu
        35                  40                  45

Trp Leu Ala His Ile Trp Trp Asp Asp Asp Lys Arg Tyr Asn Pro Ala
50                  55                  60

Leu Lys Ser Arg Leu Thr Ile Ser Lys Asp Thr Ser Ser Asn Gln Val
65                  70                  75                  80

Phe Leu Lys Ile Ala Ser Val Asp Thr Ala Asp Thr Ala Ala Tyr Tyr
                85                  90                  95

Cys Ala Arg Met Glu Leu Trp Ser Tyr Tyr Phe Asp Tyr Trp Gly Gln
            100                 105                 110

Gly Thr Thr Leu Thr Val Ser Ser
        115                 120

<210> SEQ ID NO 8
<211> LENGTH: 107
<212> TYPE: PRT
<213> ORGANISM: Mus musculus

```
<400> SEQUENCE: 8

Glu Asn Val Leu Thr Gln Ser Pro Ala Ile Met Ser Ala Ser Pro Gly
1               5                   10                  15

Glu Lys Val Thr Met Thr Cys Ser Ala Ser Ser Ser Val Ser Tyr Met
            20                  25                  30

His Trp Tyr Gln Gln Lys Ser Ser Thr Ser Pro Lys Leu Trp Ile Tyr
        35                  40                  45

Asp Thr Ser Lys Leu Ala Ser Gly Val Pro Gly Arg Phe Ser Gly Ser
    50                  55                  60

Gly Ser Gly Asn Ser His Phe Leu Thr Ile Ser Ser Met Glu Ala Glu
65                  70                  75                  80

Asp Val Ala Thr Tyr Tyr Cys Phe Gln Gly Ser Val Tyr Pro Phe Thr
                85                  90                  95

Phe Gly Ser Gly Thr Lys Leu Glu Ile Lys Arg
            100                 105

<210> SEQ ID NO 9
<211> LENGTH: 120
<212> TYPE: PRT
<213> ORGANISM: Artificial Sequence
<220> FEATURE:
<223> OTHER INFORMATION: Synthesized humanized heavy chain BU12

<400> SEQUENCE: 9

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Thr Ser
            20                  25                  30

Gly Met Gly Val Gly Trp Ile Arg Gln His Pro Gly Lys Gly Leu Glu
        35                  40                  45

Trp Ile Gly His Ile Trp Trp Asp Asp Lys Arg Tyr Asn Pro Ala
    50                  55                  60

Leu Lys Ser Arg Val Thr Ile Ser Val Asp Thr Ser Lys Asn Gln Phe
65                  70                  75                  80

Ser Leu Lys Leu Ser Ser Val Thr Ala Ala Asp Thr Ala Val Tyr Tyr
                85                  90                  95

Cys Ala Arg Met Glu Leu Trp Ser Tyr Tyr Phe Asp Tyr Trp Gly Gln
            100                 105                 110

Gly Thr Leu Val Thr Val Ser Ser
        115                 120

<210> SEQ ID NO 10
<211> LENGTH: 107
<212> TYPE: PRT
<213> ORGANISM: Artificial Sequence
<220> FEATURE:
<223> OTHER INFORMATION: Synthesized humanized light chain BU12

<400> SEQUENCE: 10

Glu Ile Val Leu Thr Gln Ser Pro Ala Thr Leu Ser Leu Ser Pro Gly
1               5                   10                  15

Glu Arg Ala Thr Leu Ser Cys Ser Ala Ser Ser Ser Val Ser Tyr Met
            20                  25                  30

His Trp Tyr Gln Gln Lys Pro Gly Gln Ala Pro Arg Leu Leu Ile Tyr
        35                  40                  45

Asp Thr Ser Lys Leu Ala Ser Gly Ile Pro Ala Arg Phe Ser Gly Ser
    50                  55                  60
```

```
Gly Ser Gly Thr Asp Phe Thr Leu Thr Ile Ser Ser Leu Glu Pro Glu
 65                  70                  75                  80

Asp Val Ala Val Tyr Tyr Cys Phe Gln Gly Ser Val Tyr Pro Phe Thr
                 85                  90                  95

Phe Gly Gln Gly Thr Lys Leu Glu Ile Lys Arg
            100                 105

<210> SEQ ID NO 11
<211> LENGTH: 330
<212> TYPE: PRT
<213> ORGANISM: Homo sapiens

<400> SEQUENCE: 11

Ala Ser Thr Lys Gly Pro Ser Val Phe Pro Leu Ala Pro Ser Ser Lys
  1               5                  10                  15

Ser Thr Ser Gly Gly Thr Ala Ala Leu Gly Cys Leu Val Lys Asp Tyr
                 20                  25                  30

Phe Pro Glu Pro Val Thr Val Ser Trp Asn Ser Gly Ala Leu Thr Ser
             35                  40                  45

Gly Val His Thr Phe Pro Ala Val Leu Gln Ser Ser Gly Leu Tyr Ser
 50                  55                  60

Leu Ser Ser Val Val Thr Val Pro Ser Ser Ser Leu Gly Thr Gln Thr
 65                  70                  75                  80

Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330
```

```
<210> SEQ ID NO 12
<211> LENGTH: 106
<212> TYPE: PRT
<213> ORGANISM: Homo sapiens

<400> SEQUENCE: 12

Thr Val Ala Ala Pro Ser Val Phe Ile Phe Pro Pro Ser Asp Glu Gln
1               5                   10                  15

Leu Lys Ser Gly Thr Ala Ser Val Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105
```